US012630523B2

(12) United States Patent
Weber et al.

(10) Patent No.: US 12,630,523 B2
(45) Date of Patent: May 19, 2026

(54) ISOQUINOLINE DERIVATIVES FOR USE AS ANTIVIRAL AND ANTITUMOUR AGENTS

(71) Applicants: RDP PHARMA AG, Romanshorn (CH); PAGS CO., LTD., Seoul (KR)

(72) Inventors: Lutz Weber, Stuttgart-Degerloch (DE); Christian Kühne, Vienna (AT)

(73) Assignees: RDP PHARMA AG, Romanshorn (CH); PAGS CO., LTD., South (KR)

(*) Notice: Subject to any disclaimer, the term of this patent is extended or adjusted under 35 U.S.C. 154(b) by 359 days.

(21) Appl. No.: 18/287,011

(22) PCT Filed: Apr. 14, 2022

(86) PCT No.: PCT/EP2022/060121

§ 371 (c)(1),
(2) Date: Oct. 15, 2023

(87) PCT Pub. No.: WO2022/219157

PCT Pub. Date: Oct. 20, 2022

(65) Prior Publication Data

US 2024/0208925 A1 Jun. 27, 2024

(30) Foreign Application Priority Data

Apr. 15, 2021 (EP) ..................................... 21168623
Apr. 15, 2021 (KR) ........................ 10-2021-0049335

(51) Int. Cl.
*C07D 401/06* (2006.01)
*A61K 31/472* (2006.01)
(Continued)

(52) U.S. Cl.
CPC .......... *C07D 401/06* (2013.01); *A61K 31/472* (2013.01); *A61K 31/4725* (2013.01);
(Continued)

(58) Field of Classification Search
CPC ............... C07D 401/06; A61K 31/472; A61K 31/4725; A61K 31/496; A61K 31/5377; A61K 31/436; A61K 31/473
See application file for complete search history.

(56) References Cited

U.S. PATENT DOCUMENTS

2011/0224208 A1 9/2011 Bardiot et al.

FOREIGN PATENT DOCUMENTS

EP 2149561 A1 2/2010
JP 6035334 B2 11/2016
(Continued)

OTHER PUBLICATIONS

Rothweiler et al. "Isoquinolin-1-one Inhibitors of the MDM2-p53 Interaction", ChemMedChem 2008, 3, 1118-1128.
(Continued)

*Primary Examiner* — San Ming R Hui
(74) *Attorney, Agent, or Firm* — Daniel S. Kim

(57) ABSTRACT

The present invention relates to compounds of formula (I), especially the use thereof as degraders of Human Papilloma Virus E7 proteins: formula (I).

(I)

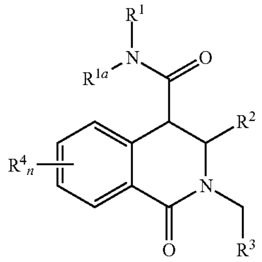

11 Claims, 10 Drawing Sheets

Figure 3D:
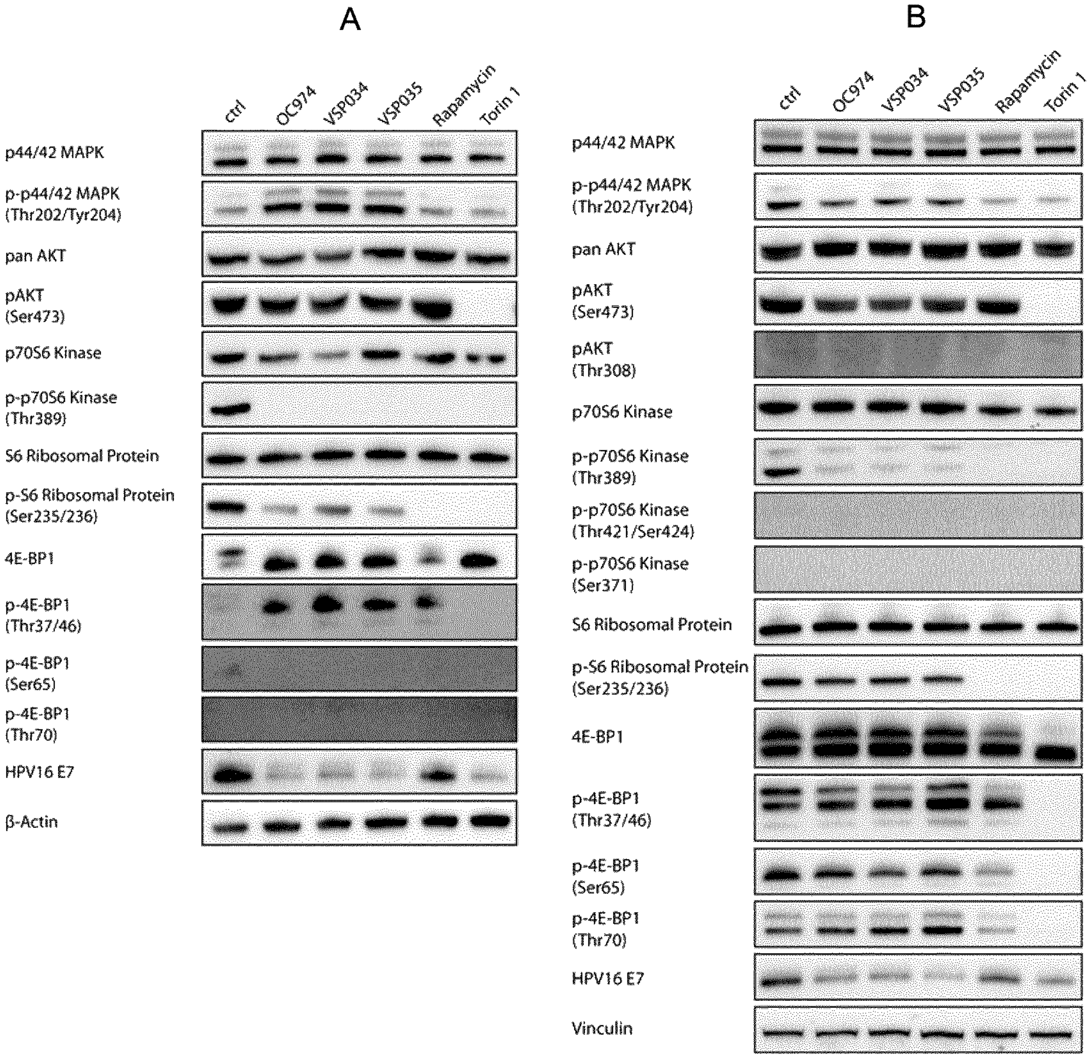

(51) Int. Cl.

| | |
|---|---|
| ***A61K 31/4725*** | (2006.01) |
| ***A61K 31/496*** | (2006.01) |
| ***A61K 31/5377*** | (2006.01) |
| ***A61P 31/14*** | (2006.01) |
| ***A61P 35/00*** | (2006.01) |
| ***C07D 217/24*** | (2006.01) |

(52) U.S. Cl.
CPC ........ *A61K 31/496* (2013.01); *A61K 31/5377* (2013.01); *A61P 31/14* (2018.01); *A61P 35/00* (2018.01); *C07D 217/24* (2013.01)

(56) References Cited

FOREIGN PATENT DOCUMENTS

| | | | |
|---|---|---|---|
| KR | 101580298 | B1 | 1/2016 |
| WO | 2006097323 | A1 | 9/2006 |
| WO | 2008034039 | A2 | 3/2008 |
| WO | 2010055164 | A2 | 5/2010 |
| WO | 2013027196 | A1 | 2/2013 |

OTHER PUBLICATIONS

H.A. Cubie, "Diseases associated with humanpapilloma virus infection", Virology 445 (2013) 21-34.

Farooq et al., "Inferring Virus-Host relationship between HPV and its host *Homo sapiens* using protein interaction network", Scientific Reports (2020) 10:8719.

Hartwig et al., "Estimation of the overall burden of cancers, precancerous lesions, and genital warts attributable to 9-valent HPV vaccine types in women and men in Europe", Infectious Agents and Cancer (2017) 12:19.

Hausen, "Papillomaviruses in the causation of human cancers—a brief historical account", Virology 384 (2009) 260-265.

Lawson et al., "Human Papilloma Virus Identification in Breast Cancer Patients with Previous Cervical Neoplasia" Front. Oncol. 5:298.

Meyers et al., "Inhibition of TGF-and NOTCH Signaling by Cutaneous Papillomaviruses", Front. Microbiol. 9:389.

Mirabello et al., "HPV16 E7 Genetic Conservation Is Critical to Carcinogenesis", 2017, Cell 170, 1164-1174.

Nakagawa et al., "Mechanisms of Coronavirus Nsp1-Mediated Control of Host and Viral Gene Expression", Cells 2021, 10, 300.

Pascale et al., "Is Human Papillomavirus Associated with Prostate Cancer Survival?", Disease Markers vol. 35 (2013), Issue 6, pp. 607-613.

Petritsch et al., "TGF-inhibits p70 S6 kinase via protein phosphatase 2A to induce G1 arrest", Genes & Development 14:3093-3101, 2000.

De Oliveira et al., "Presence and activity of HPV in primary lung cancer", Journal of Cancer Research and Clinical Oncology. 2018.

Kobayashi et al., "Identification of a human papillomavirus type 58 lineage in multiple Bowen's disease on the fingers: Case report and published work review", doi: 10.1111/1346-8138.14574, Journal of Dermatology 2018.

Ivens et al., "Development of a homogeneous screening assay for automated detection of antiviral agents active against severe acute respiratory syndrome-associated coronavirus", Journal of Virological Methods 129 (2005) 56-63.

White et al., "Crowd Control: E7 Conservation Is the Key to Cancer", Cell 170, Sep. 7, 2017.

Fig. 1a
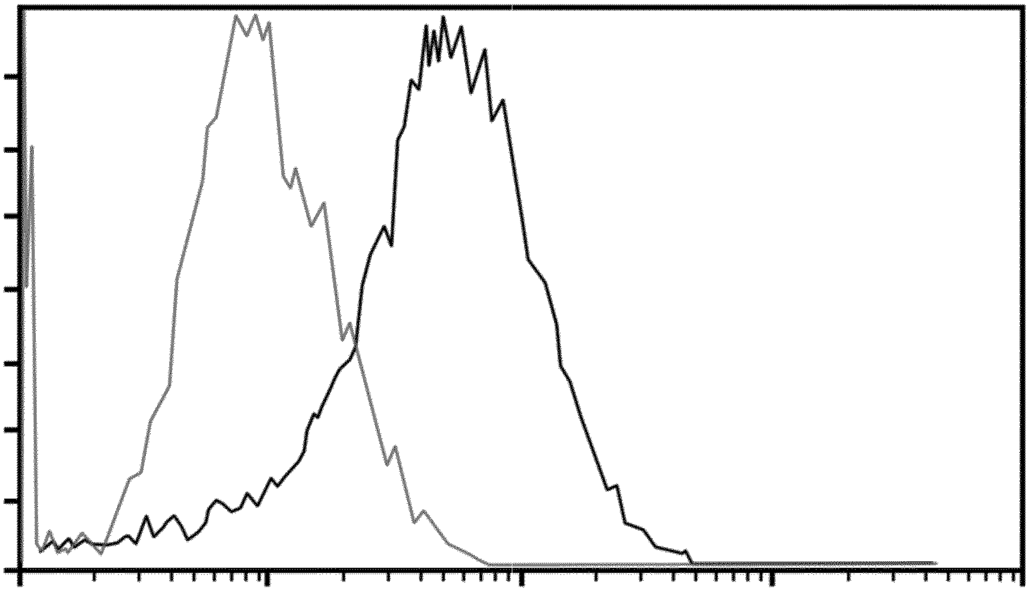
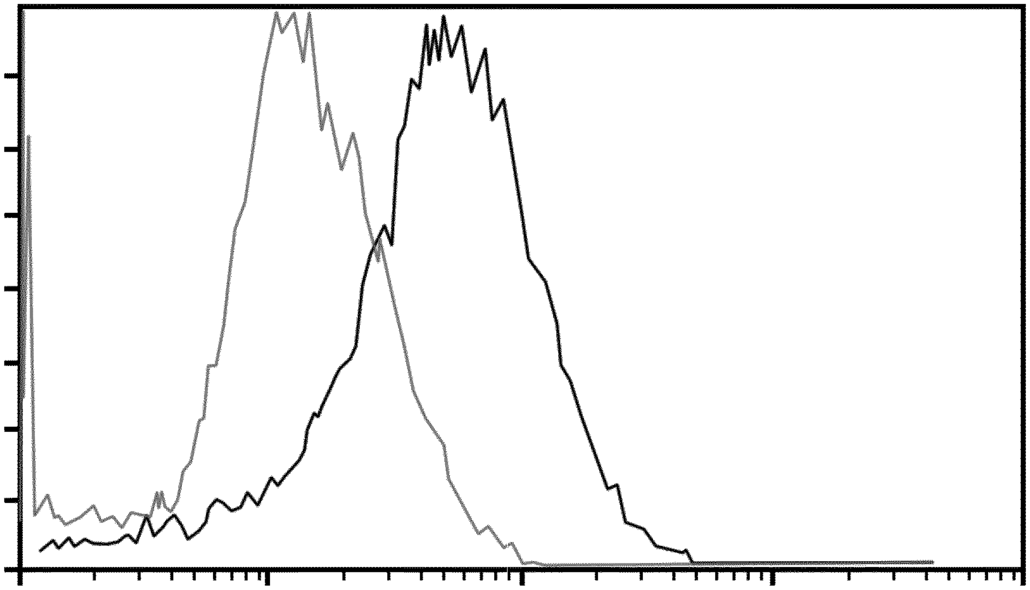
Fig. 1b

Fig. 2a
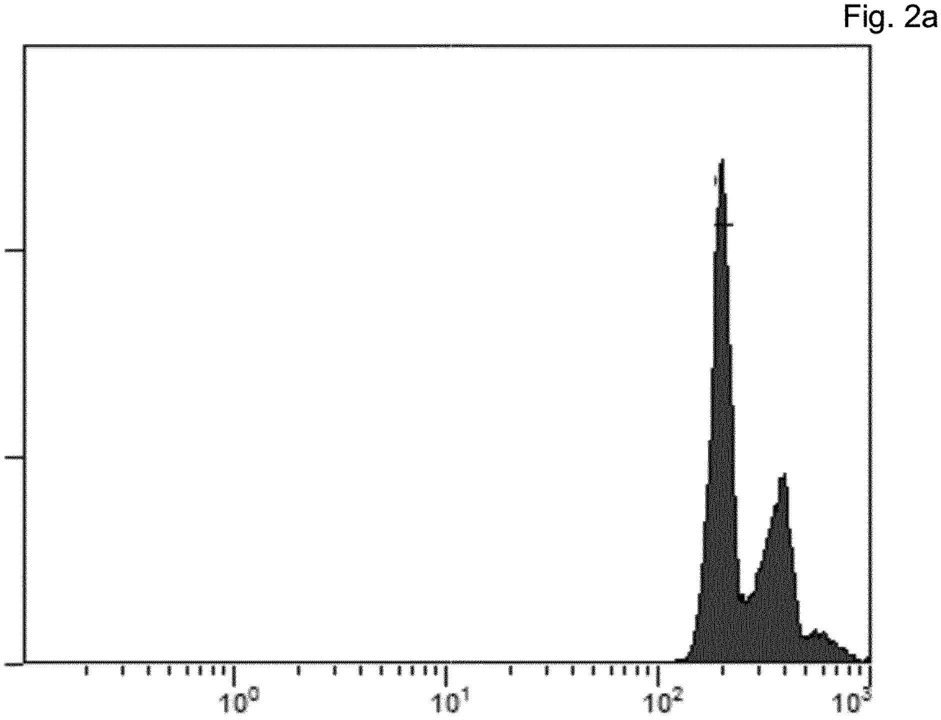
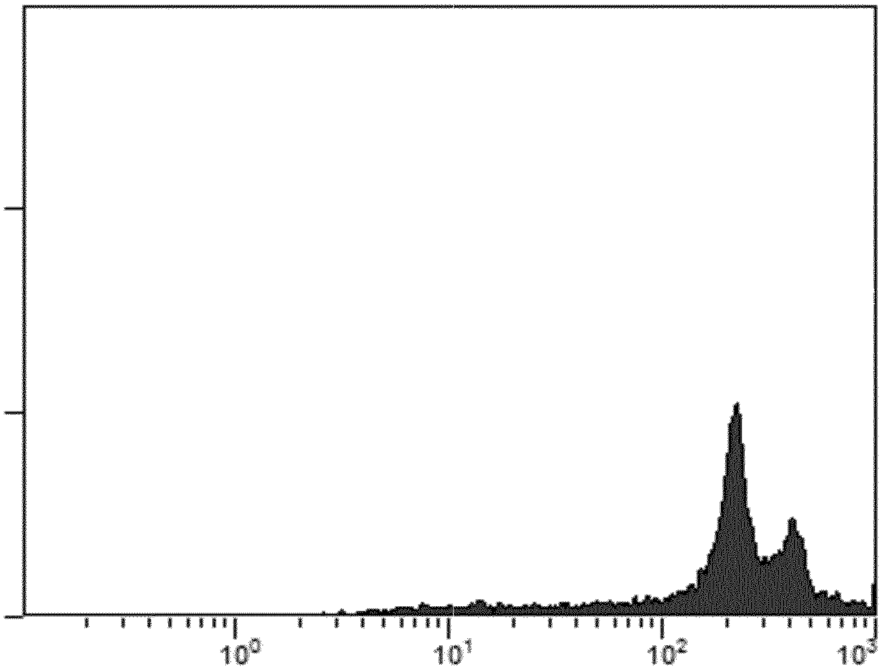
Fig. 2b

Fig. 2c
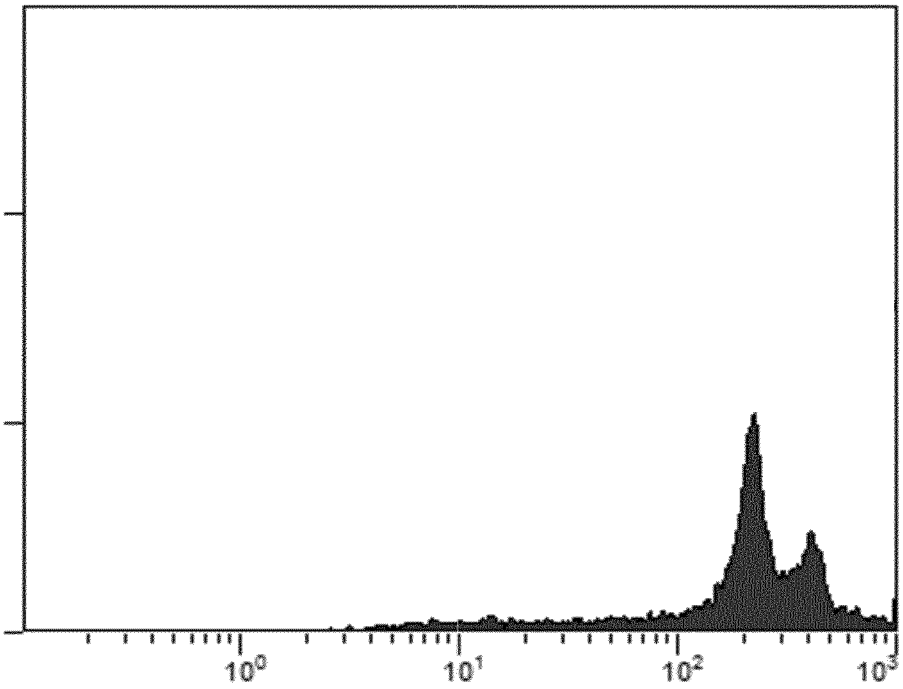
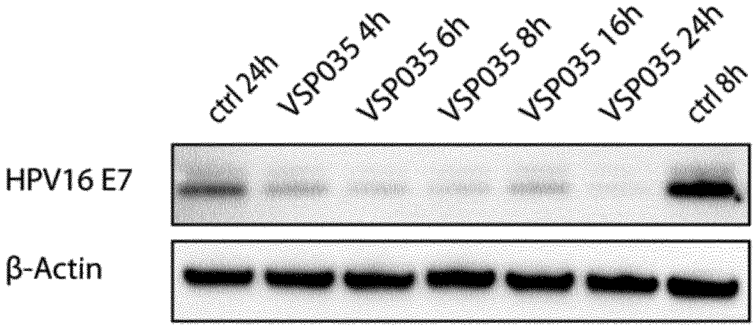
Fig. 3a

Fig. 3b
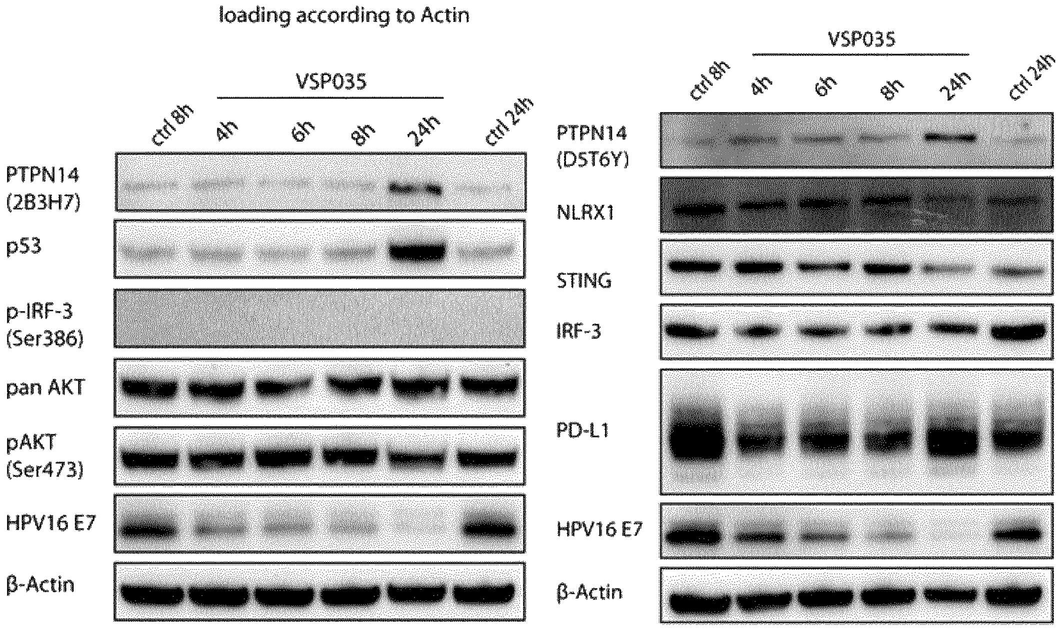
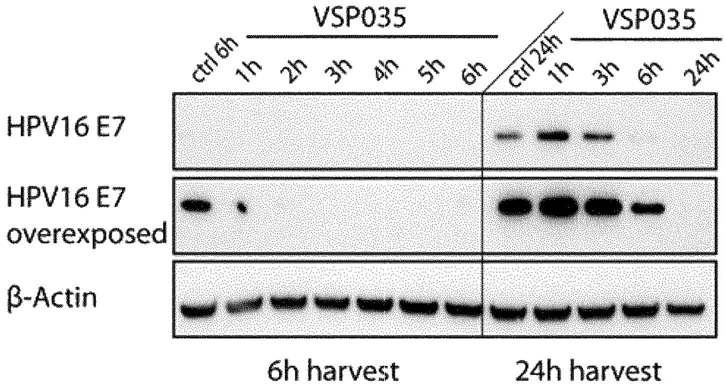
Fig. 3c

Fig. 7
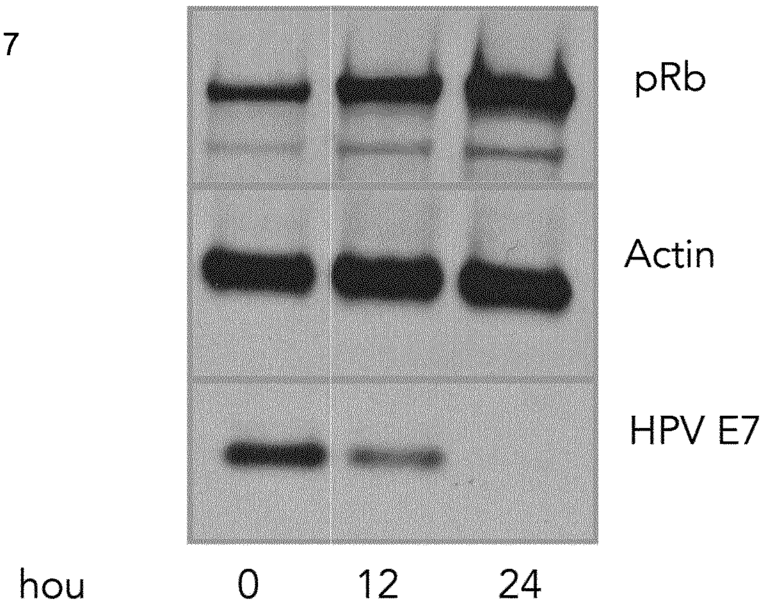
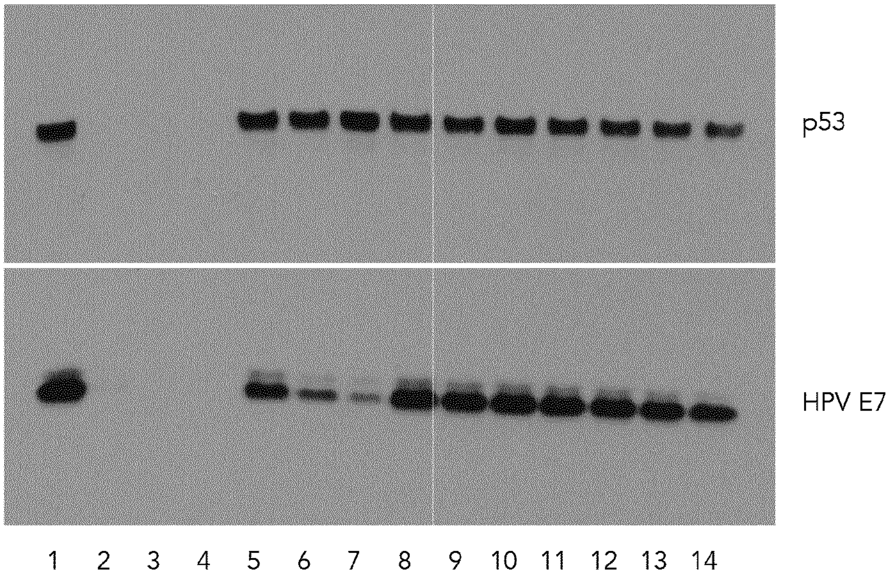
Fig. 8

Fig. 9
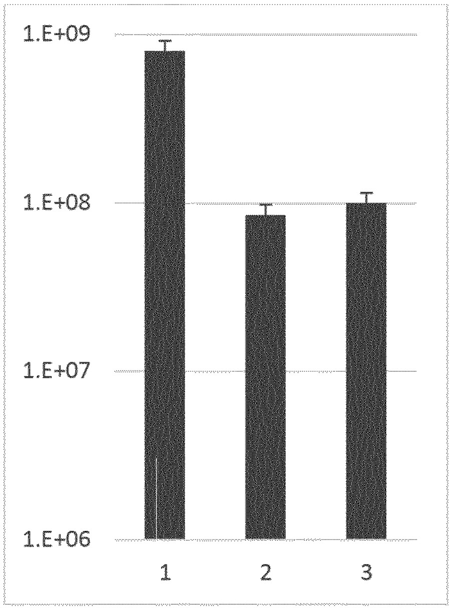
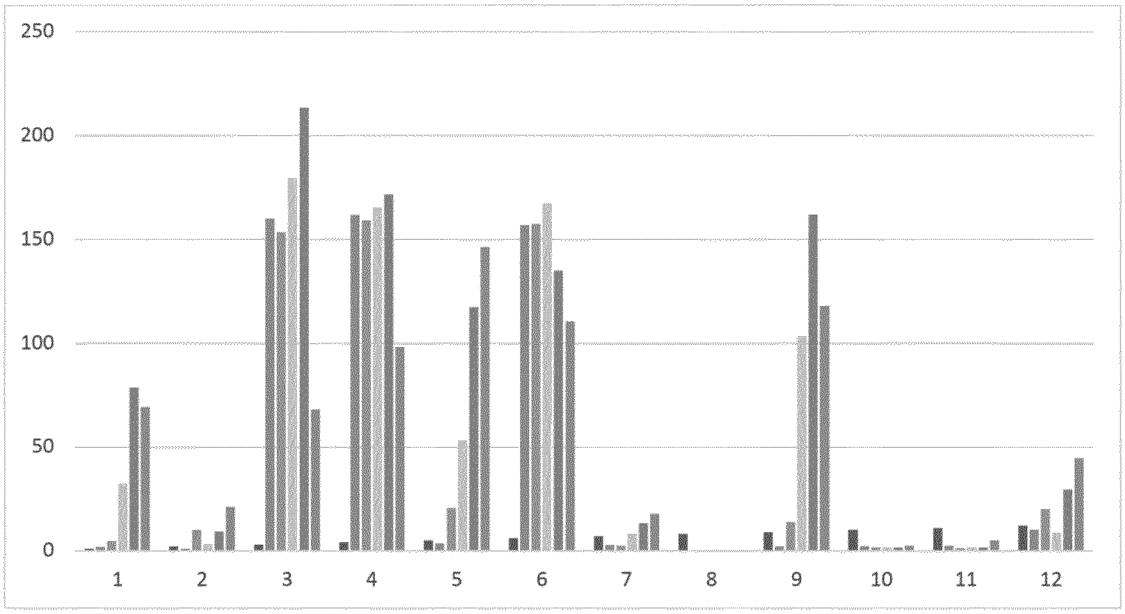
Fig. 10

ISOQUINOLINE DERIVATIVES FOR USE AS ANTIVIRAL AND ANTITUMOUR AGENTS

This is the national stage of International Application PCT/EP2022/060121, filed Apr. 14, 2022.

The present invention relates to isoquinoline compounds and their use as antiviral agents, especially antiviral agents against polyomaviridae viruses, orthomyxoviridae viruses or coronaviridae viruses, especially against human papilloma viruses (HPV).

Mechanism of Activity (MOA) studies of pathogenic viruses such as tumor Viruses, zoonotic high-risk endemic and pandemic viruses and their interaction with host cell factors has not only provided insight into basic molecular pathology principles of virus infections, but also provides phenocopies of non-infective disease conditions caused by somatic or germline mutations. In virus pathology, viral proteins hijack key host proteins that are as well central to non-infective disease, suggesting pharmacological drug targets for an integral therapeutic intervention. Viral protein expression in host cells frequently leads to gain or loss of function in cellular proteins and nucleic acids which consequently brings about distortion of cellular homeostasis. Along these lines, research of virus host interactions strongly contributes to our current knowledge in tumorigenesis, inflammation, innate and adaptive immune response and immune-suppression, latency and senescence, virulence, cell-signaling, RNA-transcription and protein-translation control, ubiquitin pathways, cellular transport, cell-cell interactions, apoptosis and phagocytosis only to name some. As a common theme, virus host cell interaction targeting principles are frequently conserved amongst very distant pathogenic virus genera. Various viruses target the tumor suppressors p53, Retinoblastoma protein (pRB), PTPN14, PDZ-binding proteins well known examples in the art.

Moreover, drug like molecules initially discovered for virus encoded, preferentially non-structural protein targets can be advantageously applied also in noninfectious disease settings where respective disease pathways are involved. Drug like molecules initially selected from anti-infective screens can be concurrently valid therapeutics for example also in oncology and/or immunology. Taken together it is this mutuality that is attractive for therapeutic interventions as it allows for robust targeting principles and broad range drugs, less amenable to drug resistance. The current invention builds on these rational principles for drug discovery and develops a class of iso-quinoline molecules as versatile degrader drug candidates.

In WO 2006/097323, WO 2010/055164 A2, WO 2013/027196 A1, EP 2 149 561 A1, US 2009/0068144, Rothweiler et al. (ChemMedChem 3 (2008), 1118-1128), US 2011/224208 A1, US 2014/235593 A1, US 2013/315954 A1 and U.S. Pat. No. 8,163,744 disclose (iso)quinolin(one)-based molecules for various uses, including cancer treatment.

It has been the object of the present invention to provide for compounds that are degraders of the E7 protein as well as for proteins of other pathogenic viruses. These compounds should preferably be pharmacologically suitable molecules with drug like properties that are able to change the homeostasis of the steady state level of a molecular disease target. Degrader targets can also be selected from any causative protein for any pathology well beyond virus protein targets. Degrader targeting by the molecules of the invention can be triggered by a direct interaction of said degraders and a given target or inter-mediated by an interference with an ectopic cellular pathway which influences the steady state level of a selected drug target.

Therefore, the present invention provides compounds of formula (I):

(I)

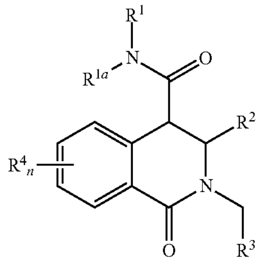

wherein $R^1$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group; all of which groups may optionally be substituted; and $R^{1a}$ is hydrogen or a $C_{1-4}$ alkyl group; or $R^1$ and $R^{1a}$ together are part of a heterocycloalkyl group containing 5 or 6 ring atoms selected from C, N and O, which heterocycloalkyl group may be unsubstituted or substituted by a group $R^{11}$;

$R^{11}$ is a $C_{1-4}$ alkyl group or a $C_{1-6}$ heteroalkyl group;

$R^2$ is a phenyl group, a naphthyl group, a heteroaryl group containing 5 or 6 ring atoms selected from C, N, O and S or a heteroaryl group comprising two rings containing a total of 9 or 10 ring atoms selected from C, N, O and S, all of which groups may be unsubstituted or substituted by one or two groups $R^{21}$;

$R^{21}$ is independently selected from halogen, a $C_{1-4}$ alkyl group and a $C_{1-4}$ heteroalkyl group;

$R^3$ is a phenyl group, a heteroaryl group containing 5 or 6 ring atoms selected from C, N, O and S, a $C_{3-7}$ cycloalkyl group or a heterocycloalkyl group containing from 3 to 7 ring atoms selected from C, N, O and S, all of which groups may be unsubstituted or substituted by one or two groups $R^{31}$;

$R^{31}$ is independently selected from halogen, a $C_{1-4}$ alkyl group and a $C_{1-4}$ heteroalkyl group;

$R^4$ is independently selected from halogen, OH, $NH_2$, SH, CN, $N_3$, $NO_2$, a $C_{1-4}$ alkyl group and a $C_{1-4}$ heteroalkyl group; or two groups $R^4$ together are a group of formula $—O—CH_2—O—$ or $—O—CH_2—CH_2—O—$; and n is 0, 1 or 2;

or a pharmaceutically acceptable salt thereof.

Preferably, $R^4$ is selected from Cl, OMe and NHAc. Especially preferably, $R^4$ is OMe.

Further preferably, n is 0 or 1.

Especially preferably, n is 0.

Further especially preferably, n is 1 and $R^4$ is OMe.

Moreover preferably, $R^{11}$ is selected from Ac, $—C(=O)—NH—CH_2CH_3$, -Me, —CHO, $CH_2CH_2—OH$ and $CH_2CH_2—OMe$.

Further preferably, $R^{1a}$ is hydrogen.

Moreover preferably, $R^1$ is a phenyl group, a naphthyl group, a heteroaryl group containing 5 or 6 ring atoms selected from C, N, O and S or a heteroaryl group comprising two rings containing a total of 9 or 10 ring atoms selected from C, N, O and S, all of which groups may optionally be substituted.

Further preferably, $R^1$ is a group of formula —Ar-Cy-$R^5$, wherein Ar is a phenylene group or a heteroarylene group containing 5 or 6 ring atoms selected from C, N and O; Cy is a $C_{3-7}$ cycloalkylene group or a heterocycloalkylene group containing 3, 4, 5, 6 or 7 ring atoms selected from C, N, O and S and $R^5$ is hydrogen or a $C_{1-4}$ alkyl group or a $C_{1-6}$ heteroalkyl group.

Especially preferably, Ar is a phenylene group and Cy is a heterocycloalkylene group containing 6 ring atoms selected from C, N and O and $R^5$ is hydrogen or a $C_{1-4}$ alkyl group.

Further especially preferably, $R^1$ is selected from the following groups:

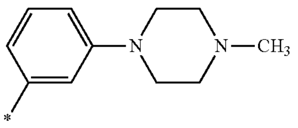

and

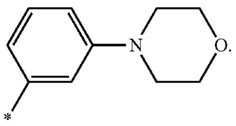

Moreover preferably, $R^1$ is a group of formula —NH—$CH_2$—$CH_2$—$N(CH_3)_2$.

Further preferably, $R^2$ is a 1,4-phenylene group carrying one group $R^{21}$, i.e. a group of formula:

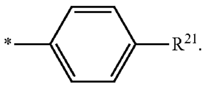

Moreover preferably, $R^{21}$ is selected from F, Cl, Br, $CF_3$, $CH_3$ and OMe; especially preferably, $R^{21}$ is a $CF_3$ group.

Further preferably, $R^{21}$ is selected from $CF_3$, $CF_2CF_3$, $CCl_3$ and $CCl_2CCl_3$.

Further preferably, $R^2$ is a 4-chlorophenyl group.

Moreover preferably, $R^3$ is a 1,4-phenylene group carrying one group $R^{31}$, i.e. a group of formula:

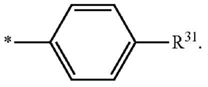

Further preferably, $R^{31}$ is selected from Cl, $CF_3$, $CH_3$, $NMe_2$ and OMe.

Further preferably, $R^{31}$ is selected from $CF_3$, $CF_2CF_3$, $CCl_3$ and $CCl_2CCl_3$.

Moreover preferably, $R^3$ is a 4-methylphenyl group.

According to a preferred embodiment, the present invention provides compounds of formula (II):

(II)

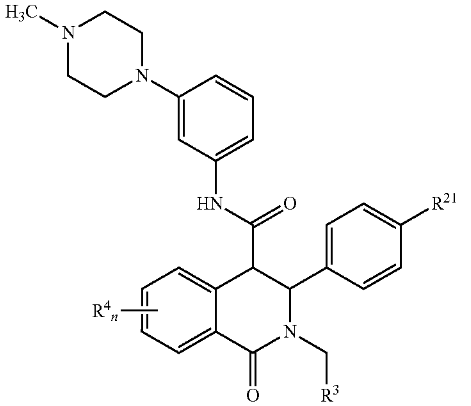

wherein $R^{21}$, $R^3$, $R^4$ and n are as defined above, or a pharmaceutically acceptable salt thereof.

Preferred are compounds of formula (II), wherein n is 0 or 1; $R^4$ is OMe; $R^{21}$ is halogen, a $C_{1-4}$ alkyl group or a $C_{1-4}$ heteroalkyl group (especially a $CF_3$ group); $R^3$ is a phenyl group, a heteroaryl group containing 5 or 6 ring atoms selected from C, N, O and S, a $C_{3-7}$ cycloalkyl group or a heterocycloalkyl group containing from 3 to 7 ring atoms selected from C, N, O and S, all of which groups may be unsubstituted or substituted by one or two groups $R^{31}$; and $R^{31}$ is independently selected from halogen, a $C_{1-4}$ alkyl group and a $C_{1-4}$ heteroalkyl group.

The most preferred compounds of the present invention are the compounds disclosed in the examples or a salt thereof.

According to one preferred embodiment, the compounds disclosed in WO 2006/097323, US 2009/0068144, US 2011/224208 A1, US 2014/235593 A1, US 2013/315954 A1 and U.S. Pat. No. 8,163,744 are excluded from the scope of the present invention.

According to a further preferred embodiment, the following compounds are excluded from the scope of the present invention:

2-(4-Chloro-benzyl)-3-(4-chloro-phenyl)-1-oxo-1,2,3,4-tetrahydro-isoquinoline-4-carboxylic acid (2-methoxy-ethyl)-amide;

2,3-Bis-(4-chloro-phenyl)-1-oxo-1,2,3,4-tetrahydro-isoquinoline-4-carboxylic acid (2-methoxyethyl)-amide;

3-(4-Chloro-benzyl)-2-(4-chloro-phenyl)-1-oxo-1,2,3,4-tetrahydro-isoquinoline-4-carboxylic acid (2-methoxy-ethyl)-amide;

2-(4-Chloro-benzyl)-3-(1H-indol-3-yl)-1-oxo-1,2,3,4-tetrahydro-isoquinoline-4-carboxylic acid (2-methoxyethyl)-amide;

(4-Chloro-phenyl)-[3-(4-chloro-phenyl)-4-(2-methoxy-ethylcarbamoyl)-1-oxo-3,4-dihydro-1H-isoquinolin-2-yl]-acetic acid;

(4-Chloro-phenyl)-[3-(4-chloro-phenyl)-4-(2-methoxy-ethylcarbamoyl)-1-oxo-3,4-dihydro-1H-isoquinolin-2-yl]-acetic acid methyl ester;

2-(4-Chloro-benzyl)-1-oxo-3-quinolin-3-yl-1,2,3,4-tetrahydro-isoquinoline-4-carboxylic acid (2-methoxyethyl)-amide;

2-(4-Chloro-benzyl)-3-naphthalen-2-yl-1-oxo-1,2,3,4-tetrahydro-isoquinoline-4-carboxylic acid (2-methoxyethyl)-amide;

2-(4-Chloro-benzyl)-3-(4-chloro-phenyl)-1-oxo-1,2,3,4-tetrahydro-isoquinoline-4-carboxylic acid; 2,3-Bis-(4-chloro-phenyl)-1-oxo-1,2,3,4-tetrahydro-isoquinoline-4-carboxylic acid;

3-(4-Chloro-benzyl)-2-(4-chloro-phenyl)-1-oxo-1,2,3,4-tetrahydro-isoquinoline-4-carboxylic acid; 2-(4-Chloro-benzyl)-3-(1H-indol-3-yl)-1-oxo-1,2,3,4-tetrahydro-isoquinoline-4-carboxylic acid;

2-[Carboxy-(4-chloro-phenyl)-methyl]-3-(4-chloro-phenyl)-1-oxo-1,2,3,4-tetrahydro-isoquinoline-4-carboxylic acid;

2-(4-Chloro-benzyl)-1-oxo-3-quinolin-3-yl-1,2,3,4-tetrahydro-isoquinoline-4-carboxylic acid;

2-(4-Chloro-benzyl)-3-(4-chloro-phenyl)-4-(morpholine-4-carbonyl)-3,4-dihydro-2H-isoquinolin-1-one;

4-(4-Acetyl-piperazine-1-carbonyl)-2-(4-chloro-benzyl)-3-(4-chloro-phenyl)-3,4-dihydro-2H-isoquinolin-1-one;

4-(4-Acetyl-piperazine-1-carbonyl)-2-(4-chloro-benzyl)-3-(4-chloro-phenyl)-3,4-dihydro-2H-isoquinolin-1-one;

2-(4-Chloro-benzyl)-3-(4-chloro-phenyl)-1-oxo-1,2,3,4-tetrahydro-isoquinoline-4-carboxylic acid (2-hydroxy-ethyl)-amide; and 2-(4-Chloro-benzyl)-3-(4-chloro-phenyl)-4-[4-(2-hydroxy-ethyl)-piperazine-1-carbonyl]-3,4-dihydro-2H-isoquinolin-1-one.

According to a moreover preferred embodiment, the following compounds are excluded from the scope of the present invention:

2-(4-Chloro-benzyl)-3-(4-chloro-phenyl)-1-oxo-1,2,3,4-tetrahydro-isoquinoline-4-carboxylic acid (2-methoxym-ethyl)-amide;

2,3-Bis-(4-chloro-phenyl)-1-oxo-1,2,3,4-tetrahydro-isoquinoline-4-carboxylic acid methoxymethyl-amide;

3-(4-Chloro-benzyl)-2-(4-chloro-phenyl)-1-oxo-1,2,3,4-tetrahydro-isoquinoline-4-carboxylic acid (2-methoxym-ethyl)-amide;

2-(4-Chloro-benzyl)-3-(1H-indol-3-yl)-1-oxo-1,2,3,4-tetrahydro-isoquinoline-4-carboxylic acid (2-methoxym-ethyl)-amide;

(4-Chloro-phenyl)-[3-(4-chloro-phenyl)-4-(methoxym-ethyl-carbamoyl)-1-oxo-3,4-dihydro-1H-isoquinolin-2-yl]-acetic acid;

2-(4-Chloro-benzyl)-1-oxo-3-quinolin-3-yl-1,2,3,4-tetrahydro-isoquinoline-4-carboxylic acid (2-methoxym-ethyl)-amide; and 2-(4-Chloro-benzyl)-3-naphthalen-2-yl-1-oxo-1,2,3,4-tetrahydro-isoquinoline-4-carboxylic acid (2-methoxym-ethyl)-amide.

According to a further preferred embodiment, the compounds disclosed in WO 2008/034039, US 2009/0306130 and U.S. Pat. No. 8,367,699 are excluded from the scope of the present invention.

According to a further preferred embodiment, the following compounds are excluded from the scope of the present invention:

2-(4-Chloro-benzyl)-3-(5-chloro-thiophen-2-yl)-1-oxo-1,2,3,4-tetrahydro-isoquinoline-4-carboxylic acid;

2-(4-Chloro-benzyl)-3-(6-chloro-1H-indol-3-yl)-1-oxo-1,2,3,4-tetrahydro-isoquinoline-4-carboxylic acid;

2-(4-Chloro-benzyl)-3-(5-chloro-pyridin-2-yl)-1-oxo-1,2,3,4-tetrahydro-isoquinoline-4-carboxylic acid;

2-(4-Chloro-benzyl)-3-(5-chloro-1H-indol-3-yl)-1-oxo-1,2,3,4-tetrahydro-isoquinoline-4-carboxylic acid;

2-(4-Chloro-benzyl)-3-(6-fluoro-1H-indol-3-yl)-1-oxo-1,2,3,4-tetrahydro-isoquinoline-4-carboxylic acid;

3-(6-Chloro-1H-indol-3-yl)-2-[(4-chloro-phenyl)-methoxycarbonyl-methyl]-1-oxo-1,2,3,4-tetrahydro-isoquinoline-4-carboxylic acid;

2-(4-Chloro-benzyl)-3-(5-chloro-thiophen-2-yl)-1-oxo-1,2,3,4-tetrahydro-isoquinoline-4-carboxylic acid (2-methoxy-ethyl)-amide;

(2-{[2-(4-chloro-benzyl)-3-(5-chloro-thiophen-2-yl)-1-oxo-1,2,3,4-tetrahydro-isoquinoline-4-carbonyl]-amino}-ethyl)-dimethyl-ammonium salt;

(2-{[2-(4-chloro-benzyl)-3-(5-chloro-thiophen-2-yl)-1-oxo-1,2,3,4-tetrahydro-isoquinoline-4-carbonyl]-amino}-ethyl)-dimethyl-ammonium formate;

2-(4-Chloro-benzyl)-3-(5-chloro-pyridin-2-yl)-1-oxo-1,2,3,4-tetrahydro-isoquinoline-4-carboxylic acid (2-methoxy-ethyl)-amide;

2-(4-Chloro-benzyl)-3-(5-chloro-1H-indol-3-yl)-1-oxo-1,2,3,4-tetrahydro-isoquinoline-4-carboxylic acid (2-methoxy-ethyl)-amide;

2-(4-Chloro-benzyl)-3-(6-chloro-1H-indol-3-yl)-1-oxo-1,2,3,4-tetrahydro-isoquinoline-4-carboxylic acid (2-methoxy-ethyl)-amide;

2-(4-Chloro-benzyl)-3-(6-fluoro-1H-indol-3-yl)-1-oxo-1,2,3,4-tetrahydro-isoquinoline-4-carboxylic acid (2-methoxy-ethyl)-amide;

[3-(6-Chloro-1H-indol-3-yl)-4-(2-methoxy-ethylcarbamoyl)-1-oxo-3,4-dihydro-1H-isoquinolin-2-yl]-(4-chloro-phenyl)-acetic acid methyl ester;

[3-(6-Chloro-1H-indol-3-yl)-4-(2-methoxy-ethylcarbamoyl)-1-oxo-3,4-dihydro-1H-isoquinolin-2-yl]-(4-chloro-phenyl)-acetic acid ester; and

[3-(6-Chloro-1H-indol-3-yl)-4-(2-methoxy-ethylcarbamoyl)-1-oxo-3,4-dihydro-1H-isoquinolin-2-yl]-(4-chloro-phenyl)-acetic acid.

According to a moreover preferred embodiment, the compounds disclosed in Rothweiler et al. ChemMedChem 2008, 3, 1118-1128 are excluded from the scope of the present invention.

Especially preferably, compounds NXN-7, NXN-574, NXN-553, NXN-552 and NXN-561 disclosed on page 1120 of Rothweiler et al. ChemMedChem 2008, 3, 1118-1128 are excluded from the scope of the present invention:

NXN-7

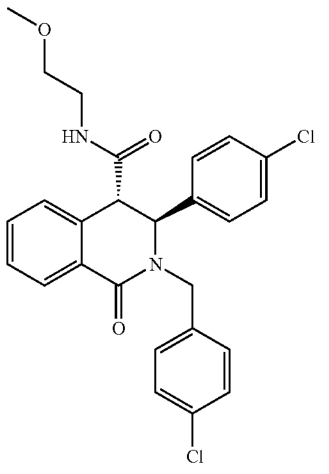

-continued

NXN-574

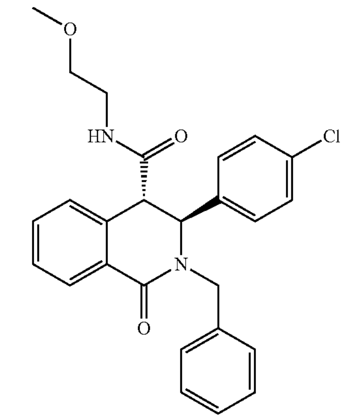

NXN-553

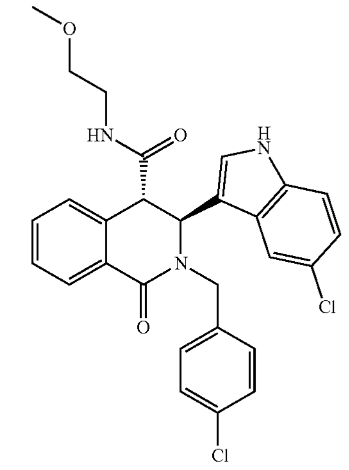

NXN-552

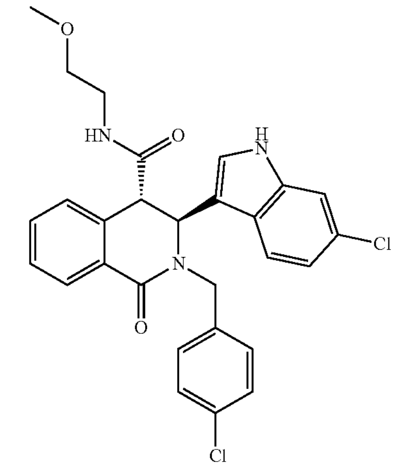

-continued

NXN-561

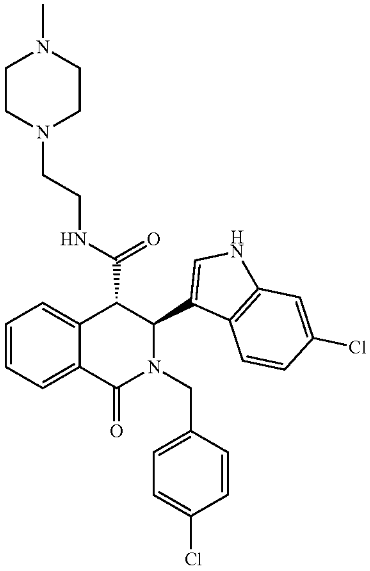

The expression alkyl refers to a saturated, straight-chain or branched hydrocarbon group that contains from 1 to 20 carbon atoms, preferably from 1 to 12 carbon atoms, especially from 1 to 6 (e.g. 1, 2, 3 or 4) carbon atoms, for example a methyl, ethyl, propyl, iso-propyl, nbutyl, isobutyl, sec-butyl, tert-butyl, npentyl, iso-pentyl, nhexyl, 2,2dimethylbutyl or noctyl group.

Furthermore, the term alkyl refers to groups in which one or more hydrogen atoms have been replaced by a halogen atom (preferably F or Cl) such as, for example, a 2,2,2-trichloroethyl or a trifluoromethyl group.

The expressions alkenyl and alkynyl refer to at least partially unsaturated, straight-chain or branched hydrocarbon groups that contain from 2 to 20 carbon atoms, preferably from 2 to 12 carbon atoms, especially from 2 to 6 (e.g. 2, 3 or 4) carbon atoms, for example an ethenyl (vinyl), propenyl (allyl), iso-propenyl, butenyl, ethinyl, propinyl, butinyl, acetylenyl, propargyl, isoprenyl or hex-2enyl group. Preferably, alkenyl groups have one or two (especially preferably one) double bond(s), and alkynyl groups have one or two (especially preferably one) triple bond(s).

Furthermore, the terms alkenyl and alkynyl refer to groups in which one or more hydrogen atoms have been replaced by a halogen atom (preferably F or Cl).

The expression heteroalkyl refers to an alkyl, alkenyl or alkynyl group in which one or more (preferably 1, 2 or 3) carbon atoms have been replaced by an oxygen, nitrogen, phosphorus, boron, selenium, silicon or sulfur atom (preferably by an oxygen, sulfur or nitrogen atom) or a group of formula SO or $SO_2$. The expression heteroalkyl furthermore refers to a carboxylic acid or to a group derived from a carboxylic acid, such as, for example, acyl, acylalkyl, alkoxycarbonyl, acyloxy, acyloxyalkyl, carboxyalkylamide or alkoxycarbonyloxy.

Preferably, a heteroalkyl group contains from 1 to 12 carbon atoms and from 1 to 4 hetero atoms selected from oxygen, nitrogen and sulphur (especially oxygen and nitrogen). Especially preferably, a heteroalkyl group contains from 1 to 6 (e.g. 1, 2, 3 or 4) carbon atoms and 1, 2 or 3 (especially 1 or 2) hetero atoms selected from oxygen, nitrogen and sulphur (especially oxygen and nitrogen). The term $C_1$-$C_6$ heteroalkyl refers to a heteroalkyl group containing from 1 to 6 carbon atoms and 1, 2, 3 or 4 heteroatoms selected from O, S and/or N (especially O and/or N). The term $C_1$-$C_4$ heteroalkyl refers to a heteroalkyl group containing from 1 to 4 carbon atoms and 1, 2 or 3 heteroatoms selected from O, S and/or N (especially O and/or N).

Furthermore, the term heteroalkyl refers to groups in which one or more hydrogen atoms have been replaced by a halogen atom (preferably F or Cl).

Examples of heteroalkyl groups are groups of formulae: $R^aOY^a$, $R^aSY^a$, $R^aSOY^a$, $R^aSO_2Y^a$, $R^aN(R^b)Y^a$, $R^aCOY^a$, $R^aOCOY^a$, $R^aCOOY^a$, $R^aCON(R^b)Y^a$, $R^aN(R^b)COY^a$, $R^aOCON(R^b)Y^a$, $R^aN(R^b)COOY^a$, $R^aN(R^b)CON(R^c)Y^a$, $R^aOCOOY^a$, $R^aN(R^b)C({=}NR^d)N(R^c)Y^a$, $R^aCSY^a$, $R^aOCSY^a$, $R^aCSOY^a$, $R^aCSN(R^b)Y^a$, $R^aN(R^b)CSY^a$, $R^aOCSN(R^b)Y_a$, $R^aN(R^b)CSOY^a$, $R^aN(R^b)CSN(R^c)Y^a$, $R^aOCSOY^a$, $R^aSCOY^a$, $R^aCOSY^a$, $R^aSCON(R^b)Y^a$, $R^aN(R^b)COSY^a$, $R^aSCOOY^a$, $R^aOCOSY^a$, $R^aSCOSY^a$, $R^aSCSY^a$, $R^aCSSY^a$, $R^aSCSN(R^b)Y^a$, $R^aN(R^b)CSSY^a$, $R^aOSCSOY^a$, $R^aOCSSY^a$, wherein $R^a$ being a hydrogen atom, a $C_1C_6$ alkyl, a $C_2C_6$ alkenyl or a $C_2C_6$ alkynyl group; $R^b$ being a hydrogen atom, a $C_1C_6$ alkyl, a $C_2C_6$ alkenyl or a $C_2C_6$ alkynyl group; $R^c$ being a hydrogen atom, a $C_1C_6$ alkyl, a $C_2C_6$ alkenyl or a $C_2C_6$ alkynyl group; Rd being a hydrogen atom, a $C_1C_6$ alkyl, a $C_2C_6$ alkenyl or a $C_2C_6$ alkynyl group and $Y^a$ being a direct bond, a $C_1C_6$ alkylene, a $C_2C_6$ alkenylene or a $C_2C_6$ alkynylene group, wherein each heteroalkyl group contains at least one carbon atom and one or more hydrogen atoms may be replaced by fluorine or chlorine atoms.

Specific examples of heteroalkyl groups are methoxy, trifluoromethoxy, ethoxy, n-propyloxy, isopropyloxy, butoxy, tert-butyloxy, methoxymethyl, ethoxymethyl, $CH_2CH_2OH$, $CH_2OH$, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, isopropylethylamino, methylamino methyl, ethylamino methyl, diisopropylamino ethyl, methylthio, ethylthio, isopropylthio, enol ether, dimethylamino methyl, dimethylamino ethyl, acetyl (Ac, $-C(=O)-CH_3$), propionyl, butyryloxy, acetyloxy, methoxycarbonyl, ethoxycarbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. The expression cycloalkyl refers furthermore to groups that may be substituted by one or more fluorine, chlorine, bromine or iodine atoms or by one or more OH, $=O$, SH, $=S$, $NH_2$, $=NH$, $N_3$ or $NO_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression heterocycloalkyl refers to a cycloalkyl group as defined above in which one or more (preferably 1, 2, 3 or 4) ring carbon atoms have been replaced by an oxygen, nitrogen, silicon, selenium, phosphorus or sulfur atom (preferably by an oxygen, sulfur or nitrogen atom) or a SO group or a $SO_2$ group. A heterocycloalkyl group has preferably 1 or 2 ring(s) containing from 3 to 10 (especially 3, 4, 5, 6 or 7) ring atoms (preferably selected from C, O, N and S). The expression heterocycloalkyl refers furthermore to groups that may be substituted by one or more fluorine, chlorine, bromine or iodine atoms or by one or more OH, $=O$, SH, $=S$, $NH_2$, $=NH$, $N_3$ or $NO_2$ groups. Examples are a piperidyl, prolinyl, imidazolidinyl, piperazinyl, morpholinyl, urotropinyl, pyrrolidinyl, tetrahydrothiophenyl, tetrahydropyranyl, tetrahydrofuryl or 2pyrazolinyl group and also lactames, lactones, cyclic imides and cyclic anhydrides.

The expression alkylcycloalkyl refers to groups that contain both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two rings having from 3 to 10 (especially 3, 4, 5, 6 or 7) ring carbon atoms, and one or two alkyl, alkenyl or alkynyl groups (especially alkyl groups) having 1 or 2 to 6 carbon atoms.

The expression heteroalkylcycloalkyl refers to alkylcycloalkyl groups as defined above in which one or more (preferably 1, 2, 3, 4 or 5) carbon atoms have been replaced by an oxygen, nitrogen, silicon, selenium, phosphorus or sulfur atom (preferably by an oxygen, sulfur or nitrogen atom) or a SO group or a $SO_2$ group. A heteroalkylcycloalkyl group preferably contains 1 or 2 rings having from 3 to 10 (especially 3, 4, 5, 6 or 7) ring atoms, and one or two alkyl, alkenyl, alkynyl or heteroalkyl groups (especially alkyl or heteroalkyl groups) having from 1 or 2 to 6 carbon atoms (the heteroalkyl groups having preferably 1, 2 or 3 heteroatoms selected from O, S and N). Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being saturated or mono-, di- or tri-unsaturated.

The expression aryl refers to an aromatic group that contains one or more rings containing from 5 or 6 to 14 ring carbon atoms, preferably from 5 or 6 to 10 (especially 6) ring carbon atoms. The expression aryl refers furthermore to groups that may be substituted by one or more fluorine, chlorine, bromine or iodine atoms or by one or more OH, SH, $NH_2$, $N_3$ or $NO_2$ groups. Examples are the phenyl, naphthyl, biphenyl, 2fluorophenyl, anilinyl, 3nitrophenyl or 4hydroxyphenyl group.

The expression heteroaryl refers to an aromatic group that contains one or more rings containing from 5 to 14 ring atoms, preferably from 5 to 10 (especially 5 or 6 or 9 or 10) ring atoms, and contains one or more (preferably 1, 2, 3, 4 or 5) oxygen, nitrogen, phosphorus or sulfur ring atoms (preferably O, S or N). The expression heteroaryl refers furthermore to groups that may be substituted by one or more fluorine, chlorine, bromine or iodine atoms or by one or more OH, SH, $NH_2$, $N_3$ or $NO_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression aralkyl refers to groups containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1 Hindene, tetraline, dihydronaphthalene, indanone, phenylcyclopentyl, cumene, cyclohexylphenyl, fluorene and indane. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or one or two cycloalkyl groups containing 5 or 6 ring carbon atoms.

The expression heteroaralkyl refers to an aralkyl group as defined above in which one or more (preferably 1, 2, 3 or 4) carbon atoms have been replaced by an oxygen, nitrogen, silicon, selenium, phosphorus, boron or sulfur atom (preferably oxygen, sulfur or nitrogen), that is to say to groups containing both aryl or heteroaryl, respectively, and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or one or two cycloalkyl groups containing 5 or 6 ring carbon atoms, wherein 1, 2, 3, 4, 5 or 6 of these carbon atoms have been replaced by oxygen, sulfur or nitrogen atoms.

Examples are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkylcycloalkyl, heteroarylalkylheterocycloalkenyl, heteroarylheteroalkylcycloalkyl, heteroarylheteroalkylcycloalkenyl and heteroarylheteroalkylheterocycloalkyl groups, the cyclic groups being saturated or mono-, di- or tri-unsaturated. Specific examples are a tetrahydroisoquinolinyl, benzoyl, 2 or 3-ethylindolyl, 4methylpyridino, 2-, 3- or 4methoxyphenyl, 4ethoxyphenyl, 2-, 3- or 4carboxyphenylalkyl group.

The term halogen or halogen atom refers to F, Cl, Br or I.

The expression "optionally substituted" preferably refers to groups in which one, two, three or more hydrogen atoms may have been replaced by fluorine, chlorine, bromine or iodine atoms or by OH, =O, SH, =S, $NH_2$, =NH, $N_3$ or $NO_2$ groups. This expression refers furthermore to groups that may be substituted by one, two, three or more (preferably unsubstituted) $C_1C_{10}$ alkyl, $C_2C_{10}$ alkenyl, $C_2C_{10}$ alkynyl, $C_1C_{10}$ heteroalkyl, $C_3C_{18}$ cycloalkyl, $C_2C_{17}$ heterocycloalkyl, $C_4C_{20}$ alkylcycloalkyl, $C_2C_{19}$ heteroalkylcycloalkyl, $C_6C_{18}$ aryl, $C_1C_{17}$ heteroaryl, $C_7C_{20}$ aralkyl or $C_2C_{19}$ heteroaralkyl groups. This expression refers furthermore especially to groups that may be substituted by one, two, three or more (preferably unsubstituted) $C_1C_6$ alkyl, $C_2C_6$ alkenyl, $C_2C_6$ alkynyl, $C_1C_6$ heteroalkyl, $C_3C_{10}$ cycloalkyl, $C_2C_9$ heterocycloalkyl, $C_7C_{12}$ alkylcycloalkyl, $C_2C_{11}$ heteroalkylcycloalkyl, $C_6C_{10}$ aryl, $C_1C_9$ heteroaryl, $C_7C_{12}$ aralkyl or $C_2C_{11}$ heteroaralkyl groups.

If a substituent contains a ring, this ring may be bonded to the respective substituted group via a single or double bond (especially a single bond) or, if the substituted group also contains a ring, the ring of the substituent may also be annulated to the ring of the substituted group.

Preferred substituents are F, Cl, Br, I, OH, =O, $NH_2$, $NO_2$, $C_{1-4}$ alkyl (e.g. methyl, $CF_3$, ethyl, t-butyl), $NMe_2$, NHMe, $CONH_2$, $CH_2NMe_2$, $NHSO_2Me$, $C(CH_3)_2CN$, COMe, OMe, SMe, COOMe, COOEt, $CH_2COOH$, $OCH_2COOH$, COOH, SOMe, $SO_2Me$, cyclopropyl, $SO_2NH_2$, $SO_2NHMe$, $SO_2CH_2CH_2OH$, $SF_5$, $SO_2NMe_2$, CHO, $OCF_3$, $SO_2CF_3$, COMe, $CH_2OH$, CN or $CF_3$.

Especially preferred substituents are F, Cl, Br, OH, $NH_2$, $CH_2NH_2$, $NO_2$, Me, Ethyl, $NMe_2$, $CONH_2$, OMe, CN or $CF_3$.

According to a preferred embodiment, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may optionally be substituted.

When an aryl, heteroaryl, cycloalkyl, alkylcycloalkyl, heteroalkylcycloalkyl, heterocycloalkyl, aralkyl or heteroaralkyl group contains more than one ring, these rings may be bonded to each other via a single or double bond or these rings may be annulated.

The present invention further provides pharmaceutical compositions comprising one or more compounds of formula (I) or (II) as defined herein or a pharmaceutically acceptable ester, prodrug, hydrate, solvate or salt thereof, optionally in combination with a pharmaceutically acceptable carrier.

It is a further aspect of the present invention to provide a compound of formula (I) or (II) as defined herein or a pharmaceutical composition as defined herein for the preparation of a medicament for the treatment of one or more diseases mentioned herein.

The compounds of the present invention are specifically suitable to be used as antiviral agents, preferably as an antiviral agent against a polyomaviridae virus, an orthomyxoviridae virus, especially Influenza A virus, or a coronaviridae virus, a human immunodeficiency virus (HIV), a Merkel cell polyomavirus (MCV, MCPyV), a JC polyomavirus (JCV, JCPyV), a BK polyomavirus (BKV, BKPyV), a TS polyomavirus (TSV, TSPyV), a H7 polyomavirus (HV7, HPyV7), a Simian polyomavirus 40 (SV40), a Cytomegalovirus (CMV), a Hepatitis B Virus (HEPB), a Hepatitis C Virus (HEPC), a Hepatitis D Virus (HEPD), a Human immunodeficiency virus 1 (HIV-1), a Human immunodeficiency virus 2 (HIV-2), a Human T-lymphotropic virus I (HTLV-I), a Human T-lymphotropic virus II (HTLV-II), an Epstein Bar Virus (EBV), a Karposi sarcoma-associated herpesvirus (Herpesviridae; KSHV), especially against human papilloma viruses (HPV). The compounds of the present invention have been proven to work excellently as antiviral agents for use in the treatment of a human papilloma virus (HPV) infection or for use in the treatment or prevention of SARS-CoV-2 infection, especially for use in the treatment of HPV induced malignant and neoplastic diseases, especially as a degrader of protein E7, or for use in the treatment or prevention of COVID-19. The compounds of the present invention are therefore preferably used in a method for treating a human patient with a viral infection or being at risk of being infected with a virus to develop a disease caused by a viral pathogen, wherein the method comprises administering an effective amount of one or more of the compounds according to the present invention to this patient in need of this antiviral compound.

DNA Viruses

HPV

The DNA tumor virus, human papilloma virus (HPV) is the causative agent for a significant proportion of cancers and precancerous lesions of the cervix, vulva, vagina, anus, penis, head and neck, as well as genital warts (Diseases associated with human papillomavirus infection Heather A. Cubie, Virology 445 (2013) 21-34; Hartwig et al., Estimation of the overall burden of cancers, precancerous lesions, and genital warts attributable to 9-valent HPV vaccine types in women and men in Europe, Infectious Agents and Cancer (2017) 12:19) and is involved in 5% of all the cancers. These include Squamous Cell Carcinomas (SCC) as well as Adenocarcinoma (ADC). Moreover, there are reports that HPV has its role also in a sub-portion of prostate (Pascale M, et al. Is human papillomavirus associated with prostate cancer survival? Dis Markers. 2013; 35(6): 607-13), lung cancers (Talita Helena Araujo de OliveiraCarolina Medeiros do AmaralBianca de França São et al., Presence and activity of HPV in primary lung cancer, Journal of Cancer Research and Clinical Oncology, December 2018, Volume 144, Issue 12, pp 2367-2376), breast cancers (Lawson J S, et al. Human Papilloma Virus Identification in Breast Cancer Patients with Previous Cervical Neoplasia. Front Oncol. 2016 Jan. 8; 5: 298) and Bowen's disease (Kobayashi K. et al., Identification of a human papillomavirus type 58 lineage in multiple Bowen's disease on the fingers: Case report and published work review, J Dermatol. 2018 October; 45(10): 1195-1198. doi: 10.1111/1346-8138.14574. Epub 2018 July 231). There is increasing evidence that other subtypes of HPV such as beta HPV types are inducing actinic keratosis and non-melanoma skin cancer (Inhibition of TGF-β and NOTCH Signaling by Cutaneous Papillomaviruses, Meyers J M, Grace M, Uberoi A, Lambert P F, Munger K. Front Microbiol. 2018 Mar. 8; 9: 389. doi: 10.3389/fmich.2018.00389. eCollection 2018. Review.PMID: 29568286).

Worldwide, the most prominent of HPV cancers, uterine cervical cancer, is the fourth most common cause of cancer related death in women, with an estimated 527,624 new cases and 265,672 deaths in 2012. It shows a global 5-year prevalence of 1.547.161 (proportion of 59,6/100.000). More than 85% of the global burden and 88% of deaths occur in countries with low to medium medical environment where cervical cancer accounts for 12% of all female cancers (GLOBOCAN 2012). HPV induced cancer is a sexual transmitted disease and HPV is generally not only accepted as the causative agent for tumor induction, but also for tumor progression and maintenance (zur Hausen H. Papillomaviruses in the causation of human cancers—a brief historical account. *Virology* 2009; 384(2): 260-265), which makes the tumor maintaining HPV compounds E6 or E7 the prime target for a therapeutic intervention to cure the disease. Despite its prominent role in genital cancers other HPV cancers such as head and neck cancers and in particular oropharyngeal cancer, are rapidly increasing foreseeing that HPV-positive oropharyngeal cancers will outnumber uterine cervical cancers in the next 15 years.

High risk HPV infections bring about the viral oncogenes E6 and E7 and it is the continuous expression of the respective proteins that drives tumor induction, progression and maintenance of the cancerous state. Loss of function, in particular of E7, leads to reversal of the cancerous phenotype in different experimental systems. The dominant, unique role of E7 in HPV induced cancer maintenance was recently confirmed by Next-Gen Sequencing (NGS) of thousands of HPV containing tumor genomes showing, in contrast to all other HPV viral factors including E6, that E7 was strictly devoid of genetic variants in pre-cancer and cancer cases (White E A, Munger K., Crowd Control: E7 Conservation Is the Key to Cancer. Cell. 170:1057-1059 (2017), Mirabello L, et al., HPV16 E7 Genetic Conservation Is Critical to Carcinogenesis, Cell 170:1164-1174 (2017)). E7 has the highest number of associations with cellular protein networks (Farooq Q U A, Shaukat Z, Zhou T, Aiman S, Gong W, Li C. Inferring Virus-Host relationship between HPV and its host *Homo sapiens* using protein interaction network. Sci Rep. 2020 May 26; 10(1):8719. doi: 10.1038/s41598-020-65837-w. PMID: 32457456; PMCID: PMC7251128). Therefore, E7 qualifies as the only non-surrogate target for a therapeutic intervention. In particular this includes the listed E7 proteins from various high-risk HPV types and also from diseases inducing E7 molecules that are defined as low risk. The amino acid sequences according to the Expasy ViralZone database can be extracted from the Sequence Numbers and Identifiers (in parenthesis). From the Alpha-papillomavirus: P03129 (VE7_HPV16); P04020 (VE7_HPV11); P06788 (VE7_HPV18); P17387 (VE7_HPV31); P06429 (VE7_HPV33); P27230 (VE7_HPV35); P24837 (VE7_HPV39); P36829 (VE7_HPV40); P27231 (VE7_HPV42); Q705H9 (Q705H9_HPV43); Q80914 (VE7_HPV44); P21736 (VE7_HPV45); P26558 (VE7_HPV51); P36831 (VE7_HPV52); P36832 (VE7_HPV53); Q81019 (VE7_HPV54); P36833 (VE7_HPV56); P26557 (VE7_HPV58); Q81965 (Q81965_HPV59), Q80956 (VE7_HPV66); P54668 (VE7_HPV68); P50785 (VE7_HPV70); Q9IR58 (Q9IR58_HPV82); Q84292 (VE7_HPV6A); E7 molecules for Beta-papillomavirus contain P06932 (VE7_HPV05); P06430 (VE7_HPV08); Q80908 (VE7_HPV38).

Accordingly, E7 selective small molecule drugs, that cause a rapid decrease of E7 oncoprotein steady state levels, consequently introducing a loss of function at the protein level, are of great interest. This type of active principle is called "degrader". At the molecular level, a degradation of E7 allows to target and resolve all the disease-causing distortions brought about from the expression of E7 oncoproteins. Essentially: tumorigenic dysregulation of the pRB pathway, interference with PI3K and TGF-beta cell signaling and a direct implementation of immunosuppressive conditions for the tumor microenvironment—all fueling into regression of the tumor.

Polyomaviridae as a Degrader-Drug Target for an Unmet Medical Need:

Polyoma virus PyV show high sequence conservation between large/middle T antigen and HPV oncoproteins. Similar to other viral oncoproteins, large and middle T antigens target cellular regulatory factors to favor cell proliferation, immune evasion and downregulation of apoptosis. E7 degraders can show degrader activities for pathologic Lage T molecules. Up to date 14 different PyV were discovered. Various of these human PyV subtypes are of pharmacological interest. MCPyV is the causative agent for the aggressive and deadly Merkel Cell Carcinoma with no cure available. Most of the PyV are opportunistic infections in a broad population. These infections however become of clinical relevance when PyV, were usually the pathological manifestation of infection is a lytic infection, follow reactivation in an immunosuppressed host. These lytic reactivations can be serious or even fatal, as suggested by polyomavirus associated nephropathy (PVAN) and progressive multifocal leukoencephalopathy (PML). For these diseases, antiviral therapies are desperately needed. The increasing use of immunosuppressive therapies will lead to more cases of polyomavirus-induced disease and could create a market for effective therapeutics as a modern site directed therapeutic option for polyomavirus induced pathogenicity. Currently there are no clear therapeutic options available. Therapeutic strategies suggested in the art are small-molecule inhibitors of virus-glycan binding or of T antigen functions, booster immunization if still feasible in anticipation of immunosuppressive regimens to increase antibody levels, or enhancement of cell-mediated immunity in elderly patients, all options mainly for a targeting of viral infection inhibition. Non-structural, virulence factors such as T antigens can be targeted with molecules of the invention.

As an EXAMPLE, for disease relevant polyoma viruses, Merkel Cell Polyoma Virus (MCPyV) was discovered as the causative agent of Merkel cell carcinoma (MCC), an aggressive neuroendocrine skin cancer with high rates of recurrence, metastatic spread and mortality. Primary risk factors for MCC development include immunosuppression, ultraviolet (UV) light exposure and advanced age. Among the 14 human PyV known today, MCPyV is the only one that has been causal associated with cancer in humans. Although it is likely that other polyomavirus subspecies are directly associated with tumor induction and maintenance, data available so far, do not finally allow these conclusions for the time being. In contrast, MCPyV DNA is a) found clonally integrated in the tumor genome of MCC with persistent expression of LTAg and sTAg and b) LTAg isolated from tumors typically contains a truncated form of LTAg that is functionally incapable of supporting viral replication—all signatures for oncogenic transforming capacities of a DNA tumor virus, as learned from high-risk HPV. Recent studies have demonstrated the presence of MCPyV DNA in other types of tumours and in a subset of haematological malignancies, including chronic lymphocytic leukaemia, a rather exciting perspective if confirmed. Preparedness for MCC is increasing and it is tempting to speculate that similar viruses are the ethiologic agent for far more malignancies than is currently anticipated. As another example, BKPyV is an opportunistic pathogen. Generally. BKPyV infection is extremely common world-wide. Sero-epidemiological studies show that overall, >90% of the general adult population have anti-BKPyV IgG antibodies. BKPyV is the causative agent of BKPyV-associated nephropathy (PVAN) in kidney transplant recipients and hemorrhagic cystitis in bone marrow transplant patients. Primary sites for BKPyV replication are the renal and uro-epithelium, resulting in lytic destruction of these cells. Replication of BKPyV has been observed under all combinations of immunosuppression. BKPyV infection is serious complication of immunosuppression as it is recognized as a leading cause of impaired graft function and premature transplant loss. Reducing the net state of immunosuppression is the mainstay of therapy. In contrast to CMV infections which are treated by anti-virals there is no direct antiviral therapy available for BKV, an urgent medical need for immunosuppressed patient populations including any transplant, HIV and elderly people.

As another EXAMPLE, JC Polyomavirus (JCPyV) is very similar to BKPyV in primary amino acid sequence with no serious treatment option in place. JCPyV causes progressive multifocal leukoencephalopathy (PML), a rapidly-progressive and fatal demyelinating disease. JCPyV replicates in oligodendrocytes, leading to progressive accumulation of neurological deficits and ultimately death. JCPyV causes PML in immunocompromised patients, such as patients with HIV/AIDS, hematological malignancies and in patients receiving immunomodulatory medication, such as natalizumab, efalizumab, rituximab, for the treatment of multiple sclerosis, Crohn's disease, lymphoma, severe forms of plaque-type psoriasis and rheumatic diseases. In addition to PML, JCPyV can cause other neurological disorders, such as JCPyV granule cell neuronopathy, JCPyV encephalopathy and meningitis.

As another EXAMPLE, TS Polyomavirus (TSPyV) A similar conservation of primary amino acid sequence is observed in TSPyV which causes the rare skin disease trichodysplasia spinulosa (TS) affecting solid-organ transplant patients undergoing immunosuppressive therapy. The disease is characterized by the development of follicular papules and keratin spines (spicules), predominantly in the face, again with no serious treatment option.

As another EXAMPLE, HPyV7 Polyomavirus A newly discovered polyomavirus subtype HPyV7 was associated with pruritic rash and viremia in lung transplant recipients on immunosuppressive therapy. HPyV7 involvement is reported for thymic-epithelial tumors. Although not clearly confirmed, it is not unlikely that HPyV7, as well as other recently-discovered PyV might be associated with novel pathogenicity in immunocompromised individuals.

Other viruses with similar characteristics suitable for targeting with the molecules of the invention, which show overlapping MOA for virulence and host immune-suppression are for example non-structural proteins of human immunodeficiency virus HIV, Hepatitis C virus HCV, Hepatitis B virus HBV, and in particular of Influenza A virus NS1 proteins of high-risk zoonotic Influenza strains or other orthomyxoviridae viruses.

Corona:

Three highly pathogenic human coronaviruses (HCoVs), including severe acute respiratory syndrome (SARS)-CoV, Middle East respiratory syndrome (MERS)-CoV, and SARS-CoV-2, emerged within the first 20 years of the twenty-first century. The global epidemic of SARS-COV in 2002-2003 revealed for the first time that HCoVs can present a significant global public health threat. The mortality rate of SARS-COV was ~10%, and the epidemic was contained within 2003. MERS-CoV has higher mortality rates (~35%) than SARS-COV and still remains a public health problem. The global pandemic of SARS-CoV-2, which was initially identified late in 2019 in Wuhan, China, is currently in progress. There has been substantial effort worldwide devoted to controlling the SARS-CoV-2 pandemic and the treatment of patients with COVID-19, the disease it causes. Vaccination is in progress but break through mutations represent a global thread and options for therapeutic interventions are wanted.

CoVs are members of the subfamily Coronavirina within the family Coronaviridae and the order Nidovirales. They are classified into four genera, including Alphacoronavirus (α-CoV), Betacoronavirus (β-CoV), Gammacoronavirus (γ-CoV), and Deltacoronavirus (δ-CoV). α- and β-CoVs infect only mammals and γ- and δ-CoVs primarily infect birds, although some γ- and δ-CoVs can also infect mammals. It has been well-recognized that CoVs are major pathogens for livestock, causing substantial economic losses. They also infect mammalian pets, laboratory animals and many other wild animals. All highly pathogenic HCoVs, including SARS-COV, MERS-COV, and SARS-CoV-2, belong to the genus β-CoV and are considered to be initially derived from wild mammals, most probably bats. They are associated with severe lower respiratory tract infections, while other HCoVs, including HCoV-OC43 and HCoV-HKU1, belonging to the genus β-CoV, and HCoV-229E and HCoV-NL63, belonging to the genus α-CoV, cause relatively mild upper respiratory tract infections.

CoVs are enveloped RNA viruses that contain a large (~30 kb) capped and polyadenylated positive-sense and single-stranded RNA genome. The CoV particle comprises at least four canonical structural proteins, including N, S, M, and E proteins. The 5' two-thirds of the genome encodes gene 1 proteins and the one-third at the 3' end encodes structure and accessory proteins. The latter proteins are not required for virus replication in cell cultures. Upon entry into host cells, the CoV genomic RNA, which is released into the cytoplasm, translates two large, partially overlapping precursor polyproteins from gene 1. Two virally encoded proteinases proteolytically process these precursor polyproteins to generate 16 mature proteins, labeled non-structural protein 1 (nsp1) to nsp16 for α- and β-CoVs. All of these gene 1 proteins, except for nsp1 and nsp2, are considered to be essential for viral RNA synthesis. Nsp1, one of the proteins encoded by gene 1, is encoded in only α- and β-CoVs.

As an example, it may be specifically highlighted that the nsp1 of pathogenic CoVs is of particular interest to this invention. Nsp1 is a major virulence factor in several CoVs. Expression of nsp1 of mouse hepatitis virus (MHV), a β-CoV, reduces cellular gene expression. MHV nsp1 acts as an interferon (IFN)-antagonist and is a major virulence factor for mice. A specific amino acid region of MHV nsp1, LLRKxGxKG highly conserved in human pathogenic CoVs is important for the pathogenicity in mice. Like MHV nsp1, SARS-COV nsp1 plays an important role in suppressing antiviral responses, thus representing an ideally suited animal model system for in vivo studies of drug candidates. The amino acid region of SARS-COV nsp1, which corresponds to the LLRKxGxKG region of MHV nsp1, is responsible for pathogenicity in mice and inhibition of host antiviral signaling pathways, suggesting the importance of the region corresponding to the LLRKxGxKG region of MHV nsp1 for virulence of β-CoVs. Distinct but overlapping regions of nsp1, which interact with different host factors, may exert the inhibition of host gene expression and antiviral signaling pathways. Expression of SARS-COV nsp1 and SARS-COV replication enhances signaling through the Calcineurin/NFAT (nuclear factor of activated T cells) pathway, which is important for immune cell activation, and SARS-COV nsp1 expression induced the secretion of several chemokines in human lung epithelial cells, implying a possible role for nsp1 in immune dysregulation.

SARS-COV nsp1 also disrupts the nuclear-cytoplasmic transport of biomolecules. SARS-COV nsp1 associates with Nup93, a member of the nuclear pore complex, and displaces it from the nuclear pore complex. SARS-COV nsp1 expression alters the nuclear-cytoplasmic distribution of nucleolin, which is an RNA-binding protein found primarily in the nucleus. These studies imply that SARS-COV nsp1 affects multiple steps in expression of host genes, including antiviral genes.

Like nsp1 of β-CoVs, nsp1 of α-CoVs serves as an inhibitor of antiviral gene expression. HCoV-229E nsp1 is under the control of the IFN-β- and IFN-stimulated response element. Nsp1 of porcine epidemic diarrhea virus (PEDV) uses multiple mechanisms to suppress host innate immune responses: it interrupts the enhanceosome assembly of IRF3 and CREB-binding protein by degrading the latter protein, resulting in suppression of type I IFN production, it is a potent NF-κB antagonist by inhibiting phosphorylation and subsequent degradation of IκBα, leading to suppression of IFN production and early production of pro-inflammatory cytokines, and it blocks the nuclear translocation of IRF1 and reduces the number of peroxisomes to suppress IRF1-mediated induction of type III IFNs.

For α-CoVs it was shown that a conserved region (amino acids 91-95) of nsp1, which includes also the feline infectious peritonitis virus (FIPV), TGEV, PEDV, HCOV-229E, and HCoV-NL63, is responsible for suppression of host gene expression. Further it was demonstrated that expression of nsp1 of TGEV, porcine respiratory coronavirus (PRCV), swine acute diarrhea syndrome coronavirus (SADS-COV), PEDV, HCOV-229E, or HCoV-NL63 reduces IFN-related gene expression, expression of the nsp1s of the α-CoVs markedly downregulates STAT1 phosphorylation at S727 residue without affecting the STAT1 expression levels and STAT1 phosphorylation at S701, and STAT1, ISG15, and IRF9 mRNAs are significantly upregulated in cells infected with a FIPV mutant carrying a deletion of amino acids 91-95 in the nsp1 without severely affecting virus replication ability. In this context the p70 S6 Kinase pathway is vital, (Petritsch C, Beug H, Balmain A, Oft M. TGF-beta inhibits p70 S6 kinase via protein phosphatase 2A to induce G(1) arrest. Genes Dev. 2000; 14(24):3093-3101. doi:10.1101/gad.854200) well accessible with the molecules of the invention. These data show that nsp1 proteins of α-CoVs also act as major pathogenic determinants like that of β-CoVs.

SARS-COV Nsp1 and SARS-CoV-2 Nsp1 suppress cellular protein translation initiation. SARS-CoV-2 nsp1 has 84% amino acid sequence identity with SARS-COV nsp1 suggesting that both proteins have similar biological functions. SARS-CoV-2 nsp1 binds to 40S and 80S ribosome subunits and disrupts cap-dependent translation. Like SARS-COV nsp1, the K164 and H165 residues close to the C-terminus of SARS-CoV-2 nsp1 are important for ribosome binding and translation inhibition. In addition to inhibiting translation by binding to 40S ribosomes, SARS-COV nsp1 also induces degradation of endogenous host mRNAs in SARS-CoV-infected cell The complex of SARS-COV nsp1-40S ribosome induces the endonucleolytic cleavage by a putative host RNase at the 5' region of capped nonviral mRNAs and renders the mRNA translationally incompetent. In this context, a differential templet dependent cleavage of selected RNAs of SARS-COV nsp1 is observed, for example it induces RNA cleavage within the ribosome loading region of type I and type II picornavirus internal ribosome entry site (IRES) elements, whereas it does not induce RNA cleavage within the IRES elements of hepatitis C virus or cricket paralysis virus. Many SARS-COV nsp1-induced cleavage sites in capped mRNA transcripts are detected within 30 nt of the 5' untranslated region. Along these lines recent studies demonstrated that SARS-COV nsp1, as well as SARS-CoV-2 nsp1 suppresses production of IFN-β and in this context SARS-COV nsp1 suppresses host innate immune responses, including type I IFN expression, in SARS-CoV-infected cells. (*Mechanism of Coronavirus Nsp1-Mediated Control of Host and Viral Gene Expression*. Keishuke Nakagawa and Shinji Makino, Cells, 2021 February; 10(2):300; and also citations therein).

Preferably the compounds of the present invention may be used for the treatment of an infection with HPV.

Further preferably, the compounds of the present invention may be used for the treatment and/or prevention of neoplastic and malign diseases, especially cancer of the cervix, vulva, vagina, anus, penis, head and neck, as well as genital warts, subpopulations of non-melanoma skin cancer, lung-cancer, prostate and breast cancer, recurrent respiratory papillomatosis (RRP), Burkitt lymphoma, non-Hodgkin lymphoma and Bowen's disease.

The compounds according to the present invention are also suitable for use in the prevention or treatment of infection with unicellular eukaryotic parasites, especially with *Plasmodium falciparum, Plasmodium malariae*, and *Leishmania donovani.*

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage may be adjusted to the individual requirements in each particular case including the specific compound being administered, the route of administration, the condition being treated, as well as the patient being treated.

Examples of pharmacologically acceptable salts of sufficiently basic compounds of formula (I) or (II) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound of formula (I) or (II) may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of formula (I) or (II). Compounds of formula (I) or (II) may be solvated, especially hydrated. The hydratization/hydration may occur during the process of production or as a consequence of the hygroscopic nature of the initially water free compounds of formula (I) or (II). The solvates and/or hydrates may e.g. be present in solid or liquid form.

It should be appreciated that certain compounds of formula (I) or (II) may have tautomeric forms from which only one might be specifically mentioned or depicted in the following description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). All these tautomeric forms, geometrical or optical isomers (as well as racemates and diastereomers) and polymorphous forms are included in the invention. Since the compounds of formula (I) or (II) may contain asymmetric C-atoms, they may be present either as achiral compounds, mixtures of diastereomers, mixtures of enantiomers or as optically pure compounds. The present invention comprises both all pure enantiomers and all pure diastereomers, and also the mixtures thereof in any mixing ratio.

The therapeutic use of compounds according to formula (I) or (II), their pharmacologically acceptable salts, solvates and hydrates, respectively, as well as formulations and pharmaceutical compositions also lie within the scope of the present invention.

The pharmaceutical compositions according to the present invention comprise at least one compound of formula (I) or (II) as an active ingredient and, optionally, carrier substances and/or adjuvants.

The present invention also relates to pro-drugs which are composed of a compound of formula (I) or (II) and at least one pharmacologically acceptable protective group which will be cleaved off under physiological conditions, such as an alkoxy, arylalkyloxy-, acyl-, acyloxymethyl group (e.g. pivaloyloxymethyl), an 2-alkyl-, 2-aryl- or 2-arylalkyl-oxycarbonyl-2-alkylidene ethyl group or an acyloxy group as defined herein, e.g. ethoxy, benzyloxy, acetyl or acetyloxy or, especially for a compound of formula (I) or (II), carrying a hydroxy group (—OH): a sulfate, a phosphate ($—OPO_3$ or $—OCH_2OPO_3$) or an ester of an amino acid.

Preferably, the present invention also relates to a prodrug, a biohydrolyzable ester, a biohydrolyzable amide, a polymorph, tautomer, stereoisomer, metabolite, N-oxide, biohydrolyzable carbamate, biohydrolyzable ether, physiologically functional derivative, atropisomer, or in vivo-hydrolysable precursor, diastereomer or mixture of diastereomers, chemically protected form, affinity reagent, complex, chelate and a stereoisomer of the compounds of formula (I) or (II).

As used herein, the term pharmaceutically acceptable ester especially refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

As mentioned above, therapeutically useful agents that contain compounds of formula (I) or (II), their solvates, salts or formulations are also comprised in the scope of the present invention. In general, compounds of formula (I) or (II) will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 10 mg to about 10,000 mg, preferably from about 20 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

The present invention moreover provides a method of degrading E7.

Further the present invention provides a method of treating a HPV infection in a subject in need thereof, the method comprising administering to the subject a therapeutically effective amount of a compound of formula (I) or (II), or a pharmaceutically acceptable salt thereof.

In one embodiment, a method is provided for treating cancer comprising administering to a patient in need thereof, a therapeutically effective amount of a compound of formula (I) or (II) or a salt thereof.

Examples of diseases (e.g. cancers) that may be treated using the methods of the present invention include neoplastic and malign disease, such as cancer of the cervix, vulva, vagina, anus, penis, head and neck, as well as genital warts, subpopulations of non-melanoma skin cancer, lung-cancer, prostate and breast cancer, recurrent respiratory papillomatosis (RRP) and Bowen's disease.

The compounds of the present invention can be synthesized according to procedures described e.g. in: Rothweiler et al. ChemMedChem 2008, 3, 1118-1128; WO 2006/097323 and WO 2008/034039.

According to another aspect, the present invention relates to the use of a compound according to the present invention, especially a compound selected from the group (3R,4R)-N-[3-(4-methylpiperazin-1-yl) phenyl]-2-[(1-methylpiperidin-4-yl) methyl]-1-oxo-3-[4-(trifluoromethyl)phenyl]-1,2,3,4-tetrahydroisoquinoline-4-carboxamide), (3S,4S)-N-[3-(4-methylpiperazin-1-yl) phenyl]-2-[(1-methylpiperidin-4-yl) methyl]-1-oxo-3-[4-(trifluoromethyl)phenyl]-1,2,3,4-tetrahydroisoquinoline-4-carboxamide), (3R,4R)-N-[3-(4-methylpiperazin-1-yl) phenyl]-2-[(4-methylphenyl)methyl]-1-oxo-3-[4-(trifluoromethyl)phenyl]-1,2,3,4-tetrahydroisoquinoline-4-carboxamide) and (3S,4S)-N-[3-(4-methylpiperazin-1-yl) phenyl]-2-[(4-methylphenyl) methyl]-1-oxo-3-[4-(trifluoromethyl)phenyl]-1,2,3,4-tetrahydroisoquinoline-4-carboxamide), for the manufacture of a medicament for the treatment or prevention of an infection with a polyomaviridae virus, an orthomyxoviridae virus, especially Influenza A virus, or an infection with a coronaviridae virus, a human immunodeficiency virus (HIV), a Merkel cell polyomavirus (MCV, MCPyV), a JC polyomavirus (JCV, JCPyV), a BK polyomavirus (BKV, BKPyV), a TS polyomavirus (TSV, TSPyV), a H7 polyomavirus (HV7, HPyV7), a Simian polyomavirus 40 (SV40), a Cytomegalovirus (CMV), a Hepatitis B Virus (HEPB), a Hepatitis C Virus (HEPC), a Hepatitis D Virus (HEPD), a Human immunodeficiency virus 1 (HIV-1), a Human immunodeficiency virus 2 (HIV-2), a Human T-lymphotropic virus I (HTLV-I), a Human T-lymphotropic virus II (HTLV-II), an Epstein Bar Virus (EBV), a Karposi sarcoma-associated herpesvirus (Herpesviridae; KSHV), a Hepatitis C virus (HCV), or a Hepatitis B virus (HBV), especially an HPV infection or a SARS-CoV-2 infection; or (especially as a degrader of protein E7) for the treatment of HPV induced malignant and neoplastic diseases, especially cancer of the cervix, vulva, vagina, anus, penis, head and neck, as well as genital warts, subpopulations of non-melanoma skin cancer, lung-cancer, prostate and breast cancer, recurrent respiratory papillomatosis (RRP), Burkitt lymphoma, non-Hodgkin lymphoma and Bowen's disease; or for use in the prevention or treatment of infection with unicellular eukaryotic parasites, especially with *Plasmodium falciparum, Plasmodium malariae*, and *Leishmania donovani*.

According to another aspect, the present invention relates to a method of treatment or prevention of an infection with a polyomaviridae virus, an orthomyxoviridae virus, especially Influenza A virus, or an infection with a coronaviridae virus, a human immunodeficiency virus (HIV), a Merkel cell polyomavirus (MCV, MCPyV), a JC polyomavirus (JCV, JCPyV), a BK polyomavirus (BKV, BKPyV), a TS polyomavirus (TSV, TSPyV), a H7 polyomavirus (HV7, HPyV7), a Simian polyomavirus 40 (SV40), a Cytomegalovirus (CMV), a Hepatitis B Virus (HEPB), a Hepatitis C Virus (HEPC), a Hepatitis D Virus (HEPD), a Human immunodeficiency virus 1 (HIV-1), a Human immunodeficiency virus 2 (HIV-2), a Human T-lymphotropic virus I (HTLV-I), a Human T-lymphotropic virus II (HTLV-II), an Epstein Bar Virus (EBV), a Karposi sarcoma-associated herpesvirus (Herpesviridae; KSHV), a Hepatitis C virus (HCV), or a Hepatitis B virus (HBV), especially an HPV infection or a SARS-CoV-2 infection; or (especially as a degrader of protein E7) for the treatment and prevention of HPV induced malignant and neoplastic diseases, especially cancer of the cervix, vulva, vagina, anus, penis, head and neck, as well as genital warts, subpopulations of non-melanoma skin cancer, lung-cancer, prostate and breast cancer, recurrent respiratory papillomatosis (RRP), Burkitt lymphoma, non-Hodgkin lymphoma and Bowen's disease; or for use in the prevention or treatment of infection with unicellular eukaryotic parasites, especially with *Plasmodium falciparum, Plasmodium malariae*, and *Leishmania donovani*, wherein an effective amount of a compound according to the present invention, especially a compound selected from the group (3R,4R)-N-[3-(4-methylpiperazin-1-yl) phenyl]-2-[(1-methylpiperidin-4-yl)methyl]-1-oxo-3-[4-(trifluoromethyl)phenyl]-1,2,3,4-tetrahydroisoquinoline-4-carboxamide), (3S,4S)-N-[3-(4-methylpiperazin-1-yl) phenyl]-2-[(1-methylpiperidin-4-yl) methyl]-1-oxo-3-[4-(trifluoromethyl)phenyl]-1,2,3,4-tetrahydroisoquinoline-4-carboxamide), 3R,4R)-N-[3-(4-methylpiperazin-1-yl) phenyl]-2-[(4-methylphenyl) methyl]-1-oxo-3-[4-(trifluoromethyl)phenyl]-1,2,3,4-tetrahydroisoquinoline-4-carboxamide) and (3S,4S)-N-[3-(4-methylpiperazin-1-yl) phenyl]-2-[(4-methylphenyl)methyl]-1-oxo-3-[4-(trifluoromethyl)phenyl]-1,2,3,4-tetrahydroisoquinoline-4-carboxamide), is administered to a patient in need thereof.

According to another aspect, the present invention relates to a pharmaceutical composition comprising a combination of a signaling molecule antagonist or agonist and a compound according to the present invention, especially a compound selected from the group (3R,4R)-N-[3-(4-methylpiperazin-1-yl) phenyl]-2-[(1-methylpiperidin-4-yl)methyl]-1-oxo-3-[4-(trifluoromethyl)phenyl]-1,2,3,4-tetrahydroisoquinoline-4-carboxamide), (3S,4S)-N-[3-(4-methylpiperazin-1-yl) phenyl]-2-[(1-methylpiperidin-4-yl) methyl]-1-oxo-3-[4-(trifluoromethyl)phenyl]-1,2,3,4-tetrahydroisoquinoline-4-carboxamide), 3R,4R)-N-[3-(4- methylpiperazin-1-yl) phenyl]-2-[(4-methylphenyl) methyl]-1-oxo-3-[4-(trifluoromethyl)phenyl]-1,2,3,4-tetrahydroisoquinoline-4-carboxamide) and (3S,4S)-N-[3-(4-methylpiperazin-1-yl) phenyl]-2-[(4-methylphenyl)methyl]-1-oxo-3-[4-(trifluoromethyl)phenyl]-1,2,3,4-tetrahydroisoquinoline-4-carboxamide), or a pharmaceutically acceptable hydrate, solvate or salt thereof, optionally in combination with a pharmaceutically acceptable carrier. The signaling molecule is preferably a receptor molecule or one or more of its downstream target, such as, EGFR, Ras, Phosphatidylinositol-4,5-bisphosphate 3-kinase alpha 85 kDa regulatory subunit or 110 kDa catalytic subunit (PI3K), Phosphatase and tensin homolog (PTEN), Protein kinase B (PKB, Akt), p70-S6 Kinase 1, mammalian target of rapamycin (mTOR1), FK506-binding protein (FKBP12), mTOR Complex 1 (mTORC1), TGFbeta pathway signaling, and/or NOTCH signaling. Specifically preferred signaling molecules are a steroid receptor molecule for estrogen or a signaling molecule antagonist or agonist selected from the group of (as mTOR, Pi3 and Akt agonists/antagonists) mTOR inhibitor-8 (CAS No.: 2489196-70-3), mTOR inhibitor-3 (CAS No.: 1207358-59-5), mTOR inhibitor-1 (CAS No.: 468747-17-3), mTOR inhibitor-2 (CAS No.: 2219323-96-1), HDACs/mTOR Inhibitor 1 (CAS No.: 2271413-06-8), PI3K/mTOR Inhibitor-3 (CAS No.: 1363338-53-7), PI3K/mTOR Inhibitor-2 (CAS No.: 1848242-58-9), PI3K/mTOR Inhibitor-1 (CAS No.: 1949802-49-6), MTI-31 (CAS No.: 1567915-38-1), Sapanisertib (CAS No.: 1224844-38-5), WAY-600 (CAS No.: 1062159-35-6), Onatasertib (CAS No.: 1228013-30-6), MHY1485 (CAS No.: 326914-06-1), PI3Ka/mTOR-IN-1 (CAS No.: 1013098-90-2), PF-04979064 (CAS No.: 1220699-06-8), 3BDO (CAS No.: 890405-51-3), Dihydromyricetin (CAS No.: 27200-12-0), RapaLink-1 (CAS No.: 1887095-82-0), AD80 (CAS No.: 1384071-99-1), DS-7423 (CAS No.: 1222104-37-1), ETP-46464 (CAS No.: 1345675-02-6), Torin 2 (CAS No.: 1223001-51-1), PF-04691502 (CAS No.: 1013101-36-4), TFEB activator 1 (CAS No.: 39777-61-2), Vistusertib (CAS No.: 1009298-59-2), MHY-1685 (CAS No.: 27406-31-1), MCX 28 (CAS No.: 1414453-58-9), CZ415 (CAS No.: 1429639-50-8), XL388 (CAS No.: 1251156-08-7), GNE-317 (CAS No.: 1394076-92-6), NSC781406 (CAS No.: 1676893-24-5), GDC-0349 (CAS No.: 1207360-89-1), Gedatolisib (CAS No.: 1197160-78-3), Compound 401 (CAS No.: 168425-64-7), Temsirolimus (CAS No.: 162635-04-3), 28-Epirapamycin (CAS No.: 253431-35-5), GNE-477 (CAS No.: 1032754-81-6), Ridaforolimus (CAS No.: 572924-54-0), GNE-493 (CAS No.: 1033735-94-2), Bimiralisib (CAS No.: 1225037-39-7), (+)-Usnic acid (CAS No.: 7562-61-0), PP121 (CAS No.: 1092788-83-4), 42-(2-Tetrazolyl)rapamycin (CAS No.: 221877-56-1), AZD-8055 (CAS No.: 1009298-09-2), Torin 1 (CAS No.: 1222998-36-8), PKI-402 (CAS No.: 1173204-81-3), PKI-402 (CAS No.: 1173204-81-3), Chrysophanol (CAS No.: 481-74-3), VS-5584 (CAS No.: 1246560-33-7), Dactolisib (CAS No.: 915019-65-7), PI3K-IN-22 (CAS No.: 1202884-94-3), Torkinib (CAS No.: 1092351-67-1), Zeylenone (CAS No.: 193410-84-3), CC-115 (CAS No.: 1300118-55-1), Rapamycin (CAS No.: 53123-88-9), Salidroside (CAS No.: 10338-51-9), PQR626 (CAS No.: 1927857-98-4), Dactolisib Tosylate (CAS No.: 1028385-32-1), LAT1-IN-1 (CAS No.: 20448-79-7), GSK1059615 (CAS No.: 958852-01-2), Rubioncolin (C CAS No.: 132242-52-5), KU-57788 (CAS No.: 503468-95-9), Apitolisib (CAS No.: 1032754-93-0), Everolimus (CAS No.: 159351-69-6), WYE-687 (CAS No.: 1062161-90-3), SF2523 (CAS No.: 1174428-47-7), WYE-132 (CAS No.: 1144068-46-1), Lupiwighteone (CAS No.: 104691-86-3), OSI-027 (CAS No.: 936890-98-1), JR-AB2-011 (CAS No.: 2411853-34-2), SAR405 CAS No.: 1523406-39-4), WYE-687 dihydrochloride (CAS No.: 1702364-87-1), PI3Ka-IN-5 (CAS No.: 2237953-19-2), PQR530 (CAS No.: 1927857-61-1), PKI-179 (CAS No.: 1197160-28-3), WYE-354 (CAS No.: 1062169-56-5), BGT226 maleate (CAS No.: 1245537-68-1), AKT-IN-10 (CAS No.: 2709045-56-5), BGT226 (CAS No.: 915020-55-2), AKT-IN-9 (CAS No.: 2709045-53-2), PI-103 (CAS No.: 371935-74-9), Voxtalisib (CAS No.: 934493-76-2), ETP-45658 (CAS No.: 1198357-79-7), PF-06843195 (CAS No.: 2067281-51-8), (32-Carbonyl)-RMC-5552 (CAS No.: 2382768-55-8), BC-LI-0186 (CAS No.: 695207-56-8); and (as PDK, PDK1, AKT inhibitors) P7 (CAS No.: 1001409-50-2), BX-320 (CAS No.: 702676-93-5), BX-517 (CAS No.: 850717-64-5), BX517 (CAS No.: 850717-64-5), BX795 (CAS No.: 702675-74-9), BX-912 (CAS No.: 702674-56-4), JX06 (CAS No.: 729-46-4), Polyphyllin I (CAS No.: 50773-41-6), PS10 (CAS No.: 1564265-82-2), PS210 (CAS No.: 1221962-86-2), PS423 (CAS No.: 1221964-37-9), PDK1-IN-RS2 (CAS No.: 1643958-89-7), GSK2334470 (CAS No.: 1227911-45-6), PF-AKT400 (CAS. Nr.: 1004990-28-6), Capivasertib (CAS. Nr.: 1143532-39-1), Afuresertib (CAS. Nr.: 1047644-62-1), Borussertib (CAS. Nr.: 1800070-77-2), GSK-690693 (CAS. Nr.: 937174-76-0), AKT-IN-10 (CAS. Nr.: 2709045-56-5), AKT-IN-9 (CAS. Nr.: 2709045-53-2), AKT-IN-3 (CAS. Nr.: 237 4740-21-1), Vevorisertib (CAS. Nr.: 1416775-46-6), FPA-124 (CAS. Nr.: 902779-59-3), CCT128930 (CAS. Nr.: 885499-61-6), AT13148 (CAS. Nr.: 1056901-62-2).

The invention is further described by the examples and the figures, yet without being limited thereto.

FIG. 1: Cytofluorimetric (CF) analysis used to detect the level of E7 protein expression in the presence of compounds of the invention used to screen for E7 degraders. The E7 protein steady state level reduction in CaSki cells in the presence of a) Cycloheximide (CHX) as a nonspecific positive control for 100% degradation or b) OC246 compounds for 2.5 hours, was analyzed by Flow Cytometry using the intracellular antibody labeling procedure for monoclonal antibodies to HPV E7. E7 signal intensities obtained from FL1 histograms were used to analyze at logarithmic scale the intensity of E7 without treatment (histograms to the right) or treatment (histograms to the left). The FL1 single histogram graph represents the variation in the mean fluorescence intensity (MFI) channel as described in the Methods 1-4. This read out can be used to screen chemical libraries in medium to high throughput format.

FIG. 2: Compounds of the invention induce cell cycle stop and eventually apoptosis as analyzed with HPV containing CaSki tumor cells by Flow cytometry and propidium iodide staining for DNA. Logarithmic scale histograms are shown. A) cells not treated show a regular cell cycle distribution into G1 (left peak) and G2/M phase (right peak). B) cells treated with OC246 show a sub G1 content after 24 hours and C) after 48 hours, indicative for DNA degradation as a measure of apoptosis induction.

Figure 3E:
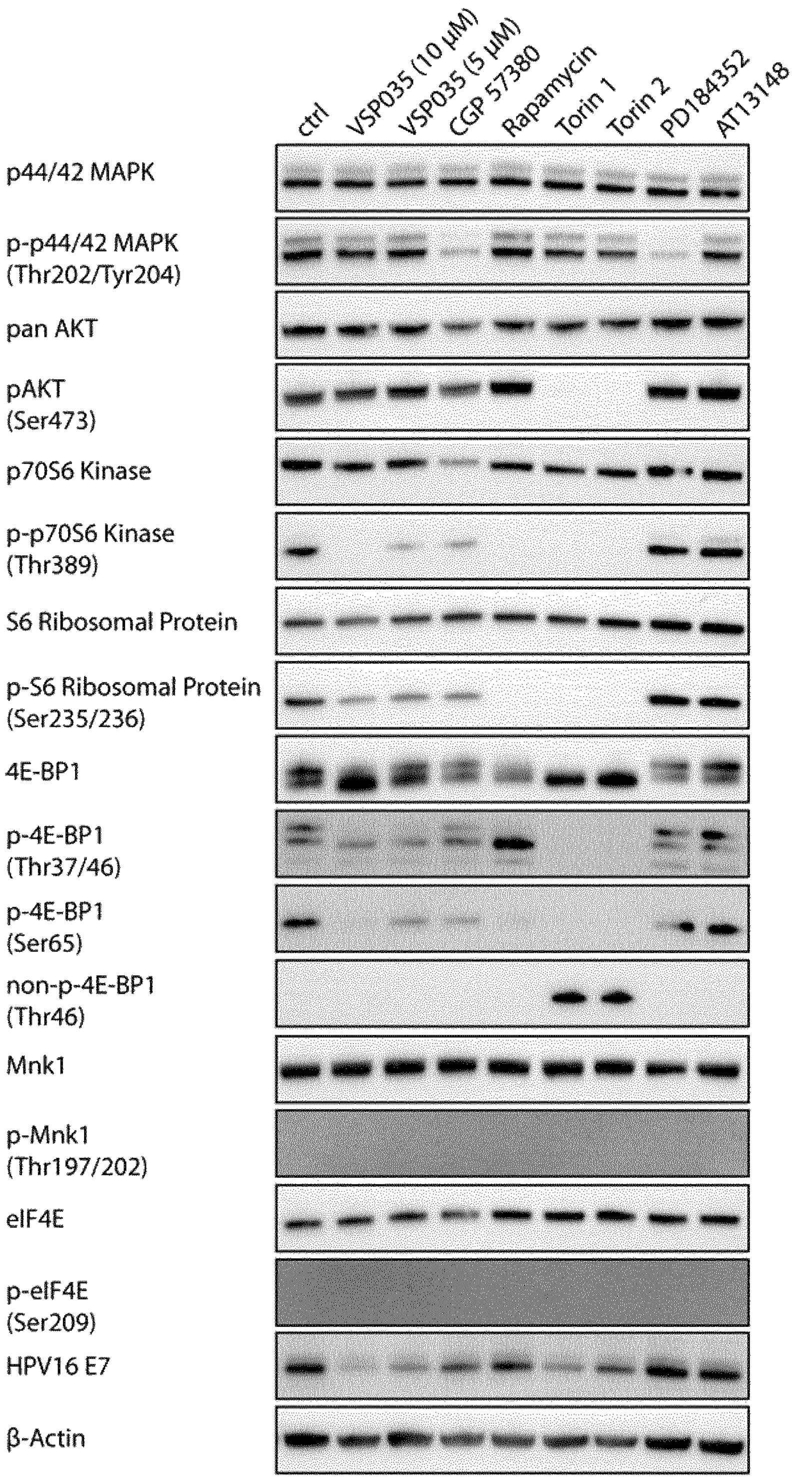

FIG. 3: Steady state levels assessed by western blots using A) E7 specific antibodies of HPV 16 E7 in CaSki cells incubated with VSP035 (VS035) for the indicated time points. Beta-actin staining served as a loading control. B) comparison of E7 staining with different markers for signaling indicating sharp increase of the tumor-suppressor PTPN14 a known direct downstream target of E7 degradation activity and the tumor-suppressor TP53, a known indirect target of E7 via E6/p53 regulation, and no change in Akt or Akt phosphorylation (T473), IRF3 or IRF3 (S386) phosphorylation, NLRX1 and STING steady state protein levels in the presence of VSP035 for the periods indicated, there is a decrease in PDL-1 non glycosylated, with a multiband pattern indicative for the different glycosylation sates with the lowest band known as the non-glycosylated, nascent form, showing time dependent decreasing abundance in the presence of VSP035. This shows that known targets of E7 react on degradation of E7 by VSP035 and tumor-suppressors are reactivated important for therapeutic efficacy and correlating with the apoptosis pattern detected in FIGS. 2 B and C. FIG. 3C shows different exposures of an E7 stain after treatment of cells for the indicated timepoints with VSP035 and wash out of the compound and recovery-phase of 6 hours left, and 24 hours, indicating a robust stability of the compounds after entry into the cells; FIG. 3D: Comparison of the effects induced by OC974 and its enantiomers VSP034 and VSP035 and the mTOR1 inhibitor Rapamycin and mTOR1/2 inhibitor Torin1 on various signaling markers. Whereas the compounds of the invention show similar downstream regulation, albeit weaker influence on translation initiation then mTOR1 inhibitor Rapamycin with a stronger degradation of E7, but nevertheless strong regulation of the phosphorylation of p70 S6 Kinase (T389), the pattern obtained by a mTOR1/2 inhibitor is overlapping but not identical, given the mTOR2 selective pattern is not reflected; FIG. 3E: Various inhibitors were assessed on the influence on E7 steady state level of VSP025 and in comparison to MAP Kinase and PI3K/mTOR Kinase signaling pathway inhibitors, whereas the MAPK pathway showed only minor influence PI3K/mTOR Kinase signaling confirmed the interaction observed from FIGS. 3C,D. Inhibitors were for MEK kinase PD184352 (CI-1040), CGP57380 for MNK kinase, AT13148 for Akt1 and p70S6kinase, Torin 1 and Torin2 for mTOR1 and mTOR2 kinase. Again, VSP035 is the strongest E7 degrader however is generally weaker in translation initiation regulation and strong in p70S6 kinase phosphorylation inhibition suggesting for effective combinations for the inhibition of HPV E7.

Figure 4:
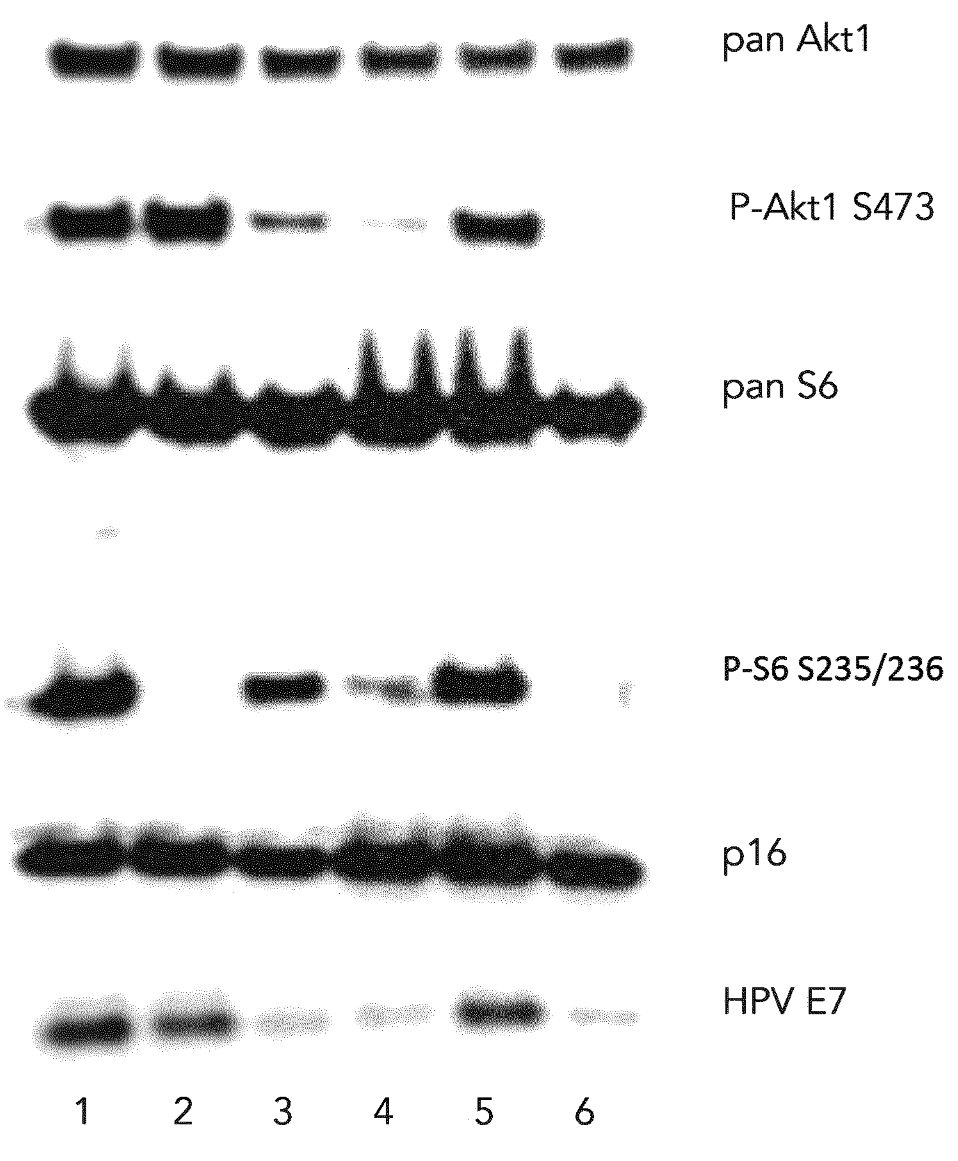

FIG. 4: The effect of PI3Kinase pathway inhibitors on E7 steady state level is assessed. Extracts from CaSki, (HPV+) cells were analyzed in western blots after incubation of the growing cells for 4 hours with vehicle (1), 100 nM Rapamycin (2), 10 μM Akt1 VIII inhibitor (3), 2 μM GSK3 IX inhibitor+10 μM Akt1 VIII inhibitor (4), 2 μM GSK3 IX Inhibitor (5), 0.5 μM PI103+0.1 μM Wortmanin PI3KCA inhibitor (6); staining was with HPV16E, panS6 ribosomal protein, anti-phosphor specific S6 ribosomal protein Serine 235/236, anti-phosphor specific Akt1 Serine 473 and pan Akt1 specific monoclonal antibodies. This western blot experiment shows, that the presence of Rapamycin, PI3KCA and Akt1 inhibitors lead to a robust diminution in the steady state level of the E7 proteins in CaSki cells.

Figure 5:
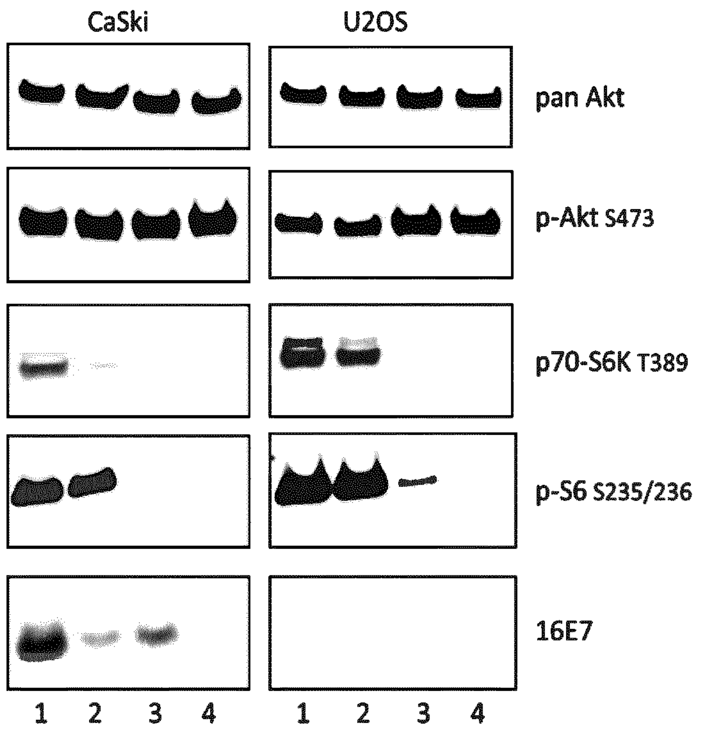

FIG. 5: Comparison of HPV containing cancer cells with HPV negative cancer cells. Cellular extracts from CaSki, (HPV+) and Osteosarcoma cells (U2Os, HPV−) were analyzed in western blots after incubation for 4 hours with vehicle (1), 10 μM OC246, (2) or 100 nM Rapamycine (3) and 10 μM OC246 and 100 nM Rapamycine (4) staining was with P70-S6K(T389); panAkt, Akt(p473); pS6 S235/236 and HPV16E7 antibody detection. This test shows that OC246 does not inhibit signaling of phosphor-Akt S473 as this site is stable phosphorylated in HPV E7 and dominant active PIK3CA-E545K(p110a) containing CaSki cells, nor in PIK3CA WT U2OS cells. Moreover of p70 S6 kinase, phosphor-p70-S6K T389 is de-phosphorylated in response to E7 degradation and to a much lower extend in cells not containing HPV E7 proteins.

Figure 6:
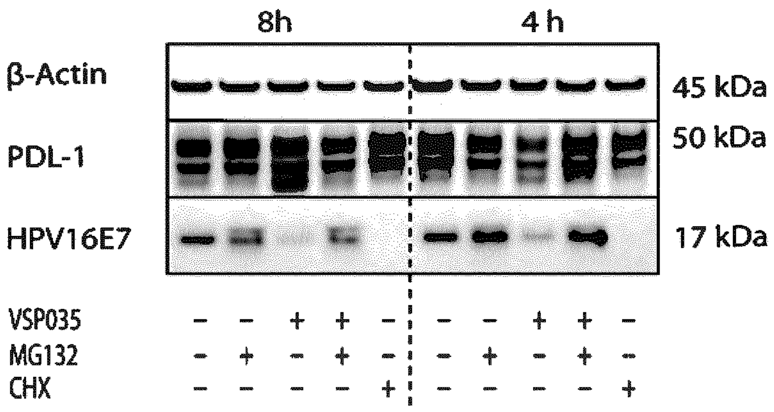

FIG. 6: Compounds of the invention regulate tumor immune-suppressor PDL-1. cell extracts from CaSki, (HPV+) cells were analyzed in western blots and stained with monoclonal antibodies to PDL-1 (GLY-PDL-1 represents the glycosylated population of PDL-1). $1.5\times10^5$ CaSki cells, a cell-line that shows high level of PDL-1 expression, were seeded in 2 ml rpmi 1640+10% fcs in 6-well plates and incubated at 37° c. to allow for cell growth. 24 h after seeding, cells were treated with vsp035, cycloheximide (CHX) and/or MG132 proteasome inhibitor as indicated. Cells were harvested for analysis for by WB. The results show a strong regulation towards faster migrating, posttranslational modified bands in a dose dependent manner, which was more expressed after 8 hours as compared to the 4-hour time-point. Faster migrating band abundancy was regulated by proteasome inhibitor MG132 and the protein was destabilized in the presence of CHX. this demonstrates that E7 stabilizes PDL-1 and the E7 degrader VSP035 reverses these effects making it a valid PDL-1 destabilizer.

FIG. 7: The compounds of the invention induce degradation of HPV E7 from HPV+ SiHa tumor cells which causes the stabilization of the protein levels of the well-established E7 target tumor suppressor retinoblastoma protein, a transcription repressor for which it is well known in the art, that E7 changes its steady state. Cell extracts from SiHa, (HPV+) cells were analyzed in western blots after incubation for 24 hours with vehicle (0), or 10 μM OC246 for 12 and 24 hours; blots were stained with monoclonal antibodies to HPV16E7, Actin and the Retinoblastoma Protein pRb1; an increase of Rb protein signals can be detected with decreasing E7 signal.

FIG. 8: HPV16E7 abundance after incubation for 4, 8, and 12 hours respectively with CHX (cycloheximid), OC974 and various chemotherapeutics. Extracts from CaSki, (HPV+) cells were analyzed in western blots and stained with HPV16E7 and p53 (DO1) specific monoclonal antibodies: vehicle (lanes 1, 14), CHX_Cycloheximide, (lanes 2, 3, 4) OC974 (5, 6, 7), CDDP_Cisplatin (8, 9, 10), DOX-_Doxorubicin (11, 12, 13). This shows that the degradation of E7 seen with the compounds of the invention is not an α-specific effect seen also with standard of care chemotherapeutics, but is rather an intrinsic property of these compounds. Given that E7 is strongly considered a causative, addicted oncogene for HPV induced malignancies a strong advantage as a tumor therapeutic for HPV+ Tumors.

FIG. 9: SARV-CoV-2 anti-viral activity of VSP035 from mono-treatment, or in combination with various pharmacological drug substances at various concentrations shown by the bars from left to the right. Y axis % Inhibition. Due to lethal concentrations for Vero E6 cells, dose dependency is visible at non-lethal doses only (median of multiple experiments n4 is shown); Concentrations (left to right) Compounds and respective assay concentrations in UM are, "constant" means same concentration for the series (X axis, numbers for series).

FIG. 10: Robust antiviral activities was demonstrated for VS035 as single agent and dose dependency over a broad range of very active synergistic drug combinations with VSP035 is demonstrated.

(1) VSP035 (10, 5, 2.5, 1.25, 0.625);
(2) Rapamycin (0.250, 0.125, 0.0625, 0.03125, 0.15625);
(3) VSP035 (constant 10), Rapamycin (0.250, 0.125, 0.0625, 0.03125, 0.15625);
(4) VSP035 (10, 5, 2.5, 1.25, 0.625), Rapamycin (constant 0.0625);
(5) CI-1040 (0.250, 0.125, 0.0625, 0.03125, 0.15625);

(6) VSP035 (constant 10), CI-1040 (0.250, 0.125, 0.0625, 0.03125, 0.15625);

(7) CGP57380 (0.250, 0.125, 0.0625, 0.03125, 0.15625);

(8) VSP035 (constant 10), CGP57380 (0.250, 0.125, 0.0625, 0.03125, 0.15625);

(9) VSP035 (10, 5, 2.5, 1.25, 0.625), CGP57380 (constant 0.250);

(10) Torin-1(0.250, 0.125, 0.0625, 0.03125, 0.15625);

(11) VSP035 (constant 10), Torin-1(0.250, 0.125, 0.0625, 0.03125, 0.15625);

(12) VSP035 (10, 5, 2.5, 1.25, 0.625), Torin-1 (constant 0.0625);

These data show that the moderate SARS-COV2 antiviral activity observed with VSP035 monotherapy is dramatically increased in combination studies with various inhibitors and in particular with mTOR1 inhibitors which brings about a robust, dose dependent inhibition of SARS-COV2 virus

EXAMPLES

Example 1 (Synthesis of OC 974)

Trans-2-[(1-methylpiperidin-4-yl)methyl]-1-oxo-3-[4-(trifluoromethyl)phenyl]-3,4-dihydroisoquinoline-4-carboxylic acid (Acid 1)

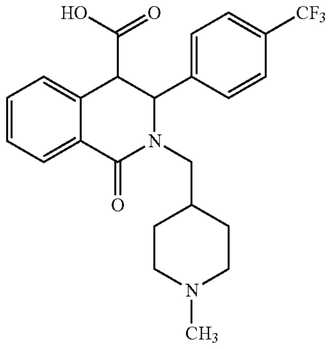 [SMILES: CN1CCC(CN2C(=O)c3ccccc3C(C(=O)O)C2c2ccc(C(F)(F)F)cc2)CC1]

1-(1-methylpiperidin-4-yl)-methanamine (622 mg, 3.57 mmol) was added to a solution of 4-trifluoromethyl-benzaldehyde (527 mg, 3.75 mmol) in 10 ml $CH_2Cl_2$ (peptide grade). The mixture was stirred in a round-bottom flask at room temperature for 1 h. Homophthalic acid (578.8 mg, 3.57 mmol) was then added, the reaction turned orange, and the mixture was stirred under reflux for 1 h. After cooling the mixture to room temperature, the formed precipitate was isolated by filtration and washed several times with $CH_2Cl_2$. The resulting white solid (0.557 g, 1.249 mmol) is a cis/trans mixture of the desired product in a 1:2 ratio. Afterwards, the isomeric mixture was treated with 40 ml acetic acid under reflux for 20 h. After evaporation of the solvent, the yellow residue was washed with 20 ml $Et_2O$ to yield a white solid (0.45 g, 28% yield). MW 446.47. [M+]=446.

Formula: $C_{24}H_{25}F_3N_2O_3$ Composition: C (64.57%), H (5.64%), F (12.77%), N (6.27%), O (10.75%)

(3R,4R)- and (3S,4S)-N-[3-(4-methylpiperazin-1-yl)phenyl]-2-[(1-methylpiperidin-4-yl)methyl]-1-oxo-3-[4-(trifluoromethyl)phenyl]-3,4-dihydroisoquinoline-4-carboxamide (OC974): VSP034 (3R,4R)-; VSP035 (3S,4S)

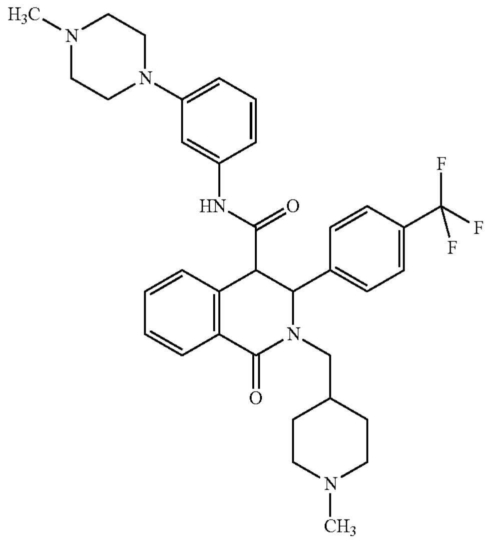 [SMILES: CN1CCC(CN2C(=O)c3ccccc3C(C(=O)Nc3cccc(N4CCN(C)CC4)c3)C2c2ccc(C(F)(F)F)cc2)CC1]

The coupling agent 1-ethyl-3-[3-(dimethylamino)propyl]-carbodiimide·HCl (EDCl, 881.8 mg, 4.6 mmol) was added to a solution of Acid 1 (1 g, 2.3 mmol) in 10 ml dry N,N-dimethylformamide (DMF). The mixture was stirred in a round-bottom flask at room temperature for 10 min.

3-(4-methylpiperazin-1-yl)aniline (880 mg, 4.6 mmol) was then added, and the mixture was stirred overnight at 50° C. Afterwards, EtOAc (60 mL) was added, and the organic layer was washed two times with 40 ml brine, dried over $MgSO_4$, and the solvent was removed under vacuum. Finally, the crude product was purified by chromatography on silica gel with EtOAc/hexanes 4:1 as the eluent to afford the desired product as a white solid (450 mg, 32% yield); MW 619,733; [M+]=619.0

$C_{35}H_{40}F_3N_5O_2$ Composition: C (67.83%), H (6.51%), F (9.2%), N (11.3%), O (5.16%)

Example 2A (Synthesis of Further Compounds)

The following compounds were prepared according to the procedures described above or according to procedures described e.g. in: Rothweiler et al. ChemMedChem 2008, 3, 1118-1128; WO 2006/097323 and WO 2008/034039, using appropriate starting materials:

-continued
OC 969
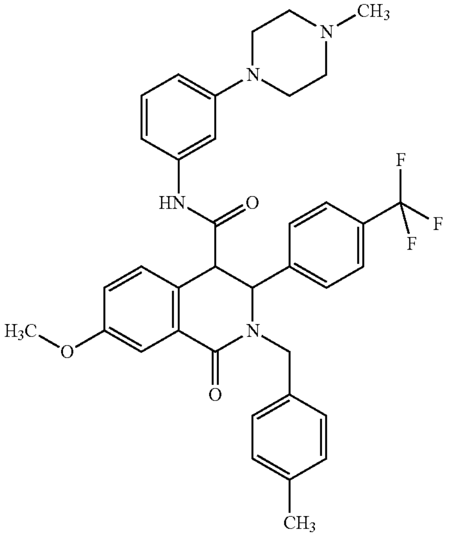
OC 976
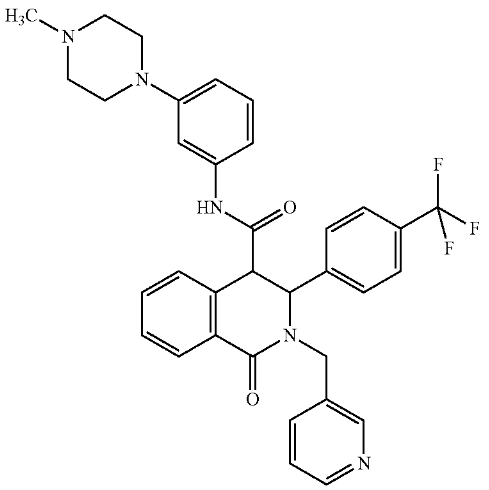
OC 975
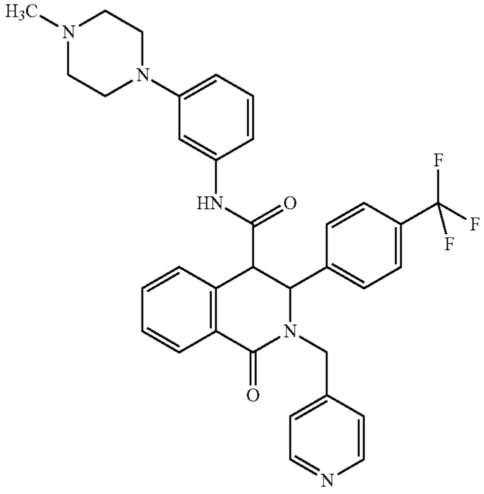
OC 245
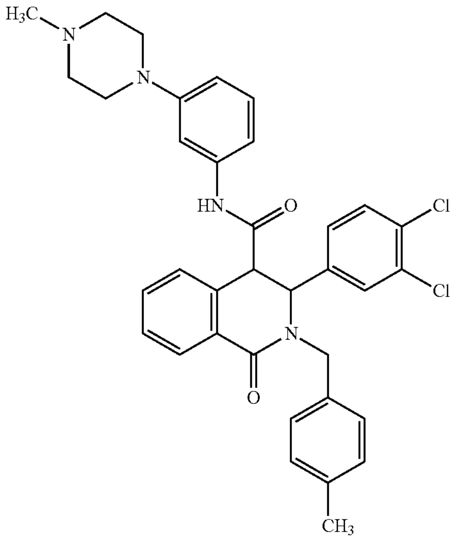
OC 246
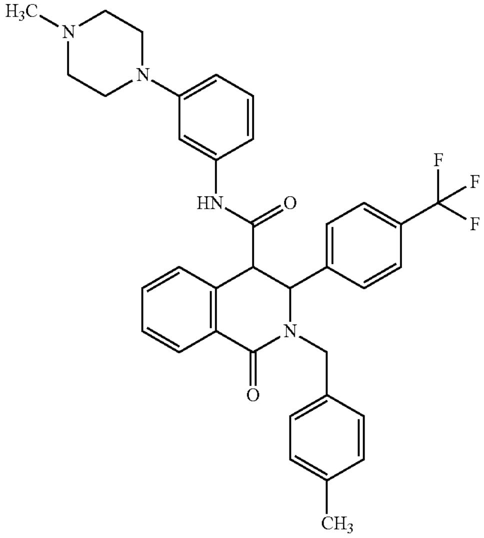
OC 247
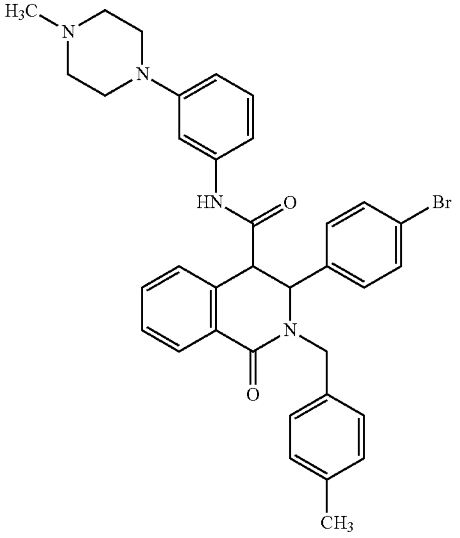

-continued
OC 968
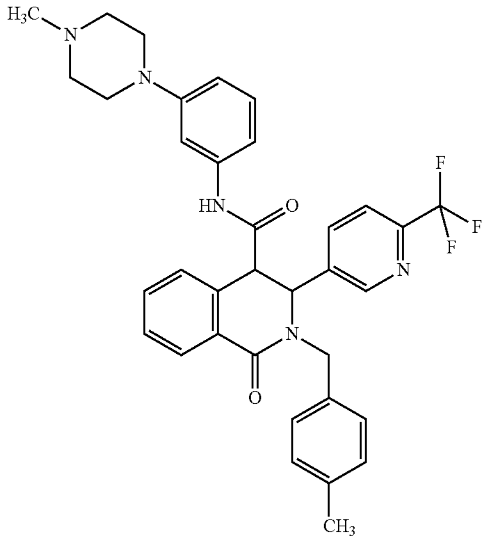
OC 972
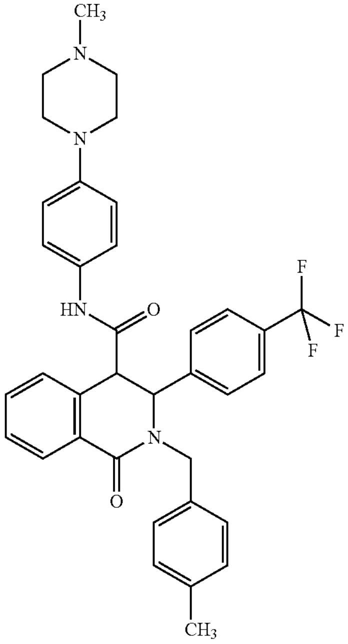
-continued
OC 973
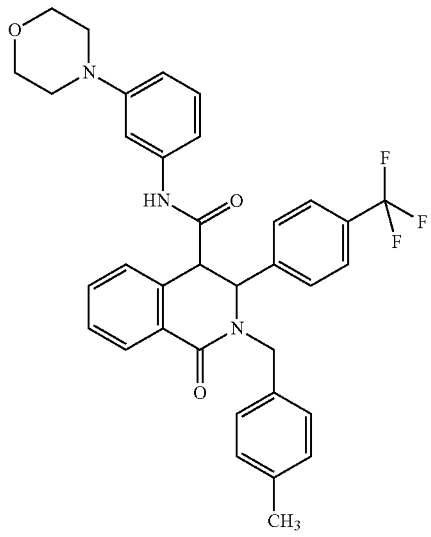
OC 970
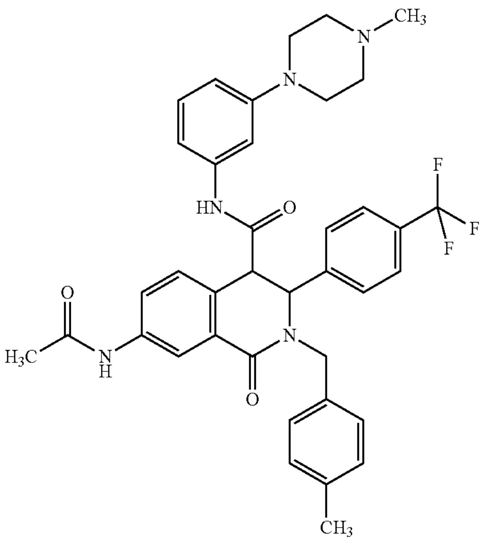
OC 971
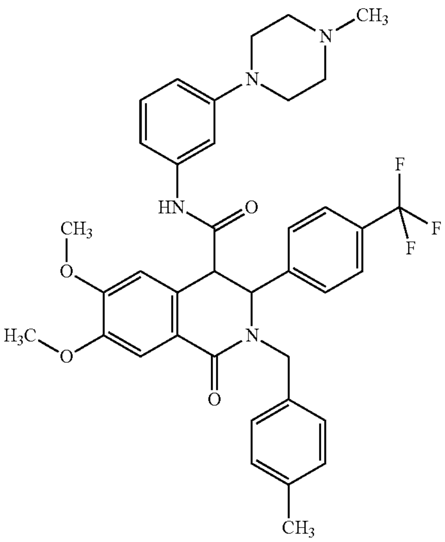

-continued
OC 379
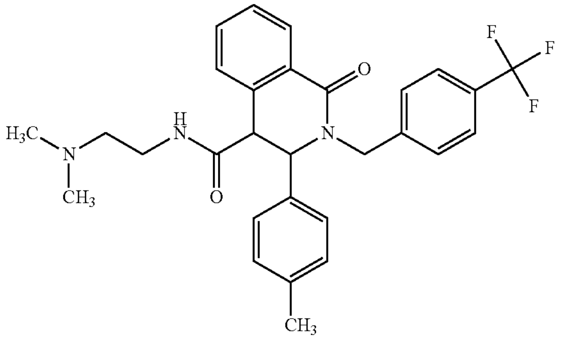
OC 258
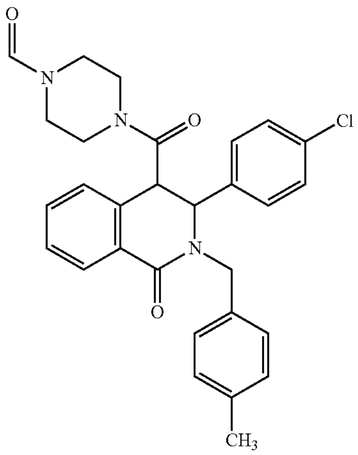
OC 255
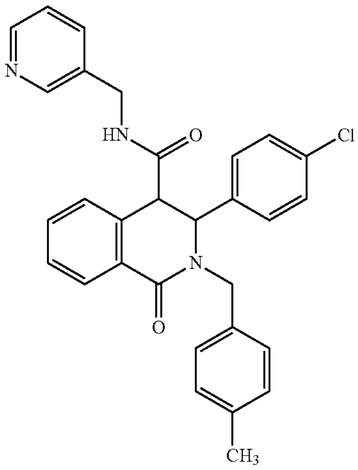
-continued
OC 252
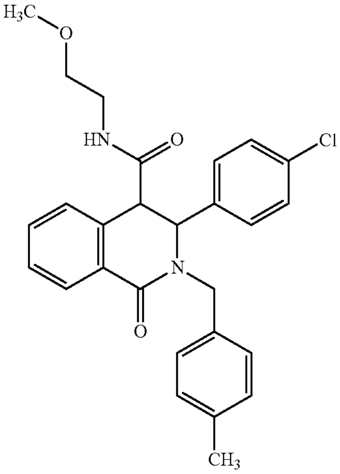
OC 257
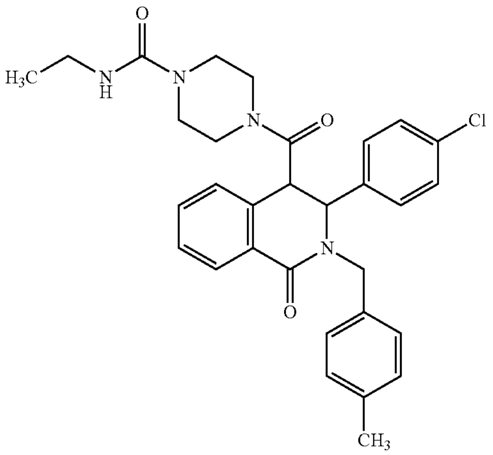
OC 254
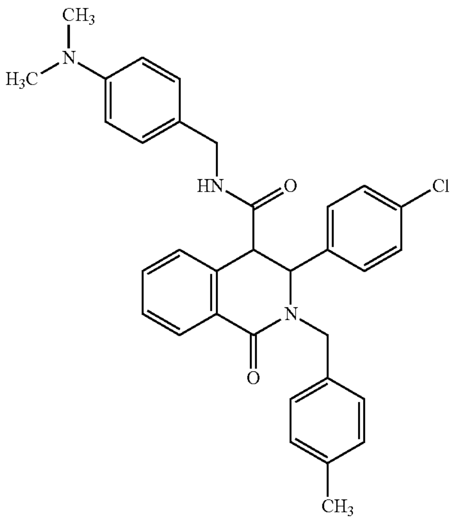

-continued
OC 251
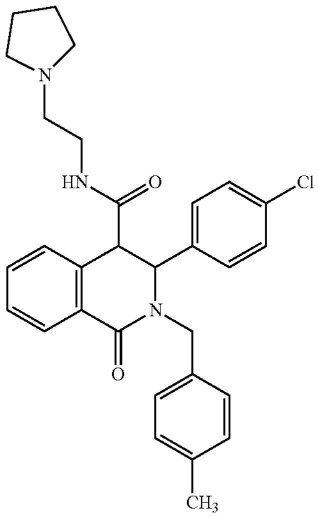
OC 256
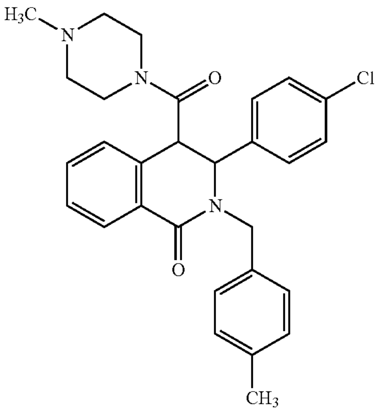
OC 253
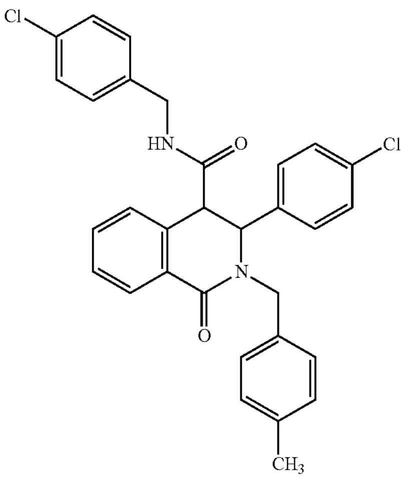
-continued
OC 250
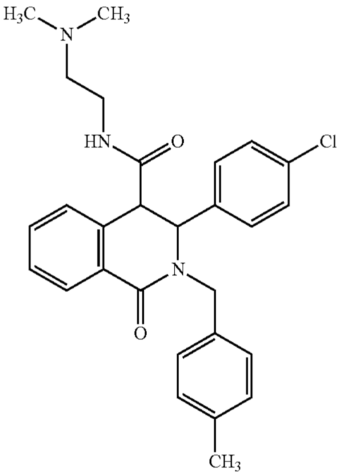
OC 377
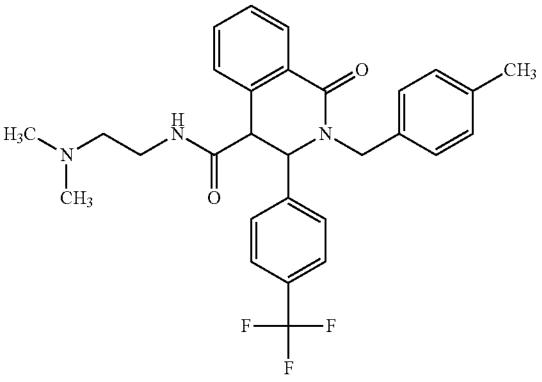
OC 378
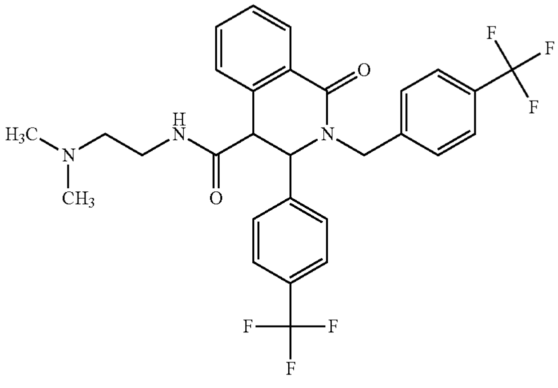

-continued
OC 382
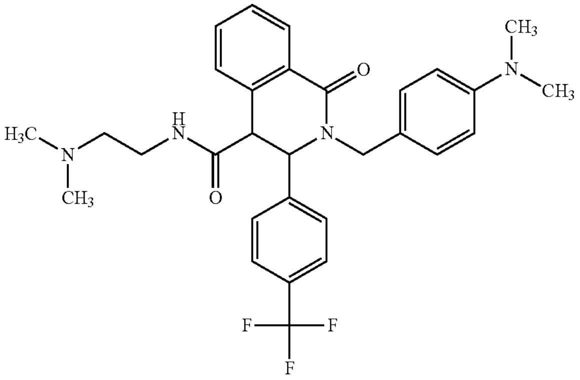
OC 380
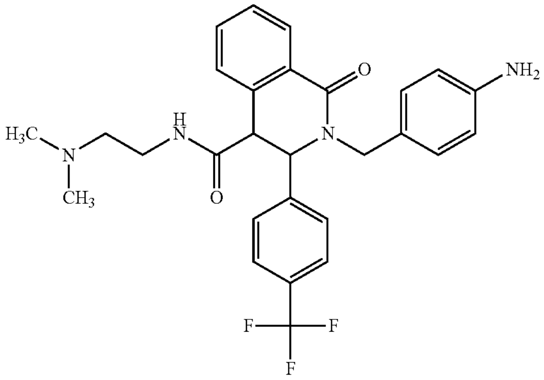
OC 381
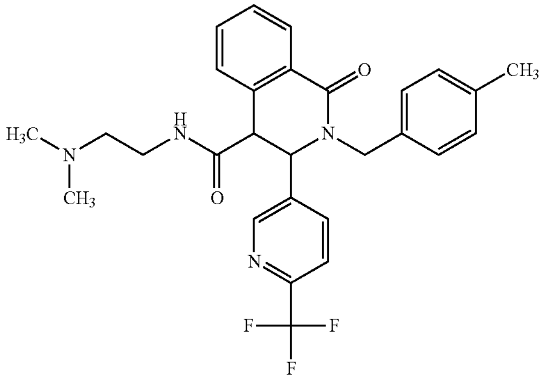
Example 2B: Synthesis of Stereoisomers of the Compounds of the Invention
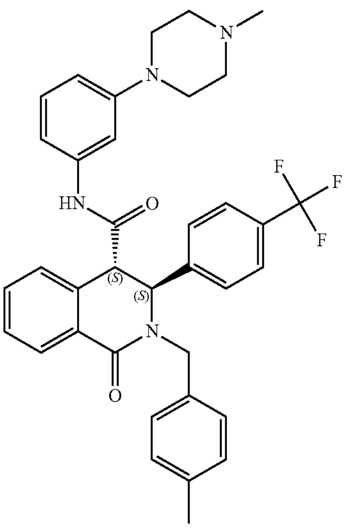
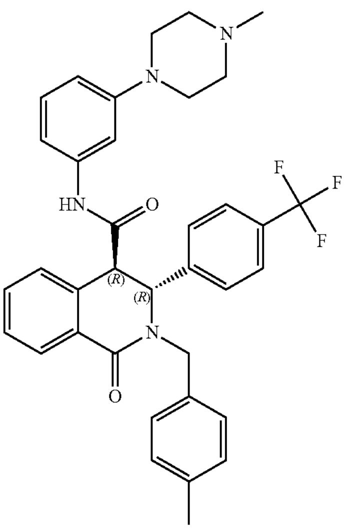
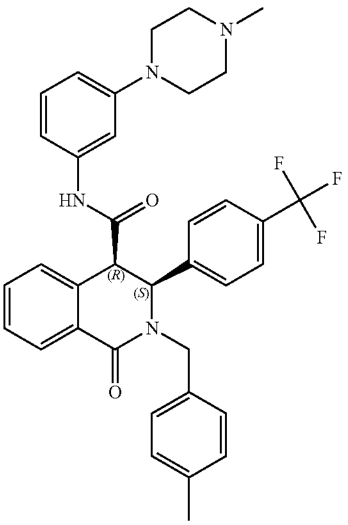

-continued

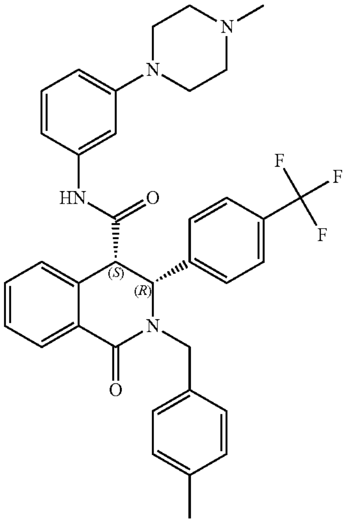

Possible Stereoisomers for OC246

Preferred stereoisomers of OC 246 according to the present invention are (3R,4R)-N-[3-(4-methylpiperazin-1-yl) phenyl]-2-[(4-methylphenyl)methyl]-1-oxo-3-[4-(trifluoromethyl)phenyl]-1,2,3,4-tetrahydroisoquinoline-4-carboxamide) and (3S,4S)-N-[3-(4-methylpiperazin-1-yl) phenyl]-2-[(4-methylphenyl)methyl]-1-oxo-3-[4-(trifluoromethyl)phenyl]-1,2,3,4-tetrahydroisoquinoline-4-carboxamide)

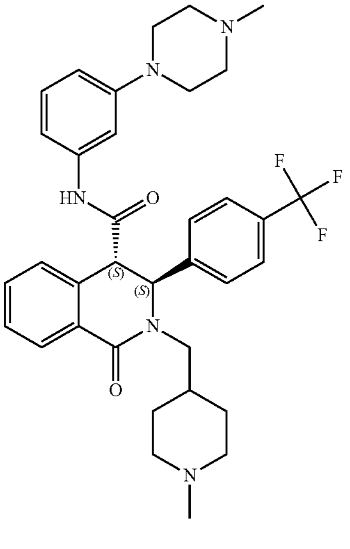

-continued

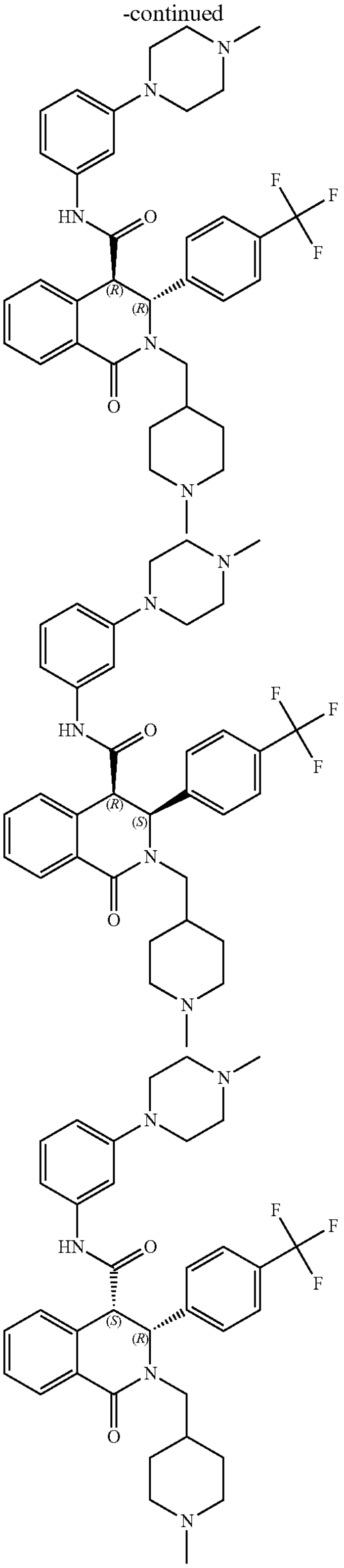

Possible Stereoisomers for OC974

Preferred stereoisomers of OC 974 according to the present invention are VSP0034 UB-17964, (3R,4R)-N-[3-(4-methylpiperazin-1-yl) phenyl]-2-[(1-methylpiperidin-4-yl)methyl]-1-oxo-3-[4-(trifluoromethyl)phenyl]-1,2,3,4-tetrahydroisoquinoline-4-carboxamide); and VSP0035

UB-17971, (3,4S)-N-[3-(4-methylpiperazin-1-yl) phenyl]-2-[(1-methylpiperidin-4-yl)methyl]-1-oxo-3-[4-(trifluoromethyl)phenyl]-1,2,3,4-tetrahydroisoquinoline-4-carboxamide)

Example 3: Biological Testing

Cytofluorimetric (CF) analysis can be used to detect the level of E7 protein expression in different HPV cancer isolates and to analyze the cell cycle state of a given cell.

Method 1: Sample Preparation for Cytofluorimetric Analysis—Intracellular Antibody Labeling For intracellular antibody labeling, 0.5×106 cells are washed once with 1 ml ice-cold PBS. Cells are centrifuged at 350×g for 5 minutes at 4° C. and then fixed in 1% paraformaldehyde (1 ml/106 cells) for 20 minutes at 4° C. Cells are washed with 1 ml ice-cold PBS and centrifuged at 350×g for 5 minutes at 4° C. To permeabilize cells, 100% ice-cold methanol (1 ml/106 cells) is added to the cells and incubated for 20 minutes at 4° C. followed by centrifugation at 350×g for 5 minutes at 4° C. Cells are washed with 1 ml ice-cold PBS, centrifuged at 350×g for 5 minutes at 4° C. and resuspended in 0.1% saponin+2% FBS in PBS (ice-cold). Cells are left for 20-30 minutes at room temperature to reduce the background signal and then centrifuged at 350×g for 5 minutes at 4° C. The primary antibody (mAb_HPV16E7-1 (VS13004); concentration 1 μg/μl) is diluted in 0.1% saponin+2% FBS (dilution 0.25 μg/50 μl of incubation buffer per 1×106 cells (5 ng/μl)). Cells are incubated with primary antibody for 30 minutes at room temperature, washed with 0.1% saponin+2% FBS and centrifuged at 350×g for 5 minutes at 4° C. The secondary antibody (FITC conjugated goat anti-mouse IgG1-IgM, BD, cat. #555988) is diluted in 0.1% saponin+2% FBS (dilution 1:50). Cells are incubated with secondary antibody for 30 minutes at room temperature, washed once with 0.1% saponin+2% FBS, once with PBS and centrifuged at 350×g for 5 minutes at 4° C.

Method 2: Cytofluorimetric (CF) Cell Cycle Analysis Using Propidium-Iodide Staining Propidium-Iodide (PI) DNA staining is performed to facilitate cell cycle analysis. For PI-DNA staining, fixed cells and eventually antibody-stained cells are resuspended in 450 μl of PBS (per 106 cells) and incubated with 100 μg/ml RNase (stock 1 mg/ml, in PBS) for 10 minutes at 37° C. Cells are then incubated with 5 μg/106 cells of PI (stock 1 mg/ml in PBS) for 10 minutes at room temperature. Samples are stored at 4° C. until CF analysis.

Method 3: Cytofluorimetric Analysis (CF)

Cells are resuspended in 700 μl PBS prior to CF analysis with a Beckman Coulter FC 500 MPL, (excitation laser 488 nm). Data analysis is done using the Beckman Coulter software packages MXP for acquisition and CXP for data analysis which includes MFI calculation. Detection of HPV-E7 protein expression is based on morphology back-gating of FL1 histogram (logarithmic scale) with gating for dot plot FS (Forward Scatter) log/SS (Sideward Scatter) log and gating for histograms SS log.

Method 4: E7 Degrader Assay

In order to define the level of E7 protein expression and to study the extent of E7 protein steady state level reduction in E7 expressing cells in the presence of various compounds, FC analysis is implemented using the intracellular antibody labeling procedure for monoclonal antibodies to HPV E7. E7 signal intensities are analyzed from the obtained FL1 histograms at logarithmic scale. The FL1 single histogram graph represents the variation in the mean fluorescence intensity (MFI) channel for cells treated with selected compounds compared to cells not incubated with primary antibodies but incubated with secondary, which allows to test for auto-fluorescence, and non-compound treated cells as controls. Non-primary antibody-stained cells are used to set the acquisition parameters to zero. Decrease of the mean fluorescence intensity channel corresponds to a decrease in the expression of HPV16 E7 protein. Degradation of E7 in cells is calculated as percent (%) reduction in MFI(x-Me) using the following formulas:

$$\% D_{rel}=(T-C)/T*100; \quad \text{i) relative degradation:}$$

$$\% D_{ad}=(T-C)/(T-CHX)*100; \quad \text{ii) adjusted degradation:}$$

Drel=relative degradation,

Dad=adjusted degradation assuming CHX % Drel=100;

T=MFI of non-treated cells;

C=MFI of compound treated cells;

CH=MFI of cycloheximide (CHX) treated cells;

For comparison within one experiment i) the % relative degradation (Drel) is sufficient, whereas for comparison between two or more experiments ii) the adjusted degradation (Dad) is used and CHX steady state is set to a 100% degradation parameter.

Method 5: Cell Extracts and Westernblot for E7 Protein Detection

Reagents for Extract Preparation and Western Blotting:

Extraction Buffer: 2.5× (Tris 0.25M pH6.8, Glycerol 50%, SDS 10%), Gels: 4-12% gradient gels (Bolt® 4-12% Bis-Tris Plus Gel). MES Buffer: 50 mM MES, 50 mM Tris Base, 0.1% SDS, 1 mM EDTA, pH 7.3, Blotting membrane: Nitrocelulose 0.2 μm (Whatman Protran #10401394), 3MM filter paper (e.g. Whatman 3MM Chr, #3030917). Western Detection Reagents: WB Wash Buffer 1× (TBET): 20 mM Tris, 150 mM NaCl, 0.125% Tween20, pH 7.8; skim-milk powder (less than 0.15% fat content). Phosphate buffered saline (PBS) 1×: prepared as 1 L add 8 g sodium chloride (NaCl), 0.2 g potassium chloride (KCl), 1.44 g sodium phosphate, dibasic ($Na_2HPO_4$) and 0.24 g potassium phosphate, monobasic ($KH_2PO_4$) to 1 L $dH_2O$, pH adjusted to 7.2.

Cell Extract Preparation:

A) For native cell pellets or cell pellets fixed in Methanol or Ethanol, extraction Buffer is added as for cells in cell culture and proceeded as specified below. Paraffin embedded cells fixed in formaldehyde must be rehydrated as described for IHC procedures in the art before proceeding accordingly.

B) For cells in cell culture the following procedure for the preparation of a total cell extract is used. Freshly seeded cells are grown for 24 hours to obtain 65-75% confluency (corresponds for CaSki cells to a plating of approx. $2\times10^6$ cells/10 cm Ø cell culture dish). Cell culture dishes with medium are out on ice for 5 minutes.

Media is aspirated from cultures and dishes are keep on ice. Cells are washed two times with ice-cold PBS 1×. All remaining liquid is aspirated.

Put plates at room temperature and immediately lyse cells by the addition of warm 500 μl Extraction Buffer (2.5×) preheated to 96° C., suggested volume is specified below. Lysed cells are scraped off the dish and transfers to microcentrifuge tubes, followed by 2×10 sec sonication to complete cell lysis at room temperature. The samples are heated at 96° C. for 10 min and centrifuged for 5 min at 12000 g at room temperature.

Supernatants are transferred into a new tube and DTT is added to a final concentration 100 mM. Prior to gel loading the sample is heated at 96° C. for 10 min. SDS-PAGE gel load 10 to 20 μl. Extracts can be stored at −20° C.

Protein Blotting:

Endogenous E7 proteins are rigid, tightly folded molecules and are bound only transiently onto hydrophilic membranes during protein blotting procedures, in particular employing semidry methods. Thus, for protein blotting a buffer system containing 40% (v/v) of Methanol is used. These buffers tend to be unstable and therefore freshly prepared solutions need to be used. E7 antibodies are used in TBET at pH7.8. Under these conditions western blot transfer is not complete for most other proteins. If staining of different proteins of the same gel is done, the gel is divided prior to blotting, 40% Methanol is used in the transfer buffer for E7 and a transfer buffer containing 20% Methanol is used for most of the other markers. For optimal retention of transferred E7 protein on the membrane, it must be allowed to air-dry completely after transfer (minimum 2 hours, preferably overnight). 0.2 μm nitrocellulose is used as blotting membrane. To prepare 50 ml of Transfer Buffer 2.5 ml MES Buffer 20×, 27.5 ml ultrapure water and 20 ml Methanol are mixed prior to the transfer (final Methanol concentration 40% (v/v)). A bottom stack is created by soaking filter papers in Transfer Buffer, the membrane is wetted in ultrapure water the gel is transferred onto the membrane. and the upper stack is placed. Transfer is for 1 hour at 0.8 mA/cm2. After transfer the membrane is blotted between 2 layers of dry 3MM filter paper and transferred to two new pieces of 3MM paper, wrapped in aluminum foil and let dry at room temperature overnight.

Western Blot Detection:

All incubations are carried out at room temperature. Blocking Buffer: 2% solution (w/v) of skim-milk powder in WB Wash Buffer 1×. Skim-milk powder (less than 0.15% fat content).

Blocking:

After overnight drying at RT, wet the blotted membrane in WB Wash Buffer 1× for 5 min. Make sure that the membrane is completely rehydrated—do not rehydrate in solutions containing milk powder or similar blocking proteins. Block the membrane with abundant volume of WB Blocking Buffer for 30 minutes with gentle agitation. Make sure to use sufficient volume of buffer to cover the membrane completely. Discard blocking buffer.

Primary Antibody:

Dilute primary antibody mAb_HPV16E7-1 (VS13004) 1:1000 in WB Blocking Buffer.

Incubate 2 hours with gentle shaking. Discard antibody solution. Wash membrane two times with abundant volume of WB Blocking Buffer. Incubate three times 10 minutes with gentle shaking in WB Blocking Buffer.

Secondary Antibody:

Dilute secondary anti-mouse HRP antibody in WB Blocking Buffer according to manufacturer instruction (e.g. CST Anti mouse IgG HRP-linked Ab, #7076, 1:3000). Incubate 1 hour with gentle shaking. Wash membrane two times with abundant volume of WB Blocking Buffer. Incubate three times 10 minutes with gentle shaking in WB Blocking Buffer. Wash membrane two times with abundant volume of PBS 1×. Incubate 10 minutes in PBS 1× with gentle shaking. The membranes are developed using standard chemo luminescence (ECL) detection systems following imaging with Licor or Viber devices.

Method 6: Analysis of the Inhibition of Sars-CoV2 Replication by the Molecules of the Invention Measured by an RNA qPCR Analysis.

Vero E6 cells were pre-incubated with the compounds at a concentration of 7.5 μM. The cells were infected with a patient derived SARS-2 Coronavirus (COVID19). Cellular supernatants were collected 3 days after infection and centrifuged at 2000 rpm for 5 min to remove detached cells. Viral RNAs were extracted using a MagNA Pure 24 system (Roche, Germany). SARS-CoV-2 RNA genomes were quantified with the TIB MOLBIOL LightMix Assay SARS-CoV-2 RdRP RTqPCR assay kit with RNA Process Control PCR Kit (Roche). The PCR reaction setup was performed using a BRAND LHS laboratory robot to ensure quality. The amplification was performed with a LightCycler 480 II (Roche). Method used in FIG. 10.

Method 7: Analysis of the Inhibition of Sars-CoV2 Replication by the Molecules of the Invention Measured by the SARS-CoV-2/VeroE6-EGFP HTS Antiviral Assay (384-Well) and SARS-CoV-2/Huh7-EGFP HTS Antiviral Assay (96-Well);

Based on https://doi.org/10.1016/j.jviromet.2005.05.010 (Development of a homogeneous screening assay for automated detection of antiviral agents active against severe acute respiratory syndrome-associated coronavirus, Tanialvens c et al, Journal of Virological Methods, Volume 129, Issue 1, October 2005, Pages 56-63)

A) Antiviral Assay Setup and Workflow

30 μL of assay medium is first added to columns 23-24 (i.e. the cell controls) of the assay-ready plates as provided by the partner.

A cell suspension of 30 μl is then added to all columns 1-24.

The plates are then transferred to the robotics/isolator system.

30 μl of 2× virus dilution (MOI is still being determined) is added using no-contact liquid dispensing to columns 1-22.

The final assay volume is 60 μl+the volume of the pre-plated compound.

The DMSO percentage is kept <1%.

Plates are incubated at 37° C. for at 5 days.

Standard whole-well fluorescence plate readout is performed (self-optimizing protocol, ~6 min per 384-well plate, 4 reads/well).

High-content imaging readout is performed (auto-focus on each well, no binning, 1 channel, 5× objective, ~25 min per 384-well plate).

B) Screening Assay Details:

Fluorescent EGFP reporter VeroE6 cells.

SARS-CoV-2 isolate BetaCov/Belgium/GHB-03021/2020.

Plate readout: after 5 days.

Plate reader whole-well fluorescence measurement: 4 reads/well, average read is provided as raw data.

Whole-well high-content imaging (5× objective): raw data provided are

- calculated number of bright objects (proportionate to the cell number).
- calculated surface covered by the fluorescent cells.
- calculated intensity of the surface covered by the fluorescent cells.

TABLE 1

| Commercial substances assessed alone or in combination studies | | | |
|---|---|---|---|
| Name | Chemical Formula | | Source |
| CI-1040 | 2-(2-Chloro-4-iodophenylamino)-N-(cyclopropylmethoxy)-3,4-difluorobenzamide CAS No.: 212631-79-3 | ATP non-competitive MEK1/2 inhibitor with IC50 of 17 nM in cell-based assays, 100-fold more selective for MEK1/2 than MEK5 | MedChem Express |
| Rapamycin | C51H79NO13 (CAS No.: 53123-88-9) | (Sirolimus, AY 22989, NSC-2260804) specific mTOR inhibitor with IC50 of ~0.1 nM HEK293 cells. | MedChem Express |
| Torin-1 | $C_{35}H_{28}F_3N_5O_2$ (CAS No.: 1222998-36-8) | inhibits both mTORC1/2 complexes with $IC_{50}$ values between 2 and 10 nM | MedChem Express |
| Torin-2 | $C_{35}H_{28}F_3N_5O_2$ (CAS No.: 1223001-51-1) | Inhibits both mTORC1 and mTORC2 | MedChem Express |
| CGP57380 | $C_{11}H_9FN_6$ (CAS No.: 522629-08-9) | selective inhibitor of Mnk1 with $IC_{50}$ of 2.2 µM, but has no inhibitory activity against p38, JNK1, ERK1/2, PKC, or Src-like kinases. | MedChem Express |
| Coptisin | $C_{19}H_{14}NO_4^+$ (CAS No.: 3486-66-6) | Natural compound | MedChem Express |
| Neifinavir-Mesylat | $C_{33}H_{49}N_3O_7S_2$ (CAS No.: 159989-65-8) | selectively binds to and inhibits human immunodeficiency virus (HIV) protease | Selleck |
| ON-01910.Na | $C_{21}H_{24}NNaO_8S$(CAS No.: 1225497-78-8) | ON-01910 is a non-ATP-competitive inhibitor of PLK1 with IC50 of 9 nM in a cell-free assay. It shows 30-fold greater selectivity against Plk2 and no activity to Plk3. Inhibits PI3K/Akt pathway | Selleck |
| Cepharantin | $C_{37}H_{38}N_2O_6$ (CAS No.: 481-49-2) | Natural compound | Selleck |

Test 1: E7 Degrader Assay Using FC $1\times10^6$ freshly seeded CaSki cells (ATCC CRL-7915), are grown in 10 cm diameter cell culture dishes in RPMI1640, 10% FCS medium at 37° C. 5% $CO_2$ overnight and then incubated in the presence of 10 µM Cycloheximide (CHX) 10 µM OC246 or with vehicle alone for four hours at 37° C. 5% $CO_2$. Following this E7 protein is assessed by cytofluorimetric analysis using intracellular HPV16 E7 antibody labeling. An overlay of the single FL1 histograms obtained from vehicle and the OC246 treatment is shown in FIG. 1, Overlay A) histogram to the left CHX treatment, histogram to the more right vehicle (CH 1.71; T 8.06; % $D_{rel}$ 78.78, % $D_{ab}$ 100%)—Overlay B) histogram to the left OC246 treatment, histogram to the more right vehicle ($C_{OC246}$ 4.53; T 8.06; % $D_{rel}$ 43.79,% $D_{ab}$ 55.59). Measured MFI and D values in parenthesis. FIG. 1 shows representative Histograms from E7 Degrader Assay.

Test 2: Drug Screening Using the E7 Degrader Assay.

The degrader assay was used to screen a series of compounds for E7 degrading activity. A summary Table 2 of the corresponding % Dad values are listed below.

TABLE 2

| COMPOUND | % $D_{ad}$ | SD | COMPOUND | % $D_{ad}$ | SD |
|---|---|---|---|---|---|
| OC244 | 0 | 0 | OC250 | 19 | 1.52 |
| OC245 | 0 | 0 | OC251 | 1 | 0.08 |
| OC246 | 56 | 4.48 | OC252 | 0 | 0 |
| OC247 | 6 | 0.48 | OC253 | 0 | 0 |
| OC974 | 68 | 5.44 | OC254 | 16 | 1.28 |
| OC975 | 67 | 5.36 | OC255 | 2 | 0.16 |
| OC976 | 54 | 4.32 | OC256 | 8 | 0.64 |
| OC973 | 20 | 1.6 | OC257 | 12 | 0.96 |
| OC972 | 32 | 2.56 | OC258 | 0 | 0 |
| OC971 | 26 | 2.08 | OC377 | 35 | 2.8 |
| OC970 | 20 | 1.6 | OC378 | 48 | 3.84 |
| OC969 | 66 | 5.28 | OC379 | 26 | 2.08 |
| OC968 | 37 | 2.96 | OC380 | 3 | 0.24 |
| OC967 | 22 | 1.76 | OC381 | 41 | 3.28 |

Test 3: Cell Cycle Analysis of Various Compounds of the Invention

CaSki cells were incubated with various compounds and cell cycle distribution of the cells was assessed using Propidium-Iodide staining.

In order to analyze the cytostatic versus the cytotoxic effect of OC compounds, cell cycle profiles were analyzed in vitro after 48 hour incubations using Flow Cytometry as a read out. For this a cell cycle analysis from selected OC E7 degrader compounds was conducted in CaSki cells. Using 6 well plates, $1.5\times10^5$ cells were seeded for each well and grown over night at 37° C. 5% $CO_2$. Following that, cells were treated with 10 µl of OC compound in DMSO at the concentrations as indicated in Table 2. For analysis of the cell cycle behavior, cells were analyzed in the presence of propidium Iodide ($PI^-$) by flow cytometry (FC). Briefly, cells were detached by trypsin digestion, all supernatants were included in the analysis, and fixed with 70% ice cold ethanol and stored at 4° C. until FC analysis using $PI^-$ staining (1 mg/ml). At least 7000 events were acquired for each sample.

To further analyze apoptosis, wash out experiments were done by incubating E7 expressing cells for a short period with a compound of the invention and then the cells were washed for three times with fresh medium and incubated for additional time periods and FC-PI profiles were assessed. FIG. 2 shows the FC PI-stain for cell cycle distribution of CaSki cells after 4 hours growth in the presence of 50 µM OC246 compound invention, wash out and further growth compared to vehicle control (a), further growth for 24 hours (b) and further growth for 48 hours (c). X axis PI-FL3 signal intensity in logarithmic scale, Y axis number of events. Middle peak G1 content of the cells, peak to the right G2/M content and left peaks sub-G1 population as a measure of apoptosis.

Conclusion: OC246 and OC974 are strong apoptosis inducer in cervical cancer cells as measured from the observed sub G1 content already after 48 hours. Other compounds did not induce substantial apoptosis under the experimental conditions used. The choice of 48 hours as the incubation time, instead of the 72 or 94 hours usually used for these types of experiments allows to argue for the nearly complete apoptosis inducing effects observed for OC246/OC974 (89.4/82.9%) as a first cycle event.

TABLE 3

| Changes in cell cycle distribution (in %) induced by OC compounds | | | | | | |
|---|---|---|---|---|---|---|
| compound | G1/5 μM | G1/10 μM | G2/5 μM | G2/10 μM | A*/5 μM | A*/10 μM |
| No treatment | 53.3 | 53.3 | 15.6 | 15.6 | 15.0 | 15.0 |
| OC246 | 48.0 | 1.5 | 15.7 | 0.2 | 19.6 | 89.4 |
| OC974 | 49.6 | 8.7 | 9.9 | 0.8 | 19.5 | 81.8 |
| OC975 | 49.9 | 51.4 | 10.4 | 10.5 | 13.9 | 11.8 |
| OC976 | 58.8 | 53.2 | 9.3 | 16.9 | 11.4 | 12.8 |
| OC972 | 53.2 | 48.4 | 16.9 | 15.9 | 12.8 | 13.5 |
| OC973 | 52.1 | 52.6 | 17.6 | 11.5 | 11.1 | 13.0 |
| OC968 | 52.7 | 48.0 | 18.0 | 19.7 | 11.9 | 11.6 |

*Apoptosis as measured from total SUB G1 content on logarithmic scale

Test 4: E7 Degrader VSP035 Shows First Order Kinetics E7 Protein Destabilization and Consequent Regulation to Loss of HPVE7 of the mTOR and pi3K Signaling Pathways.

HPV 16 E7 protein degradation time course with VSP035. $2\times10^5$ Caski cells per well were seeded in 2 ml RPMI 1640+10% fcs in 6 well plates and allowed to rest for 1 day at 37° C. Followed by treatment with 10 μM of VSP035 for the indicated time points. B-actin was used as an internal loading control. Vsp035 induced a stable e7 reduction even with short duration treatments that persisted for the observed time span of 24 hours. (FIG. 3*a*))

Example Shown in FIG. 3*b*) Time Course of VSP035.

$1\times10^6$ Caski cells were seeded in each 10 cm dish in 12 ml RPMI 1640+10% FCS and allowed to rest for 2 days at 37° c. Cells were then treated with 10 μm VSP035 for the indicated times and lysed for WB analysis. B-actin was used as an internal loading control.

For E7, VSP035 treatment reveales a steady decline over time; the longer the cells are treated the greater the decline, p(S473)Akt, Sting and Irf-3 do not appear to be influenced by VSP035.

The 24 h time point shows the greatest E7 reduction, which is in accordance with the increase in Ptpn14 and p53. Ptpn14 is a known E7 Substrat. PD-L1 is regulated by E7 and thus VSP035.

Example Shown in FIG. 3*c*. Long-Lasting Robust Degrader Effect of VSP035 on HPV16 E7 Steady State Protein Levels.

$1.5\times10^4$ Caski cells were seeded in each well of 6-well plates in 2 ml RPMI 1640+10% FCS and allowed to rest for 2 days at 37° C.; followed by treatment with 10 μm VSP035 for the indicated time periods and were either harvested 6 h or 24 h after timepoint 0 h or 24 h. Media with VSP035 was removed by washing twice with rpmi 1640+10% fcs and was changed to RPM 1640+10% fcs without the VSP035 compound for the remaining time until the harvest.

Example shown in FIG. 3*d*) Effect of E7 degraders (OC974, VSP034, VSP035) on E7 steady state levels and cell signaling molecules activation in comparison to mTor inhibitors (Rapamycin, Torin 1).

Cell signaling in CaSki cells post treatment with HPV16 E7 degraders, MAPK and mTOR inhibitors. Translation of mRNA can be stimulated by mTORC1 via its downstream substrates, S6 kinases and 4E-BP1/eIF4E [Choo, 2008]. In addition to the latter, which has been investigated in several cell lines, a more detailed analysis of key signaling molecules was carried out in a next step. In order to better understand the mechanism of the Valdospan compounds (OC974, VSP034 and VSP035) and to distinguish these small molecules from commonly used mTOR inhibitors, CaSki cells were treated with various inhibitors including: CGP 57380, an MNK1 inhibitor; Rapamycin and Torin 2 as mTOR inhibitors; Torin 1 an mTORC1/2 inhibitor; PD184352 an inhibitor of MEK; and MKK2 and AT13148 as multi-AGC kinase inhibitors. The expression and phosphorylation of key molecules in major cell signaling pathways were investigated and show distinct but overlapping function of molecules of the invention.

A. $8\times10^5$ Caski cells were seeded in 10 cm dishes in 12 ml RPMI 1640+10% FCS and allowed to rest for 2 days at 37° C. Followed by a 6 h treatment with 10 μm VSP034, 10 μm VSP035, 10 μm OC974, 250 nm Torin 1 and 100 nm Rapamycin, cells were scraped in 400 μl lysis buffer and analyzed by WB.

B. $1\times10^6$ Caski cells were seeded in 10 cm dishes in 12 ml RPMI 1640+10% FCS and allowed to rest for 2 days at 37° c. After a 6 h treatment with 10 μm & 5 μm VSP035, 10 μm CGP-57380, 100 nm Rapamycin, 250 nm Torin 1, 100 nm Torin 2, 100 nm PD184352, and 100 nm AT13148, cells were scraped in 400 μl lysis buffer and analysed by WB. B-Actin and Vinculin were used as internal loading controls.

Example Shown in FIG. 3*e*. Effect of Various Inhibitors on Signaling Molecules in Caski Cells in Comparison to the Molecules of the Invention.

$1\times10^6$ Caski cells were seeded in 10 cm dishes in 12 ml RPMI 1640+10% FCS and allowed rest for 2 days at 37° c. After a 6 h treatment with 10 μm & 5 μm VSP035, 10 μm CGP-57380, 100 nm rapamycin, 250 nm torin 1, 100 nm torin 2, 100 nm pd184352, and 100 nm at13148 cells were scraped in 400 μl lysis buffer and analyzed by WB. B-Actin was used as an internal loading control. VSP035 consistently induced the strongest decrease in the HPV16 e7 protein, followed by Torin 1, Torin 2, GP-57380 and Rapamycin. In addition to a greater decrease of E7 by torin 1 relative to the other inhibitors but not VSP035, Torin 1 and Torin 2 exhibit the similar effects on all other investigated cell signaling molecules.

VSP035 led to a dose dependent hypophosphorylation of 4E-BP1. Rapamycin also showed hypophosphorylation of the total 4E-BP1; but in general, showed an increase in p-4E-BP1 (Thr 37/46) phosphorylation. Exeot for Torin 1 and Torin 2, all other compounds allowed for Thr46 phosphorylation. After Torin 1 and Torin 2 incubation, only the hypophosphorylated 4E-BP1 was present without Thr37/46 or Ser65 phosphorylation. Ser65 phosphorylation on 4E-BP1 was reduced or completely inhibited by all compounds. Thus, clearly distinguishing downstream-effects in comparison to a general TOR Kinase inhibition.

After the priming of Thr37 and Thr46 phosphorylation's, Thr70 phosphorylation is described as ectopic to Ser65 phosphorylation. In addition to mTOR, other kinases are able to phosphorylate 4E-BP1 [e.g. Qin, 2016, review]. This is consistent with VSP035 regulating and preventing the release of 4E-BP1 from eIF4E and thereby inhibits cap-dependent translation.

Phosphorylation of 4E-BP1 on Ser65 and the p70S6 kinase on Thr389 showed the same trend, i.e. that they were inhibited or strongly reduced by 10 μM VSP035, Torin 1, Torin 2, rapamycin, 5 μM VSP035 and CGP 57380, in increasing order.

Important phosphorylation of AKT on Ser473 was inhibited only by Torin 1 and Torin 2but not with VSP035 and Rapamycin.

Test 5:

Extracts from CaSki, (HPV+) cells were analyzed in western blots after incubation of the growing cells for 4 hours with vehicle (1), 100 nM Rapamycin (2), 10 μM Akt1 VIII inhibitor (3), 2 μM GSK3 IX inhibitor+10 μM Akt1 VIII inhibitor (4), 2 μM GSK3 IX Inhibitor (5), 0.5 μM PI103+0.1 μM Wortmanin PI3KCA inhibitor (6); staining was with HPV16E7(VS13004) panS6 ribosomal protein, anti-phosphor specific S6 ribosomal protein Serine 235/236, anti-phosphor specific Akt1 Serine 473 and pan Akt1 specific monoclonal antibodies. This test shows, that the presence of Rapamycin, PI3KCA and Akt1 inhibitors lead to degradation of E7 proteins in CaSki cells (FIG. 4).

Test 6:

Extracts from CaSki, (HPV+) and Osteosarcoma cells (U2Os, HPV−) were analyzed in western blots after incubation for 4 hours with vehicle (1), 10 μM OC246, (2) or 100 nM Rapamycin (3) and 10 μM OC246 and 100 nM Rapamycin (4) staining was with P70-S6K(T389); panAkt, Akt (p473); pS6 S235/236 and HPV16E7 antibody detection. This test shows that OC246 does not inhibit signaling of phosphor-Akt S473 as this site is stable phosphorylated in HPV E7 and dominant active PIK3CA-E545K(p110a) containing CaSki cells, nor in PIK3CA WT U2OS cells. Moreover, of p70 S6 kinase, phosphor-p70-S6K T389 is dephosphorylated in response to E7 degradation (FIG. 5).

Test 7:

VSP035 Regulates Tumor Immune-Suppressor PDL-1

Extracts from CaSki, (HPV+) cells were analyzed in western blots and stained with monoclonal antibodies to PDL-1 (gly-PDL-1 represents the glycosylated population of PDL-1). $1.5\times10^5$ Caski cells, a cell-line that shows high level of PDL-1 expression, were seeded in 2 ml RPMI 1640+10% FCS in 6-well plates and incubated at 37° C. to allow for cell growth. 24 h after seeding, cells were treated with VSP035, cycloheximide (CHX) and/or MG132 protasome inhibitor as indicated. Cells were harvested for analysis for BY WB. The results show a strong regulation towards faster migrating, posttranslational modified bands in a dose dependent manner, which was more expressed after 8 hours as compared to the 4-hour time-point. In particular, faster migrating band abundancy was regulated by proteasome inhibitor MG132 and the protein was destabilized in the presence of CHX. This demonstrates that E7 stabilizes PDL-1 and the E7 degrader VSP035 reverses these effects making it a valid pdl-1 destabilizer (FIG. 6).

Test 8:

(D) Extracts from SiHa, (HPV+) cells were analyzed in western blots after incubation for 24 hours with vehicle (0), or 10 μM OC246 for 12 and 24 hours; blots were were stained with monoclonal antibodies to HPV16E7, Actin and the Retinoblastoma Protein pRb1; an increase of Rb protein signals can be detected with decreasing E7 signal (FIG. 7).

Test 9:

HPV16E7 abundance after incubation for 4, 8, and 12 hours respectively with CHX (cycloheximid) OC974 and various chemotherapeutics.

Extracts from CaSki, (HPV+) cells were analyzed in western blots and stained with HPV16E7 and p53 (DO1) specific monoclonal antibodies: vehicle (lanes 1, 14), CHX_Cycloheximide, (lanes 2, 3, 4) OC974 (5, 6, 7), CDDP_Cisplatin (8, 9, 10), DOX_Doxorubicin (11, 12, 13) (FIG. 8).

Test 10:

HPV16E7 abundance after incubation for 4, 8, and 12 hours respectively with OC246 and various chemotherapeutics. Extracts from CaSki, (HPV+) cells were analyzed in western blots and stained with HPV16E7 and p53 (DO1) specific monoclonal antibodies: vehicle (lanes 1, 14), Vincristine (lanes 2, 3, 4), AKT1 VIII inhibitor (5, 6, 7), Etopside (8, 9, 10), OC246 (11, 12, 13).

Test 11:

Extracts from CaSki, (HPV+) cells were analyzed in western blots after incubation of the growing cells for 4 hours with vehicle (1), 10 μM OC246 (2), 30 μM LLnL (MG101)(3), 10 μM OC246+30 μM LLnL (MG101) (proteasome inhibitor) (4), 10 μM G5 (DUB, de-ubiquitinase inhibitor) (5), 10 μM OC246+10 μM G5 (DUB, de-ubiquitinase inhibitor) (6), vehicle (7) 10 μM OC246+0.5MM PI103+0.1 μM Wortmanin PI3KCA inhibitor; staining was with HPV16E7(VS13004) specific monoclonal antibodies.

TABLE 4

Antibodies used in the WB experiments
Table 4 antibodies used for Test 1-11

| Target | clone | dilution | company | ID/Cat. Nr. |
|---|---|---|---|---|
| HPV16E7 | | 1:1000 | Cervimax | |
| β-Actin | 13E5 | 1:3000 | Cell Signaling | 4970S |
| p70 S6 Kinase | 49D7 | 1:1000 | Cell Signaling | 2708S |
| p-p70 S6 Kinase (Thr389) | 108D2 | 1:1000 | Cell Signaling | 9234S |
| p-p70 S6 Kinase (Ser371) | | 1:1000 | Cell Signaling | 9208S |
| p-p70 S6 Kinase (Thr421/Ser424) | | 1:1000 | Cell Signaling | 9204S |
| Akt pan | C67E7 | 1:1000 | Cell Signaling | 4691S |
| p-Akt (Ser473) | D9E | 1:2000 | Cell Signaling | 4060S |
| p-Akt (Thr308) | 244F9 | 1:1000 | Cell Signaling | 4056S |
| p44/42 MAPK | 137F5 | 1:1000 | Cell Signaling | 4695S |
| p-p44/42 MAPK (Thr202/Tyr204) | D13.14.4E | 1:2000 | Cell Signaling | 4370S |
| IRF-3 | D6I4C | 1:1000 | Cell Signaling | 11904S |
| p-IRF-3 (Ser386) | E7J8G | 1:1000 | Cell Signaling | 37829 |
| PTPN14 | D5T6Y | 1:1000 | Cell Signaling | 13808 |

TABLE 4-continued

Antibodies used in the WB experiments
Table 4 antibodies used for Test 1-11

| Target | clone | dilution | company | ID/Cat. Nr. |
|---|---|---|---|---|
| PTPN14 | 2B3H7 | 1:1000 | ThermoScientific | MA531871 |
| p-Rb (Ser780) | C84F6 | 1:1000 | Cell Signaling | 3590S |
| p-Rb (Ser807/811) | D20B12 | 1:1000 | Cell Signaling | 8516S |
| S6 ribosomal protein | 5G10 | 1:1000 | Cell Signaling | 2217S |
| p-S6 ribosomal protein (Ser235/236) | D57.2.2E | 1:2000 | Cell Signaling | 4858S |
| elF4B | | 1:1000 | Cell Signaling | 3592S |
| p-elF4B (Ser406) | | 1:1000 | Cell Signaling | 5399S |
| elF4E | | 1:1000 | Cell Signaling | 9742S |
| p-elF4E (Ser209) | | 1:1000 | Cell Signaling | 9741S |
| Mnk1 | C4C1 | 1:1000 | Cell Signaling | 2195S |
| p-Mnk1 (Thr197/202) | | 1:1000 | Cell Signaling | 2111S |
| p53 | DO-1 | 1:1000 | Cell Signaling | 18032S |
| STING | D2P2F | 1:1000 | Cell Signaling | 13647S |
| p-4E-BP1 (Thr37/46) | 236B4 | 1:1000 | Cell Signaling | 2855 |
| Non-p-4E-BP1 (Thr46) | 87D12 | 1:1000 | Cell Signaling | 4923 |
| p-4E-BP1 (Ser65) | | 1:1000 | Cell Signaling | 9451 |
| p-4E-BP1 (Thr70) | | 1:1000 | Cell Signaling | 9455 |
| 4E-BP1 | 53H11 | 1:1000 | Cell Signaling | 9644 |
| 4E-BP2 | | 1:1000 | Cell Signaling | 2845 |
| PD-L1 | E1L3N(R) | 1:2000 | Cell Signaling | 13684T |
| Vinculin | E1E9V | 1:3000 | Cell Signaling | 13901S |

Test 12: OC246 and OC974 Antitumor Efficacy on CaSki High Risk HPV16 Human Cervical Carcinoma Xenograft Model OC246 and OC974 Degraders represent compounds of a new class of anticancer agents. OC246 and OC974 are highly stable small molecules leading to the degradation of HPVE7 proteins in a cell and consequently to the inhibition of tumor cell proliferation.

The aim of this study was to assess the in vivo efficacy of OC246 and OC974 on a human cervical carcinoma (CaSki) xenograft model in nude mice. OC246 and OC974 were administered oral once daily for four times with three days off, for three cycles at 2 mg/kg/dose. Cisplatin (CDDP) was used as a reference compound with three weekly intravenous (q7dx3) administrations of 6 mg/kg.

This study, summarized in Table 3, showed that the growth of CaSki human serveical carcinoma (assessed on Day 44, one week after final treatments) was inhibited by OC246 and OC974 treatment (66.6% and 63.9% tumor growth inhibition (% TGI) respectively) with similar anti-tumor efficacy than treatment with CDDP at maximal tolerated dose (79.2% TGI).

OC246 and OC974 caused no reduction in body weight (BW) with respect to starting levels, Day 44 (+5.5% and +1.1% respectively) in contrast substantial BW loss (−10.2%) occurred in the the CDDP group. No body weight loss (BW+4.9%) occurred in the control group.

In conclusion, these results demonstrate that OC246 and OC974 have antitumor activity at well tolerated doses on a CaSki human HPV16E6 and HPV16E7 oncoprotein expressing cervical carcinoma xenograft, CaSki cells are gain of function mutated for PIK3CA-E545K (phosphatidylinositol-3 kinase 110-kDa catalytic subunit (p110a)). Moreover, these findings further support the in vivo efficacy of OC246 and OC974 on experimental tumor models after repeated oral treatments.

TABLE 5

Antitumor Efficacy of OC246 and OC 974 Against Human Cervical Carcinoma (CaSki)

| Treatment Group (n = treated mice) | Route/ Schedule (day) | Dose (mg/kg/day) | Starting Tumor Volume ($mm^3$ ± SD) | Tumor Volume Day 44 ($mm^3$ ± SD) | Δ% on Day 44 | % TGI (Day 44)[1)] | Δ% Body Weight [2)] |
|---|---|---|---|---|---|---|---|
| Control (n = 7) | os/daily 4 × week 3 cycles | 0 | 100 ± 27 | 1099 ± 503 | 100 | — | +4.9 |
| OC246 (n = 7) | os/daily 4 × week 3 cycles | 2 | 100 ± 25 | 371 ± 153 | 27 | 66.6 | +5.5 |
| OC974 (n = 7) | os/daily 4 × week 3 cycles | 2 | 78 ± 35 | 307 ± 171 | 23 | 63.9 | +1.1 |
| CDDP (n = 7) | i.v. q7 d × 3 | 6 | 100 ± 26 | 242 ± 182 | 14 | 79.2 | −10.2 |

[1)] % TGI: percentage tumor growth inhibition with respect to controls.

[2)] Percentage change in body weight. 4% between the first day of treatment (day 20) and Day 44.

Test 13 Pharmacokinetics of OC246;

Pharmacokinetics were assessed for OC246 after single oral (p.o.) administration in female NMRI mice. The compound OC246 was suspended at 50 mg/kg with Lipoid S100 and Myritol 318. Oral dose was 50 mg/kg, Final Concentration 10 mg/ml and Administration Volume 5.0 ml/kg. Blood samples were taken from three mice at individual time points after 0.25, 0.5, 1, 2, 4, 6, 8, 16, and 24 hours from administration, and analyzed using HPLC and mass-spectroscopic bioanalytical methods. The main pharmacokinetic parameters are summarized in Table 4.

TABLE 5

| | | mean | SE |
|---|---|---|---|
| $t_{max}$ | h | 2.000 | |
| $t_{last}$ | h | 24.00 | |
| $C_{max}$ | ng/mL | 1740 | 349 |
| $C_{last}$ | ng/mL | 5.18 | |
| $AUC_{last}$ | h ng/mL | 11495 | 929 |
| $AUC_{inf(obs)}$ | h ng/mL | 11512 | |
| $AUC_{\%\ extrapol\ (obs)}$ | % | 0.146 | |
| Rsq | | 0.927 | |
| $\lambda_z$ | 1/h | 0.309 | |
| $t_{1/2}$ | h | 2.25 | |
| $V_{z\_obs}$ | mL/kg | 14073 | |
| $CL_{obs}$ | mL/h/kg | 4343 | |

obs: observed; tmax: time point at Cmax; tlast: time at last quantifiable concentration; Cmax: maximum observed concentration; Clast: last quantifiable concentration; SE: standard error; AUClast: area under the concentration-time curve (AUC) calculated with trapezoidal rule between dosing time to the last measurement time point with a conc. value above the lower limit of quantification; AUCinf(obs): AUC calculated using the trapezoidal rule from 0 hours to infinity; AUC % extrapol: percentage of AUCinf(obs) that is due to the extrapolation from tlast to infinity; Rsq: goodness of fit for the determination λz in the terminal elimination phase; λz(Lambda_z): terminal elimination rate constant (of at least three last measured concentrations); t1/2: apparent terminal elimination half-life; CLobs: observed total (systemic) body clearance; Vz_obs: apparent volume of distribution based on AUClast and λz.

Test 14 Pharmacokinetic Analysis of the OC974 Trans Enantiomers VSP034 and VSP035 after the Oral Administration of a Liposomal Formulation.

The pharmacokinetic parameters of VSP034 and VSP035 encapsulated as liposomal formulation were assessed after the administration of a single 100 mg/kg dose by oral gavage to 6 female Sprague-Dawley rats weighting 250 grams (+25 g). The animals were randomized into two experimental groups (Groups 1 and 2), each composed of 3 rats. Rats belonging to group 1 were administered with VSP034 and rats belonging to group 2 were administered with VSP035. Blood was collected at baseline and 15 min, 30 min, 1, 2, 4, 6, 8, and 24 hours after the oral gavage. The rats were sacrificed 24 hours after the dosing. Blood was collected at each timepoint from the caudal vein, with the exception of the last collection (24 hours), which was performed by intracardiac puncture at the moment of sacrifice under isoflurane anesthesia. The animals were weighted immediately before the dosing to assess the proper dose and carefully monitored during the experiment. They were kept in standard housing conditions, meeting the legal requirements for the correct housing of rodents for a period not exceeding the maximum experimental endpoints. Ad libitum access to water and food was allowed. All the rats were in good conditions after the administration of the liposomal formulation and did not show any sign of suffering or abnormal behavior. Humane endpoints have not been reached. The pharmacokinetic analysis was performed using Microsoft Excel plug-in PK Solver. Pharmacokinetic parameters of two compounds are compared with the software GraphPad Prism ver. 8.0 by Student's t test for unpaired data. A p value <0.05 is considered statistically significant.

Analytical method: Compound analysis was performed following the bioanalytical method as in Test 13. In this study, carbamazepine was used as an internal standard.

Pharmacokinetic analysis: A pharmacokinetic analysis of VSP034 and VSP035 was performed using the Excel plug-in 2.0 PK Solver. The results have been fitted according to a non-compartmental modelling following extravascular administration. Concentration-vs-time curves for VSP034 and VSP035.

The main pharmacokinetic parameters (half-life, $t_{1/2}$; time to maximum plasma concentration, $T_{max}$; maximum plasma concentration, $C_{max}$, AUC Extrapolated to Infinity, $AUC_{0-inf}$; mean residence time, MRT; Apparent Volume of Distribution During Terminal Phase, $V_z/F$; and apparent oral clearance, CL/F) were calculated from the coefficients and exponents of the best-fits by using standard formulae. The results of each rat, as well as the mean, SD and median for each study group are reported in the Tables 6 and 7 below.

TABLE 6

Pharmacokinetic parameters of VSP034.

| Parameter | Unit | Mean | SD | Median |
|---|---|---|---|---|
| $t_{1/2}$ | h | 4.334 | 0.209 | 4.220 |
| $T_{max}$ | h | 1.167 | 0.764 | 1 |
| $C_{max}$ | μg/L | 89.0 | 18.1 | 87.9 |
| $AUC_{0-inf}$ | μg/L*h | 529 | 163 | 613 |
| $MRT_{0-inf}$ | h | 6.717 | 0.386 | 6.774 |
| $V_z/F$ | L/kg | 1.295 | 0.553 | 0.994 |
| CL/F | L/h*Kg | 0.205 | 0.076 | 0.163 |

TABLE 7

Pharmacokinetic parameters of VSP035

| Parameter | Unit | Mean | SD | Median |
|---|---|---|---|---|
| $t_{1/2}$ | h | 4.426 | 2.439 | 3.568 |
| $T_{max}$ | h | 2.417 | 3.126 | 1 |
| $C_{max}$ | μg/L | 246.3 | 114.0 | 277.0 |
| $AUC_{0-inf}$ | μg/L*h | 2227 | 1296 | 1484 |
| $MRT_{0-inf}$ | h | 6.830 | 2.294 | 6.587 |
| $V_z/F$ | L/g | 0.291 | 0.053 | 0.278 |
| CL/F | L/h*g | 0.054 | 0.024 | 0.067 |

A statistical analysis for comparison of the pharmacokinetic parameters of the two compounds using the Student's t test for unpaired data. No significant differences could be demonstrated for t1/2, Tmax and MRT. VSP035 AUC is significantly higher (4-fold) than that of VSP034, and Cmax shows a correlated increasing tendency, although the statistical significance could not be reached. Accordingly, VSP035 Vz/F and CL/F are significantly lower than for VSP034.

Test 15 Monolayer Assay using Sulphorhodamine B (SRB) Staining:

Various cell culture cells grown as monolayers are harvested from exponential growing cultures after treatment with various OC compounds at different concentrations. For this depending on the cell line, 10.000 to 30.000 cells were plated in 96-well flat-bottom microtiter plates. After a 24 h recovery period to allow cells to resume exponential growth, supernatants are discarded and 100 µl of culture medium (eight control wells/plate) or culture medium with the test compound are added by a liquid handling robotic system (Microlab® Starlet, Hamilton) and treatment continued for 72 hrs. Compounds are applied at 9 concentrations and eight wells/concentration). At least three independent experiments are performed. For SRB staining, cells are fixed with SRB01 (Tab. 5) for 1 h at 4° C. (final concentration of TCA=10%) washed with a plate washer (Hydroflex, Tecan©) for five times with H2O; and stained with 100 µl of SRB02 at room temperature for 10 min following 4 washes in SRB03 and finally 100 µl of developer solution SRB04 for 5 minutes with shaking. Optical density is assessed using a plate-reader (Sunrise, Tecan©) at 540 nm.

Concentrations required for half maximal response of the compound for cell growth inhibition (EC50) is calculated by non-linear regression (log[conc. of inhibitor] versus response (% T/C)) using the analysis software GraphPad Prism®, Prism 5 for windows, version 5.01 (GraphPad Software Inc., CA).

TABLE 8

SRB Assay Solutions

| | SRB ASSAY SOLUTIONS |
|---|---|
| SRB01 | Fixing solution: trichloroacetic acid (TCA) 50% w/v in $dH_2O$ |
| SRB02 | Staining solution: Sulphorhodamine B (SRB) 0.4% w/v in SRB03 washing solution; |
| SRB03 | Washing solution: acetic acid 1% in $dH_2O$ |
| SRB04 | Developer solution: Tris-Base 10 mM |

TABLE 9

EC50 Measurements of cervical cancer cells in the presence of OC246
EC50 for OC246 was assessed for the HPV E7 expressing cervical cancer cell lines Hela (ATCC CCL-2), SiHa (ATCC HTB-35), and CaSki (ATCC CRM-CRL-1550) and compared to peripheral blood mononuclear cells (PBMC) in a SRB assay. Results show IC50 activities in the low µM range as compared to >10−4 for PBMC cells.

| Cells | HPV | EC50 |
|---|---|---|
| CaSki | HPV16 | $2.89 \times 10^{-6}$ |
| SiHa | HPV16 | $3.53 \times 10^{-6}$ |
| Hela | HPV18 | $2.68 \times 10^{-6}$ |
| PBMC | — | $>10^{-4}$ |

TABLE 10

SRB assay from Caski cells for EC50 determination of various compounds of the invention shows strong anti-neoplastic activity thereof ("0" intends no activity detected with the concentrations tested), EC50 calculation via Graphpad fit (Y = 100/(1 + 10^(LogEC50 − X)*HillSlope))).

| compound | EC50 mean [nM] | 95% CI | | compound | EC50 mean [nM] | 95% CI | |
|---|---|---|---|---|---|---|---|
| VSP034 | 3586.5 | 3302 | 3871 | OC384 | 0 | 0 | 0 |
| VSP035 | 3750 | 3371 | 4129 | OC246* | 3046 | 1869 | 4223 |
| OC375 | 0 | 0 | 0 | OC247 | 6730.5 | 6236 | 7225 |
| OC377 | 6753.5 | 5625 | 7882 | OC968 | 10555.5 | 9886 | 11225 |
| OC378 | 5688 | 5077 | 6299 | OC970 | 5553 | 5027 | 6079 |
| OC379 | 11880 | 10462 | 13298 | OC972 | 67717.5 | 27868 | 107567 |
| OC380 | 11432 | 10221 | 12643 | OC973 | 6721 | 4242 | 9200 |
| OC381 | 17481.5 | 15700 | 19263 | OC974 | 1547.6 | 942.2 | 2153 |
| OC382 | 2300.5 | 1386 | 3215 | OC975 | 4335.5 | 3029 | 5642 |
| OC383 | 0 | 0 | 0 | OC976 | 4719 | 3287 | 6151 |

Test CoV2

Test 16 Antiviral Activity of the Molecules of the Invention Exemplified by SARV-CoV-2 Antiviral Activity Thereof.

SARV-CoV-2 antiviral activity by of VSP034 and VSP035 (n3; number of repeat of the assay at each condition). The results are shown in for DMSO (1), 7.5 μM VSP034 (2) and 7.5 μM VSP035 (3), y axis logarithmic scale. SARV-CoV-2 anti-viral activity by of 7.5 μM VSP034 and VSP035 shows reduction by one order of magnitude of virus load as determined by the PCR assay. (FIG. 9)

Test 17

Inhibition in % of SARV-CoV-2 virus activity by compounds of the invention, the non-toxic compound concentration of 1.25 μM was assessed. Result show strong antiviral activity of various compounds (n4). The SARS-CoV-2/VeroE6-EGFP HTS antiviral Assay (384-well) was used (Table 11);

TABLE 11

| Compound | % Inhibition | Compound2 | % Inhibition |
|---|---|---|---|
| OC246 | 45.70 | OC973 | 0.95 |
| OC247 | 30.57 | OC974 | 54.30 |
| OC375 | 41.47 | VSP034 | 45.20 |
| OC376 | 28.64 | VSP035 | 72.38 |
| OC377 | 81.61 | OC975 | 0.17 |
| OC378 | 43.44 | OC976 | 27.14 |
| OC379 | 33.39 | Torin 1 | 7.00 |
| OC380 | 72.59 | Torin2 | 1.46 |
| OC381 | 43.67 | Coptisin | 98.97 |
| OC382 | 41.20 | ON-01910.Na | 51.41 |
| OC383 | 1.15 | Neifinavir-Mesylat | 9.49 |
| OC384 | 1.21 | CGP571380 | 17.71 |
| OC968 | 2.09 | Rapamycin | 21.07 |
| OC970 | 3.03 | CI-1040 | 146.41 |
| OC972 | 5.37 | Cepharantin | 2.32 |

Test 18

SARV-CoV-2 antiviral activity of VSP035 from mono treatment, or in combination with various pharmacological drug substances at various concentrations shown by the bars from left to the right. Y axis % Inhibition. Due to lethal concentrations for Vero E6 cells, dose dependency is visible at non-lethal doses only (median of multiple experiments n4 is shown); Concentrations (left to right) Compounds and respective assay concentrations in UM are, "constant" means same concentration for the series (X axis, numbers for series): (FIG. 10).

Robust antiviral activities were demonstrated for VS035 as single agent and dose dependency over a broad range of very active synergistic drug combinations with VSP035 is demonstrated.

(1) VSP035 (10, 5, 2.5, 1.25, 0.625);

(2) Rapamycin (0.250, 0.125, 0.0625, 0.03125, 0.15625);

(3) VSP035 (constant 10), Rapamycin (0.250, 0.125, 0.0625, 0.03125, 0.15625);

(4) VSP035 (10, 5, 2.5, 1.25, 0.625), Rapamycin (constant 0.0625);

(5) CI-1040 (0.250, 0.125, 0.0625, 0.03125, 0.15625);

(6) VSP035 (constant 10), CI-1040 (0.250, 0.125, 0.0625, 0.03125, 0.15625);

(7) CGP57380 (0.250, 0.125, 0.0625, 0.03125, 0.15625);

(8) VSP035 (constant 10), CGP57380 (0.250, 0.125, 0.0625, 0.03125, 0.15625);

(9) VSP035 (10, 5, 2.5, 1.25, 0.625), CGP57380 (constant 0.250);

(10) Torin-1 (0.250, 0.125, 0.0625, 0.03125, 0.15625);

(11) VSP035 (constant 10), Torin-1(0.250, 0.125, 0.0625, 0.03125, 0.15625);

(12) VSP035 (10, 5, 2.5, 1.25, 0.625), Torin-1 (constant 0.0625);

Test 19: SARS-CoV-2 Anti-Virus Activity of VSP035 in Huh7 Cells

SARV-CoV-2 virucidal activity of VSP035 single compound treatment using the SARS-CoV-2/Huh7-EGFP HTS antiviral Assay (96-well) (n4). This assay tests antiviral activity of the representative compound VSP035 with a sublethal dose of 10 μM (n4) reveals a 72±7.7% inhibition. Result shows a strong SARS-CoV-2 anti-virus activity of VS035 in the liver epithelial tumor cell line Huh7.

Therefore, the present invention discloses the following preferred embodiments:

1. A compound of formula (I):

(I)

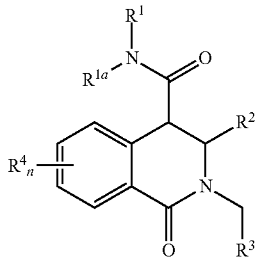

wherein $R^1$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group; all of which groups may optionally be substituted; and $R^{1a}$ is hydrogen or a $C_{1-4}$ alkyl group; or $R^1$ and $R^{1a}$ together are part of a heterocycloalkyl group containing 5 or 6 ring atoms selected from C, N and O, which heterocycloalkyl group may be unsubstituted or substituted by a group $R^{11}$;

$R^{11}$ is a $C_{1-4}$ alkyl group or a $C_{1-6}$ heteroalkyl group;

$R^2$ is a phenyl group, a naphthyl group, a heteroaryl group containing 5 or 6 ring atoms selected from C, N, O and S or a heteroaryl group comprising two rings containing a total of 9 or 10 ring atoms selected from C, N, O and S, all of which groups may be unsubstituted or substituted by one or two groups $R^{21}$;

$R^{21}$ is independently selected from halogen, a $C_{1-4}$ alkyl group and a $C_{1-4}$ heteroalkyl group;

$R^3$ is a phenyl group, a heteroaryl group containing 5 or 6 ring atoms selected from C, N, O and S, a $C_{3-7}$ cycloalkyl group or a heterocycloalkyl group containing from 3 to 7 ring atoms selected from C, N, O and S, all of which groups may be unsubstituted or substituted by one or two groups $R^{31}$;

$R^{31}$ is independently selected from halogen, a $C_{1-4}$ alkyl group and a $C_{1-4}$ heteroalkyl group;

$R^4$ is independently selected from halogen, OH, $NH_2$, SH, CN, $N_3$, $NO_2$, a $C_{1-4}$ alkyl group and a $C_{1-4}$ heteroalkyl group; or two groups $R^4$ together are a group of formula $—O—CH_2—O—$ or $—O—CH_2—CH_2—O—$; and n is 0, 1 or 2;

or a pharmaceutically acceptable salt thereof, preferably for use as an antiviral agent, more preferred as an antiviral agent against a polyomaviridae virus, an orthomyxoviridae virus or a coronaviridae virus, even more preferred for use in the treatment of a human papilloma virus (HPV) infection or for use in the treatment or prevention of SARS-CoV-2 infection, especially for use in the treatment of HPV induced malignant and neoplastic diseases or for use in the treatment or prevention of COVID-19.

2. A compound according to embodiment 1, wherein $R^4$ is selected from CI, OMe and NHAC; especially wherein $R^4$ is OMe.

3. A compound according to embodiment 1 or 2, wherein n is 0 or 1; especially wherein n is 0 or wherein n is 1 and $R^4$ is OMe.

4. A compound according to any one of the preceding embodiments, wherein $R^{1a}$ is hydrogen.

5. A compound according to any one of the preceding embodiments, wherein $R^1$ is a phenyl group, a naphthyl group, a heteroaryl group containing 5 or 6 ring atoms selected from C, N, O and S or a heteroaryl group comprising two rings containing a total of 9 or 10 ring atoms selected from C, N, O and S, all of which groups may optionally be substituted.

6. A compound according to any one of the preceding embodiments, wherein $R^1$ is a group of formula —Ar-Cy-$R^5$, wherein Ar is a phenylene group or a heteroarylene group containing 5 or 6 ring atoms selected from C, N and O; Cy is a $C_{3-7}$ cycloalkylene group or a heterocycloalkylene group containing 3, 4, 5, 6 or 7 ring atoms selected from C, N, O and S and $R^5$ is hydrogen or a $C_{1-4}$ alkyl group or a $C_{1-6}$ heteroalkyl group.

7. A compound according to embodiment 6, wherein Ar is a phenylene group and Cy is a heterocycloalkylene group containing 6 ring atoms selected from C, N and O and $R^5$ is hydrogen or a $C_{1-4}$ alkyl group.

8. A compound according to any one of the preceding embodiments, wherein $R^1$ is selected from the following groups:

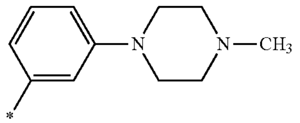
and
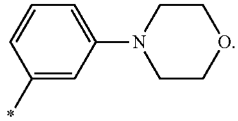

9. A compound according to any one of the preceding embodiments 1 to 4, wherein $R^1$ is a group of formula $—NH—CH_2—CH_2—N(CH_3)_2$.

10. A compound according to any one of the preceding embodiments, wherein $R^2$ is a 1,4-phenylene group carrying one group $R^{21}$.

11. A compound according to any one of the preceding embodiments, wherein $R^{21}$ is selected from F, Cl, Br, $CF_3$, $CH_3$ and OMe.

12. A compound according to any one of the preceding embodiments, wherein $R^{21}$ is a $CF_3$ group.

13. A compound according to any one of the preceding embodiments, wherein $R^3$ is a 1,4-phenylene group carrying one group $R^{31}$.

14. A compound according to any one of the preceding embodiments, wherein $R^{31}$ is selected from Cl, $CF_3$, $CH_3$, $NMe_2$ and OMe.

15. A compound according to any one of the preceding embodiments, wherein $R^2$ is a 4-chlorophenyl group and $R^3$ is a 4-methylphenyl group.

16. A compound according to any one of the preceding embodiments of formula (II):

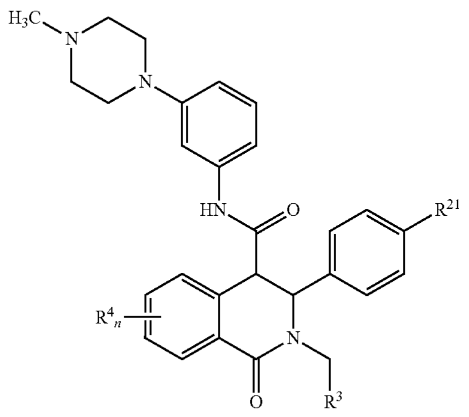
(II)

wherein $R^{21}$, $R^3$, $R^4$ and n are as defined in any one of the preceding embodiments, or a pharmaceutically acceptable salt thereof.

17. A compound according to embodiment 16, wherein n is 0 or 1; $R^4$ is OMe; $R^{21}$ is halogen, a $C_{1-4}$ alkyl group or a $C_{1-4}$ heteroalkyl group (especially a $CF_3$ group); $R^3$ is a phenyl group, a heteroaryl group containing 5 or 6 ring atoms selected from C, N, O and S, a $C_{3-7}$ cycloalkyl group or a heterocycloalkyl group containing from 3 to 7 ring atoms selected from C, N, O and S, all of which groups may be unsubstituted or substituted by one or two groups $R^{31}$; and $R^{31}$ is independently selected from halogen, a $C_{1-4}$ alkyl group and a $C_{1-4}$ heteroalkyl group.

18. A pharmaceutical composition comprising a compound according to anyone of the preceding embodiments or a pharmaceutically acceptable hydrate, solvate or salt thereof, optionally in combination with a pharmaceutically acceptable carrier.

19. A compound or a pharmaceutical composition according to anyone of the preceding embodiments for use in the treatment of an infection with a polyomaviridae virus, an orthomyxoviridae virus, especially Influenza A virus, or an infection with a coronaviridae virus, a human immunodeficiency virus (HIV), a Merkel cell polyomavirus (MCV, MCPyV), a JC polyomavirus (JCV, JCPyV), a BK polyomavirus (BKV, BKPyV), a TS polyomavirus (TSV, TSPyV), a H7 polyomavirus (HV7, HPyV7), a Simian polyomavirus 40 (SV40), a Cytomegalovirus (CMV), a Hepatitis B Virus (HEPB), a Hepatitis C Virus (HEPC), a Hepatitis D Virus (HEPD), a Human immunodeficiency virus 1 (HIV-1), a Human immunodeficiency virus 2 (HIV-2), a Human T-lymphotropic virus I (HTLV-I), a Human T-lymphotropic virus II (HTLV-II), an Epstein Bar Virus (EBV), a Karposi sarcoma-associated herpesvirus (Herpesviridae; KSHV), especially an HPV infection or a SARS-CoV-2 infection.

20. A compound or a pharmaceutical composition according to anyone of embodiments 1 to 19 for use in the treatment of HPV induced malignant and neoplastic diseases, especially cancer of the cervix, vulva, vagina, anus, penis, head and neck, as well as genital warts, subpopulations of non-melanoma skin cancer, lung-cancer, prostate and breast cancer, recurrent respiratory papillomatosis (RRP), Burkitt lymphoma, non-Hodgkin lymphoma and Bowen's disease; or for use in the prevention or treatment of infection with unicellular eukaryotic parasites, especially with *Plasmodium falciparum, Plasmodium malariae*, and *Leishmania donovani.*

21. A pharmaceutical composition comprising a combination of a signaling molecule antagonist or agonist and a compound according to anyone of embodiments 1 to 20 or a pharmaceutically acceptable hydrate, solvate or salt thereof, optionally in combination with a pharmaceutically acceptable carrier.

22. The pharmaceutical composition according to embodiment 21, wherein the signaling molecule is a receptor molecule or one or more of its downstream target, such as, EGFR, Ras, Phosphatidylinositol-4,5-bisphosphate 3-kinase alpha 85 kDa regulatory subunit or 110 kDa catalytic subunit (PI3K), Phosphatase and tensin homolog (PTEN), Protein kinase B (PKB, Akt), p70-S6 Kinase 1, mammalian target of rapamycin (mTOR1), FK506-binding protein (FKBP12), mTOR Complex 1 (mTORC1), TGFbeta pathway signaling, and/or NOTCH signaling.

23. The pharmaceutical composition according to embodiment 21, wherein the signaling molecule is a steroid receptor molecule for estrogen or a signaling molecule antagonist or agonist selected from the group mTOR inhibitor-8 (CAS No.: 2489196-70-3), mTOR inhibitor-3 (CAS No.: 1207358-59-5), mTOR inhibitor-1 (CAS No.: 468747-17-3), mTOR inhibitor-2 (CAS No.: 2219323-96-1), HDACs/mTOR Inhibitor 1 (CAS No.: 2271413-06-8), PI3K/mTOR Inhibitor-3 (CAS No.: 1363338-53-7), PI3K/mTOR Inhibitor-2 (CAS No.: 1848242-58-9), PI3K/mTOR Inhibitor-1 (CAS No.: 1949802-49-6), MTI-31 (CAS No.: 1567915-38-1), Sapanisertib (CAS No.: 1224844-38-5), WAY-600 (CAS No.: 1062159-35-6), Onatasertib (CAS No.: 1228013-30-6), MHY1485 (CAS No.: 326914-06-1), PI3Ka/mTOR-IN-1 (CAS No.: 1013098-90-2), PF-04979064 (CAS No.: 1220699-06-8), 3BDO (CAS No.: 890405-51-3), Dihydromyricetin (CAS No.: 27200-12-0), RapaLink-1 (CAS No.: 1887095-82-0), AD80 (CAS No.: 1384071-99-1), DS-7423 (CAS No.: 1222104-37-1), ETP-46464 (CAS No.: 1345675-02-6), Torin 2 (CAS No.: 1223001-51-1), PF-04691502 (CAS No.: 1013101-36-4), TFEB activator 1 (CAS No.: 39777-61-2), Vistusertib (CAS No.: 1009298-59-2), MHY-1685 (CAS No.: 27406-31-1), MCX 28 (CAS No.: 1414453-58-9), CZ415 (CAS No.: 1429639-50-8), XL388 (CAS No.: 1251156-08-7), GNE-317 (CAS No.: 1394076-92-6), NSC781406 (CAS No.: 1676893-24-5), GDC-0349 (CAS No.: 1207360-89-1), Gedatolisib (CAS No.: 1197160-78-3), Compound 401 (CAS No.: 168425-64-7), Temsirolimus (CAS No.: 162635-04-3), 28-Epirapamycin (CAS No.: 253431-35-5), GNE-477 (CAS No.: 1032754-81-6), Ridaforolimus (CAS No.: 572924-54-0), GNE-493 (CAS No.: 1033735-94-2), Bimiralisib (CAS No.: 1225037-39-7), (+)-Usnic acid (CAS No.: 7562-61-0), PP121 (CAS No.: 1092788-83-4), 42-(2-Tetrazolyl)rapamycin (CAS No.: 221877-56-1), AZD-8055 (CAS No.: 1009298-09-2), Torin 1 (CAS No.: 1222998-36-8), PKI-402 (CAS No.: 1173204-81-3), PKI-402 (CAS No.: 1173204-81-3), Chrysophanol (CAS No.: 481-74-3), VS-5584 (CAS No.: 1246560-33-7), Dactolisib (CAS No.: 915019-65-7), PI3K-IN-22 (CAS No.: 1202884-94-3), Torkinib (CAS No.: 1092351-67-1), Zeylenone (CAS No.: 193410-84-3), CC-115 (CAS No.: 1300118-55-1), Rapamycin (CAS No.: 53123-88-9), Salidroside (CAS No.: 10338-51-9), PQR626 (CAS No.: 1927857-98-4), Dactolisib Tosylate (CAS No.: 1028385-32-1), LAT1-IN-1 (CAS No.: 20448-79-7), GSK1059615 (CAS No.: 958852-01-2), Rubioncolin (C CAS No.: 132242-52-5), KU-57788 (CAS No.: 503468-95-9), Apitolisib (CAS No.: 1032754-93-0), Everolimus (CAS No.: 159351-69-6), WYE-687 (CAS No.: 1062161-90-3), SF2523 (CAS No.: 1174428-47-7), WYE-132 (CAS No.: 1144068-46-1), Lupiwighteone (CAS No.: 104691-86-3), OSI-027 (CAS No.: 936890-98-1), JR-AB2-011 (CAS No.: 2411853-34-2), SAR405 CAS No.: 1523406-39-4), WYE-687 dihydrochloride (CAS No.: 1702364-87-1), PI3Ka-IN-5 (CAS No.: 2237953-19-2), PQR530 (CAS No.: 1927857-61-1), PKI-179 (CAS No.: 1197160-28-3), WYE-354 (CAS No.: 1062169-56-5), BGT226 maleate (CAS No.: 1245537-68-1), AKT-IN-10 (CAS No.: 2709045-56-5), BGT226 (CAS No.: 915020-55-2), AKT-IN-9 (CAS No.: 2709045-53-2), PI-103 (CAS No.: 371935-74-9), Voxtalisib (CAS No.: 934493-76-2), ETP-45658 (CAS No.: 1198357-79-7), PF-06843195 (CAS No.: 2067281-51-8), (32-Carbonyl)-RMC-5552 (CAS No.: 2382768-55-8), BC-LI-0186 (CAS No.: 695207-56-8), P7 (CAS No.: 1001409-50-2), BX-320 (CAS No.: 702676-93-5), BX-517 (CAS No.: 850717-64-5), BX517 (CAS No.: 850717-64-5), BX795 (CAS No.: 702675-74-9), BX-912 (CAS No.: 702674-56-4), JX06 (CAS No.: 729-46-4), Polyphyllin I (CAS No.: 50773-41-6), PS10 (CAS No.: 1564265-82-2), PS210 (CAS No.: 1221962-86-2), PS423 (CAS No.: 1221964-37-9), PDK1-IN-RS2 (CAS No.: 1643958-89-7), GSK2334470 (CAS No.: 1227911-45-6), PF-AKT400 (CAS. Nr.: 1004990-28-6), Capivasertib (CAS. Nr.: 1143532-39-1), Afuresertib (CAS. Nr.: 1047644-62-1), Borussertib (CAS. Nr.: 1800070-77-2), GSK-690693 (CAS. Nr.: 937174-76-0), AKT-IN-10 (CAS. Nr.: 2709045-56-5), AKT-IN-9 (CAS. Nr.: 2709045-53-2), AKT-IN-3 (CAS. Nr.: 2374740-21-1), Vevorisertib (CAS. Nr.: 1416775-46-6), FPA-124 (CAS. Nr.: 902779-59-3), CCT128930 (CAS. Nr.: 885499-61-6), AT13148 (CAS. Nr.: 1056901-62-2).

24. A compound selected from the group (3R,4R)-N-[3-(4-methylpiperazin-1-yl) phenyl]-2-[(1-methylpiperidin-4-yl)methyl]-1-oxo-3-[4-(trifluoromethyl)phenyl]-1,2,3,4-tetrahydroisoquinoline-4-carboxamide), (3S,4S)-N-[3-(4-methylpiperazin-1-yl) phenyl]-2-[(1-methylpiperidin-4-yl)methyl]-1-oxo-3-[4-(trifluoromethyl)phenyl]-1,2,3,4-tetrahydroisoquinoline-4-carboxamide), (3R,4R)-N-[3-(4-methylpiperazin-1-yl) phenyl]-2-[(4-methylphenyl)methyl]-1-oxo-3-[4-(trifluoromethyl)phenyl]-1,2,3,4-tetrahydroisoquinoline-4-carboxamide) and (3S,4S)-N-[3-(4-methylpiperazin-1-yl) phenyl]-2-[(4-methylphenyl)methyl]-1-oxo-3-[4-(trifluoromethyl)phenyl]-1,2,3,4-tetrahydroisoquinoline-4-carboxamide);

preferably for use in the treatment of an HPV infection or for use in the prevention or treatment of an infection with SARS-CoV-2, especially for use in the treatment of HPV induced malignant and neoplastic diseases, especially as a degrader of protein E7, or for the prevention or treatment of COVID-19.

25. Use of a compound according to any one of embodiments 1 to 17 for the manufacture of a medicament for the treatment or prevention of an infection with a polyomaviridae virus, an orthomyxoviridae virus, especially Influenza A virus, or an infection with a coronaviridae virus, a human immunodeficiency virus (HIV), a Merkel cell polyomavirus (MCV, MCPyV), a JC polyomavirus (JCV, JCPyV), a BK polyomavirus (BKV, BKPyV), a TS polyomavirus (TSV, TSPyV), a H7 polyomavirus (HV7, HPyV7), a Simian polyomavirus 40 (SV40), a Cytomegalovirus (CMV), a Hepatitis B Virus (HEPB), a Hepatitis C Virus (HEPC), a Hepatitis D Virus (HEPD), a Human immunodeficiency virus 1 (HIV-1), a Human immunodeficiency virus 2 (HIV-2), a Human T-lymphotropic virus I (HTLV-I), a Human T-lymphotropic virus II (HTLV-II), an Epstein Bar Virus (EBV), a Karposi sarcoma-associated herpesvirus (Herpesviridae; KSHV), a Hepatitis C virus (HCV), or a Hepatitis B virus (HBV), especially an HPV infection or a SARS-CoV-2 infection; or for the treatment of HPV induced malignant and neoplastic diseases, especially cancer of the cervix, vulva, vagina, anus, penis, head and neck, as well as genital warts, subpopulations of non-melanoma skin cancer, lung-cancer, prostate and breast cancer, recurrent respiratory papillomatosis (RRP), Burkitt lymphoma, non-Hodgkin lymphoma and Bowen's disease; or for use in the prevention or treatment of infection with unicellular eukaryotic parasites, especially with *Plasmodium falciparum, Plasmodium malariae*, and *Leishmania donovani*.

26. Method of treatment or prevention of an infection with a polyomaviridae virus, an orthomyxoviridae virus, especially Influenza A virus, or an infection with a coronaviridae virus, a human immunodeficiency virus (HIV), a Merkel cell polyomavirus (MCV, MCPyV), a JC polyomavirus (JCV, JCPyV), a BK polyomavirus (BKV, BKPyV), a TS polyomavirus (TSV, TSPyV), a H7 polyomavirus (HV7, HPyV7), a Simian polyomavirus 40 (SV40), a Cytomegalovirus (CMV), a Hepatitis B Virus (HEPB), a Hepatitis C Virus (HEPC), a Hepatitis D Virus (HEPD), a Human immunodeficiency virus 1 (HIV-1), a Human immunodeficiency virus 2 (HIV-2), a Human T-lymphotropic virus I (HTLV-I), a Human T-lymphotropic virus II (HTLV-II), an Epstein Bar Virus (EBV), a Karposi sarcoma-associated herpesvirus (Herpesviridae; KSHV), a Hepatitis C virus (HCV), or a Hepatitis B virus (HBV), especially an HPV infection or a SARS-CoV-2 infection; or for the treatment and prevention of HPV induced malignant and neoplastic diseases, especially cancer of the cervix, vulva, vagina, anus, penis, head and neck, as well as genital warts, subpopulations of non-melanoma skin cancer, lung-cancer, prostate and breast cancer, recurrent respiratory papillomatosis (RRP), Burkitt lymphoma, non-Hodgkin lymphoma and Bowen's disease; or for use in the prevention or treatment of infection with unicellular eukaryotic parasites, especially with *Plasmodium falciparum, Plasmodium malariae*, and *Leishmania donovani*, wherein an effective amount of a compound according to any one of embodiments 1 to 17 is administered to a patient in need thereof.

The invention claimed is:

1. A compound selected from the group consisting of (3R,4R)-N-[3-(4-methylpiperazin-1-yl) phenyl]-2-[(1-methylpiperidin-4-yl) methyl]-1-oxo-3-[4-(trifluoromethyl) phenyl]-1,2,3,4-tetrahydroisoquinoline-4-carboxamide), (3S,4S)-N-[3-(4-methylpiperazin-1-yl) phenyl]-2-[(1-methylpiperidin-4-yl) methyl]-1-oxo-3-[4-(trifluoromethyl) phenyl]-1,2,3,4-tetrahydroisoquinoline-4-carboxamide), (3R,4R)-N-[3-(4-methylpiperazin-1-yl) phenyl]-2-[(4-methylphenyl) methyl]-1-oxo-3-[4-(trifluoromethyl) phenyl]-1,2,3,4-tetrahydroisoquinoline-4-carboxamide), (3S,4S)-N-[3-(4-methylpiperazin-1-yl) phenyl]-2-[(4-methylphenyl) methyl]-1-oxo-3-[4-(trifluoromethyl) phenyl]-1,2,3,4-tetrahydroisoquinoline-4-carboxamide), (3R,4R)-2-(4-methylbenzyl)-N-(3-(4-methylpiperazin-1-yl) phenyl)-1-oxo-3-(6-(trifluoromethyl) pyridin-3-yl)-1,2,3,4-tetrahydroisoquinoline-4-carboxamide, (3R,4R)-7-methoxy-2-(4-methylbenzyl)-N-(3-(4-methylpiperazin-1-yl) phenyl)-1-oxo-3-(4-(trifluoromethyl) phenyl)-1,2,3,4-tetrahydroisoquinoline-4-carboxamide, (3R,4R)-7-acetamido-2-(4-methylbenzyl)-N-(3-(4-methylpiperazin-1-yl) phenyl)-1-oxo-3-(4-(trifluoromethyl) phenyl)-1,2,3,4-tetrahydroisoquinoline-4-carboxamide, (3R,4R)-6,7-dimethoxy-2-(4-methylbenzyl)-N-(3-(4-methylpiperazin-1-yl) phenyl)-1-oxo-3-(4-(trifluoromethyl) phenyl)-1,2,3,4-tetrahydroisoquinoline-4-carboxamide, (3R,4R)-2-(4-methylbenzyl)-N-(4-(4-methylpiperazin-1-yl) phenyl)-1-oxo-3-(4-(trifluoromethyl) phenyl)-1,2,3,4-tetrahydroisoquinoline-4-carboxamide, (3R,4R)-2-(4-methylbenzyl)-N-(3-morpholinophenyl)-1-oxo-3-(4-(trifluoromethyl) phenyl)-1,2,3,4-tetrahydroisoquinoline-4-carboxamide, (3R,4R)-N-(3-(4-methylpiperazin-1-yl) phenyl)-1-oxo-2-(pyridin-4-ylmethyl)-3-(4-(trifluoromethyl) phenyl)-1,2,3,4-tetrahydroisoquinoline-4-carboxamide, (3R,4R)-N-(3-(4-methylpiperazin-1-yl) phenyl)-1-oxo-2-(pyridin-3-ylmethyl)-3-(4-(trifluoromethyl) phenyl)-1,2,3,4-tetrahydroisoquinoline-4-carboxamide, (3S,4S)-2-(4-methylbenzyl)-N-(3-(4-methylpiperazin-1-yl) phenyl)-1-oxo-3-(6-(trifluoromethyl) pyridin-3-yl)-1,2,3,4-tetrahydroisoquinoline-4-carboxamide, (3S,4S)-7-methoxy-2-(4-methylbenzyl)-N-(3-(4-methylpiperazin-1-yl) phenyl)-1-oxo-3-(4-(trifluoromethyl) phenyl)-1,2,3,4-tetrahydroisoquinoline-4-carboxamide, (3S,4S)-7-acetamido-2-(4-methylbenzyl)-N-(3-(4-methylpiperazin-1-yl) phenyl)-1-oxo-3-(4-(trifluoromethyl) phenyl)-1,2,3,4-tetrahydroisoquinoline-4-carboxamide, (3S,4S)-6,7-dimethoxy-2-(4-methylbenzyl)-N-(3-(4-methylpiperazin-1-yl) phenyl)-1-oxo-3-(4-(trifluoromethyl) phenyl)-1,2,3,4-tetrahydroisoquinoline-4-carboxamide, (3S,4S)-2-(4-methylbenzyl)-N-(4-(4-methylpiperazin-1-yl) phenyl)-1-oxo-3-(4-(trifluoromethyl) phenyl)-1,2,3,4-tetrahydroisoquinoline-4-carboxamide, (3S,4S)-2-(4-methylbenzyl)-N-(3-morpholinophenyl)-1-oxo-3-(4-(trifluoromethyl) phenyl)-1,2,3,4-tetrahydroisoquinoline-4-carboxamide, (3S,4S)-N-(3-(4-methylpiperazin-1-yl) phenyl)-1-oxo-2-(pyridin-4-ylmethyl)-3-(4-(trifluoromethyl) phenyl)-1,2,3,4-tetrahydroisoquinoline-4-carboxamide, and (3S,4S)-N-(3-(4-methylpiperazin-1-yl) phenyl)-1-oxo-2-(pyridin-3-ylmethyl)-3-(4-(trifluoromethyl) phenyl)-1,2,3,4-tetrahydroisoquinoline-4-carboxamide.

2. An antiviral agent comprising a compound according to claim 1.

3. The antiviral agent of claim 2, wherein said antiviral agent acts against a polyomaviridae virus or an orthomyxoviridae virus, especially Influenza A virus.

4. The antiviral agent of claim 2, wherein said antiviral agent acts against a coronaviridae virus, a human immunodeficiency virus (HIV), a Merkel cell polyomavirus (MCV, MCPyV), a JC polyomavirus (JCV, JCPyV), a BK polyomavirus (BKV, BKPyV), a TS polyomavirus (TSV, TSPyV), a H7 polyomavirus (HV7, HPyV7), a Simian polyomavirus 40 (SV40), a Cytomegalovirus (CMV), a Hepatitis B Virus (HEPB), a Hepatitis C Virus (HEPC), a Hepatitis D Virus (HEPD), a Human immunodeficiency virus 1 (HIV-1), a Human immunodeficiency virus 2 (HIV-2), a Human T-lymphotropic virus I (HTLV-I), a Human T-lymphotropic virus II (HTLV-II), an Epstein Bar Virus (EBV), or a Karposi sarcoma-associated herpesvirus (Herpesviridae; KSHV).

5. A method of treating or preventing a disease or condition comprising administering to a patient in need thereof an effective amount of the antiviral agent of claim 2, wherein said disease or condition is a human papilloma virus (HPV) infection, SARS-COV-2 infection, one or more HPV induced malignant and neoplastic diseases, or COVID-19.

6. The antiviral agent of claim 2, wherein said antiviral agents acts as a degrader of protein E7.

7. A pharmaceutical composition comprising a compound according to claim 1 or a pharmaceutically acceptable hydrate, solvate or salt of this compound, optionally in combination with a pharmaceutically acceptable carrier.

8. A method of treating an HPV infection or preventing or treating an infection with SARS-CoV-2 comprising administering to a patient in need thereof an effective amount of a pharmaceutical composition comprising a compound according to claim 1 or a pharmaceutically acceptable hydrate, solvate or salt of this compound, optionally in combination with a pharmaceutically acceptable carrier.

9. A method of treating one or more HPV induced malignant and neoplastic diseases comprising administering to a patient in need thereof an effective amount of a pharmaceutical composition comprising a compound according to claim 1 or a pharmaceutically acceptable hydrate, solvate or salt of this compound, optionally in combination with a pharmaceutically acceptable carrier.

10. The method of claim 9, wherein said compound acts as a degrader of protein E7.

11. A method of preventing or treating COVID-19 comprising administering to a patient in need thereof an effective amount of a pharmaceutical composition comprising a compound according to claim 1 or a pharmaceutically acceptable hydrate, solvate or salt of this compound, optionally in combination with a pharmaceutically acceptable carrier.

* * * * *